US012329446B2

United States Patent
Ibrahim et al.

(10) Patent No.: US 12,329,446 B2
(45) Date of Patent: *Jun. 17, 2025

(54) STABILIZED ABLATION SYSTEMS AND METHODS

(71) Applicant: AtriCure, Inc., Mason, OH (US)

(72) Inventors: Tamer Ibrahim, Danville, CA (US);
Dwight P. Morejohn, Davis, CA (US);
Michael J. Banchieri, Discovery Bay, CA (US); Ara Stephanian, Davis, CA (US); John D. Pavlidis, Los Altos, CA (US); David K. Swanson, Campbell, CA (US)

(73) Assignee: AtriCure, Inc., Mason, OH (US)

(*) Notice: Subject to any disclaimer, the term of this patent is extended or adjusted under 35 U.S.C. 154(b) by 861 days.

This patent is subject to a terminal disclaimer.

(21) Appl. No.: 17/643,238

(22) Filed: Dec. 8, 2021

(65) Prior Publication Data

US 2022/0151694 A1    May 19, 2022

Related U.S. Application Data

(63) Continuation of application No. 16/286,173, filed on Feb. 26, 2019, now Pat. No. 11,224,481, which is a
(Continued)

(51) Int. Cl.
*A61B 18/14* (2006.01)
*A61B 18/00* (2006.01)
(Continued)

(52) U.S. Cl.
CPC . *A61B 18/1492* (2013.01); *A61B 2018/00011* (2013.01); *A61B 2018/00291* (2013.01); *A61B 2018/00357* (2013.01); *A61B 2018/00375* (2013.01); *A61B 2018/00577* (2013.01); *A61B 2018/00613* (2013.01);
(Continued)

(58) Field of Classification Search
CPC . A61B 18/02; A61B 18/1492; A61B 18/1815; A61B 18/20; A61B 2018/00011; A61B 2018/142; A61B 2018/00577
See application file for complete search history.

(56) References Cited

U.S. PATENT DOCUMENTS 6,475,179 B1  11/2002 Wang et al.
6,514,250 B1  2/2003 Jahns et al.
(Continued)

FOREIGN PATENT DOCUMENTS

EP   1518507      3/2005
JP   2004-500917  1/2004
(Continued)

OTHER PUBLICATIONS

Cragg, et al., "Endovascular diathermic vessel occlusion," *Radiology*, 144:303-308, 1982.
(Continued)

*Primary Examiner* — Ashley L Fishback
(74) *Attorney, Agent, or Firm* — Levine Bagade Han LLP

(57) ABSTRACT

Surgical systems and methods for administering an ablation treatment and other therapeutic or diagnostic protocols to a patient tissue involve a flexible stabilizer mechanism having an inner recess and an ablation mechanism coupled with the stabilizer mechanism.

15 Claims, 51 Drawing Sheets

Related U.S. Application Data continuation of application No. 15/334,157, filed on Oct. 25, 2016, now Pat. No. 10,251,699, which is a continuation of application No. 13/473,311, filed on May 16, 2012, now Pat. No. 9,474,574, which is a continuation-in-part of application No. 13/295,852, filed on Nov. 14, 2011, now abandoned.

(60) Provisional application No. 61/456,918, filed on Nov. 12, 2010.

(51) Int. Cl.
| | |
|---|---|
| *A61B 18/18* | (2006.01) |
| *A61B 18/02* | (2006.01) |
| *A61B 18/20* | (2006.01) |
| *A61B 90/00* | (2016.01) |
| *A61N 7/02* | (2006.01) |

(52) U.S. Cl.
CPC ........... *A61B 2018/00791* (2013.01); *A61B 2018/00821* (2013.01); *A61B 18/02* (2013.01); *A61B 2018/142* (2013.01); *A61B 2018/1467* (2013.01); *A61B 18/1815* (2013.01); *A61B 18/20* (2013.01); *A61B 2090/064* (2016.02); *A61B 2218/002* (2013.01); *A61N 7/022* (2013.01)

(56) References Cited

U.S. PATENT DOCUMENTS

| | | | |
|---|---|---|---|
| 9,474,574 | B2 | 10/2016 | Ibrahim et al. |
| 10,251,699 | B2 | 4/2019 | Ibrahim et al. |
| 11,224,481 | B2 | 1/2022 | Ibrahim et al. |
| 2003/0069572 | A1 | 4/2003 | Wellman et al. |
| 2005/0251133 | A1 | 11/2005 | Jahns et al. |
| 2017/0258520 | A1 | 9/2017 | Ibrahim et al. |
| 2019/0247113 | A1 | 8/2019 | Ibrahim et al. |

FOREIGN PATENT DOCUMENTS

| | | |
|---|---|---|
| JP | 2005-512668 | 5/2005 |
| WO | WO 2001/058373 | 8/2001 |
| WO | WO 2001/080755 | 11/2001 |
| WO | WO 2003/053259 | 7/2003 |
| WO | WO 2004/028233 | 6/2004 |
| WO | WO 2004/093698 | 11/2004 |
| WO | WO 2005/046456 | 5/2005 |
| WO | WO 2006/009856 | 1/2006 |

OTHER PUBLICATIONS

Gorisch et al., "Heat-induced contraction of blood vessels," *Lasers in Surgery and Medicine*, 2:1-13, 1982.
Nath, et al., "Cellular electrophysiologic effects of hyperthermia on isolated guinea pig papillary muscle: implications for catheter ablation," *Circulation*, 88:1826-1831, 1993.
U.S. Appl. No. 16/286,173, filed Feb. 26, 2019.
U.S. Appl. No. 15/334,157, filed Oct. 25, 2016.
U.S. Appl. No. 13/473,311, filed May 16, 2012.
U.S. Appl. No. 13/295,852, filed Nov. 14, 2011.

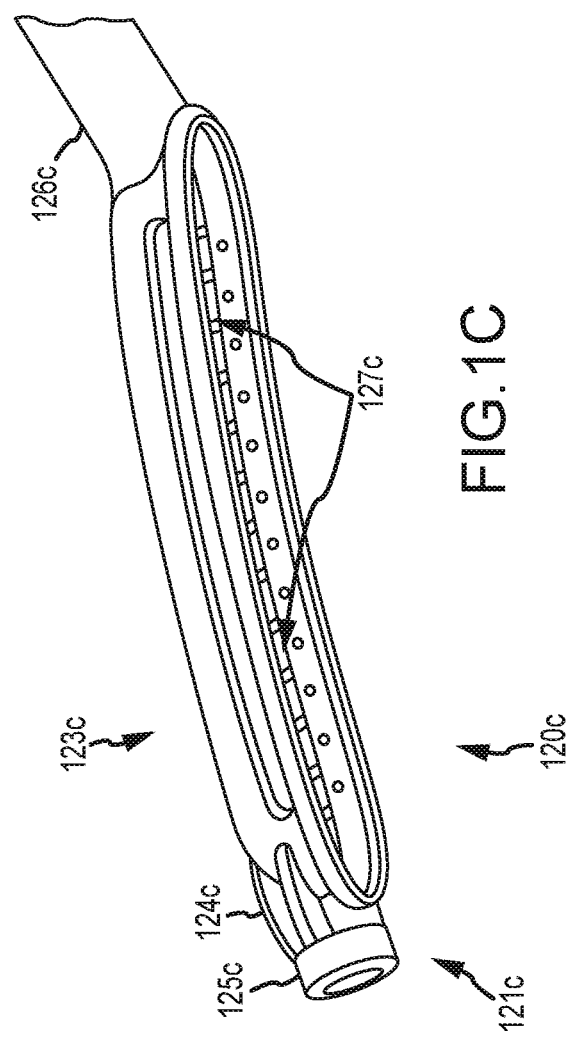

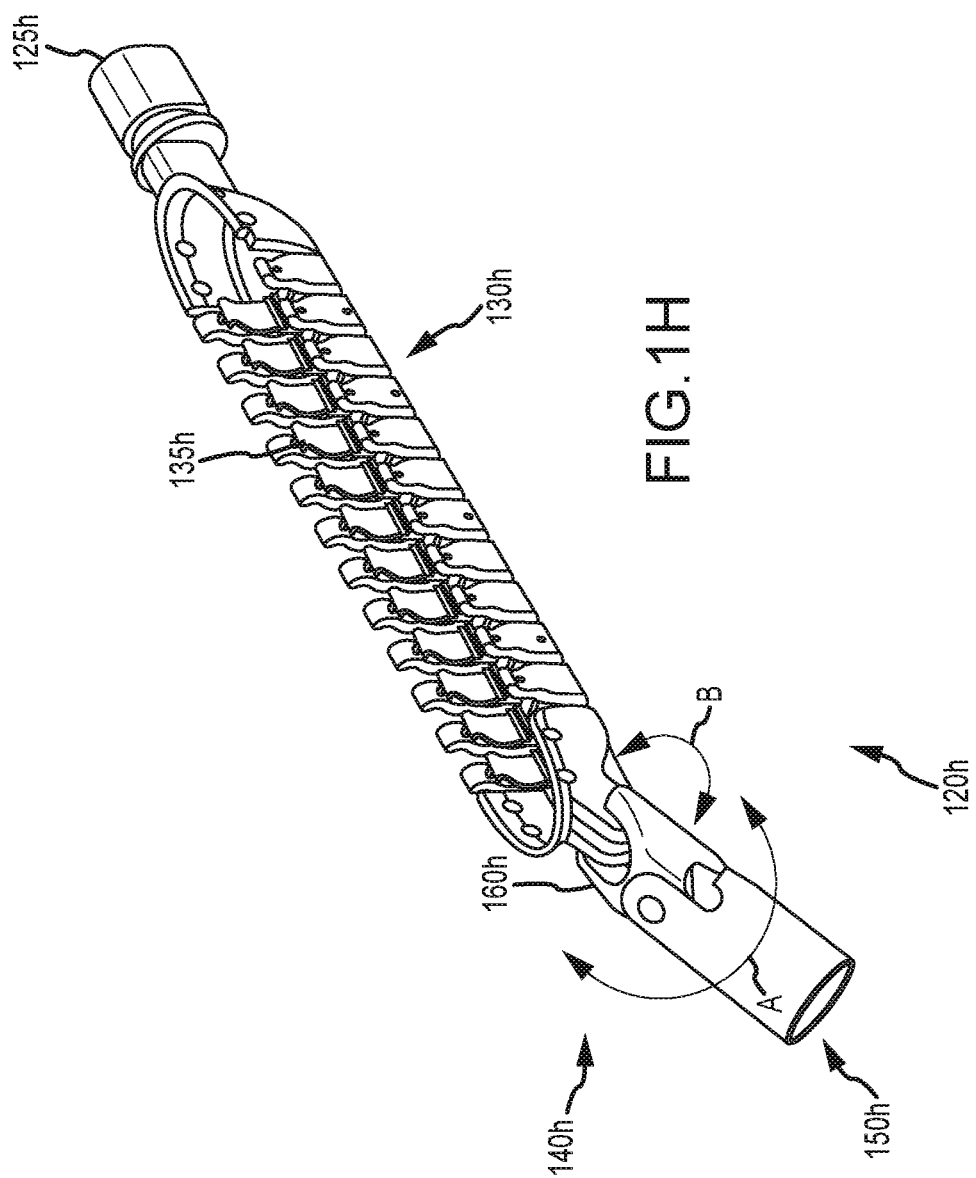

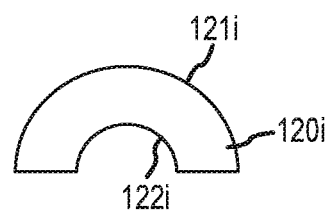
FIG. 1I
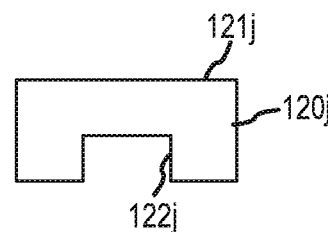
FIG. 1J
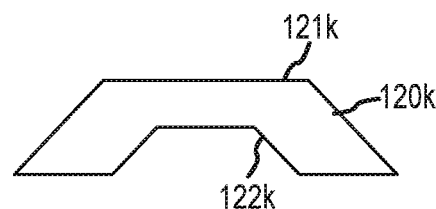
FIG. 1K
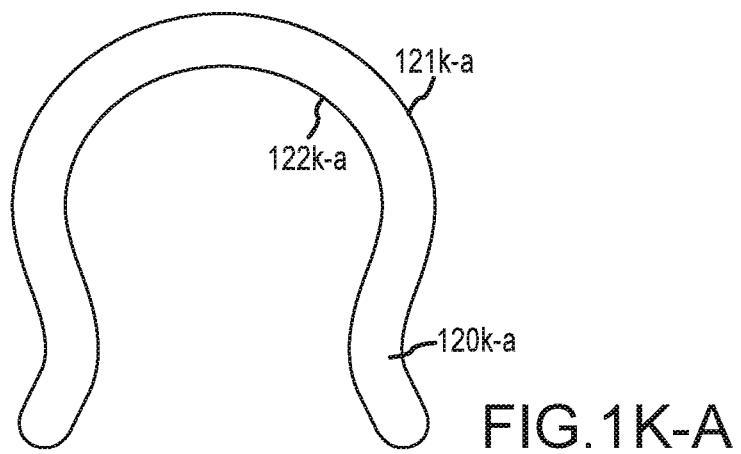
FIG. 1K-A

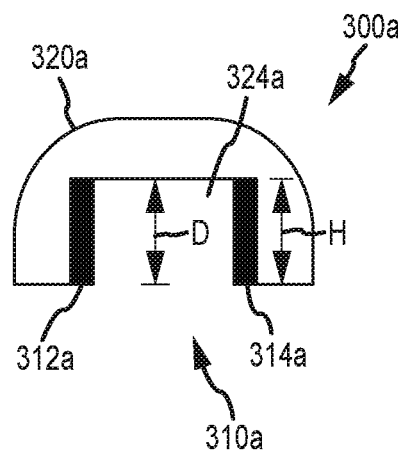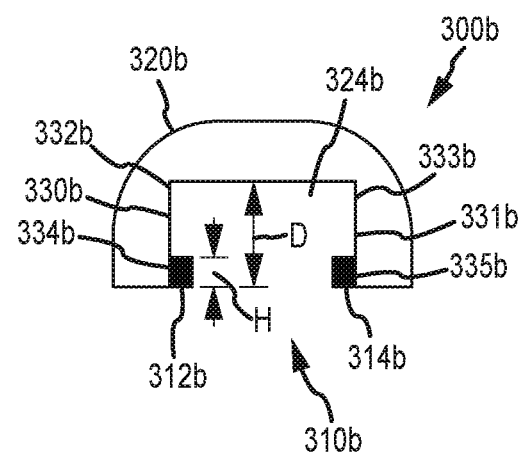
FIG.3A　　　　　　FIG.3B
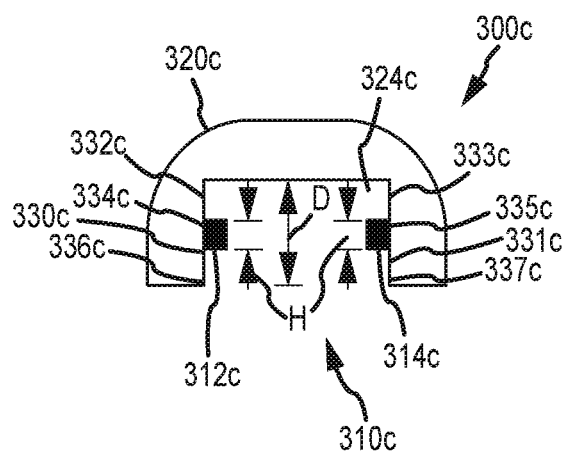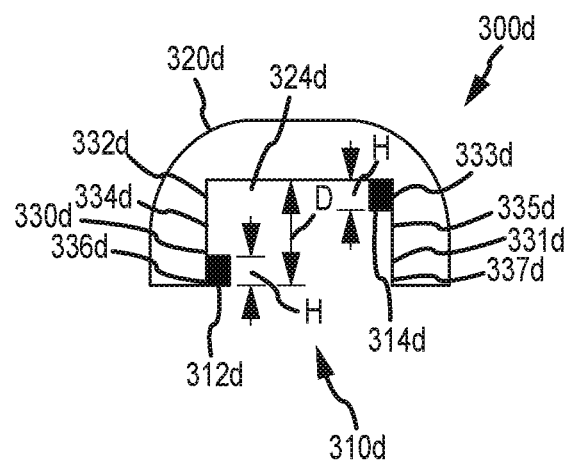
FIG.3C　　　　　　FIG.3D

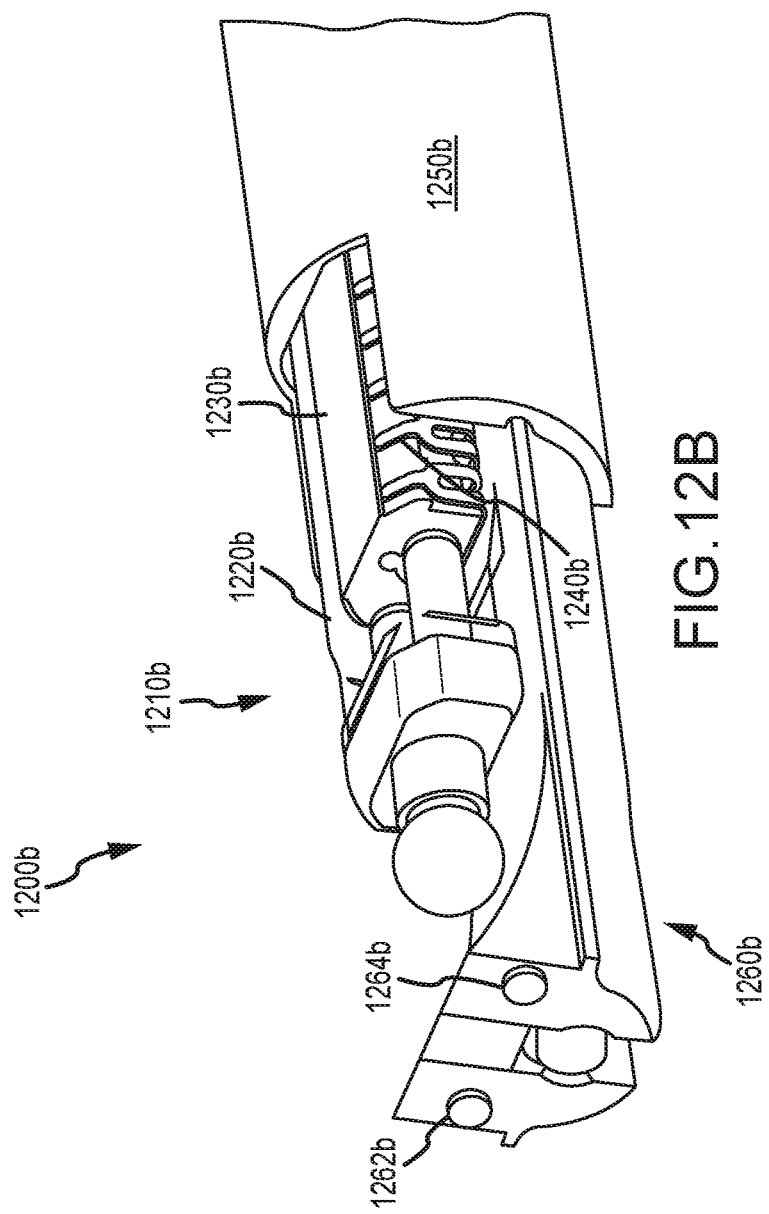

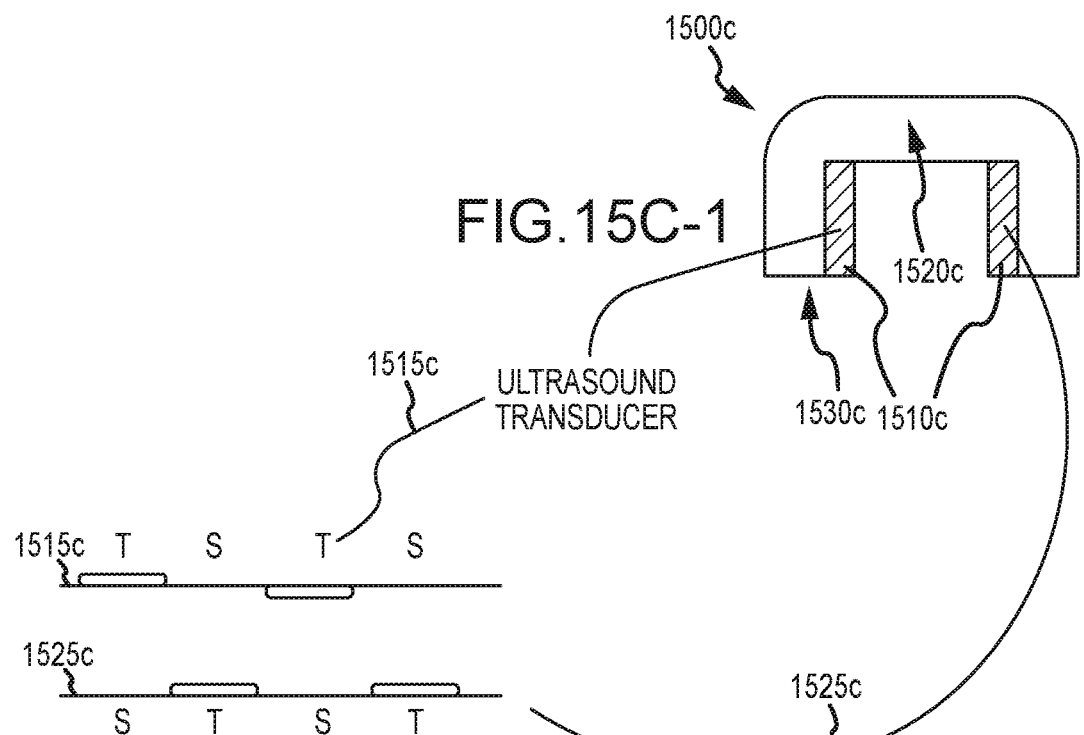
FIG. 15C-1
FIG. 15C-2
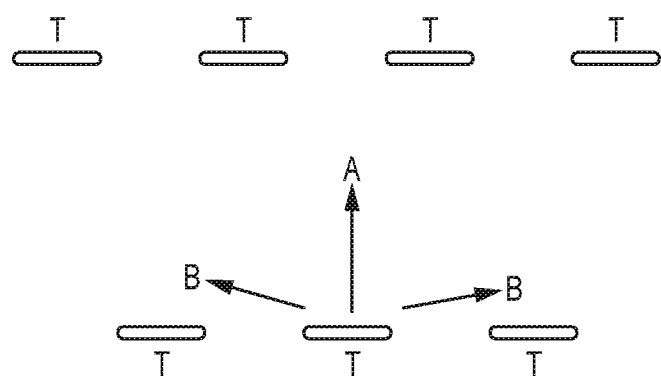
FIG. 15C-3

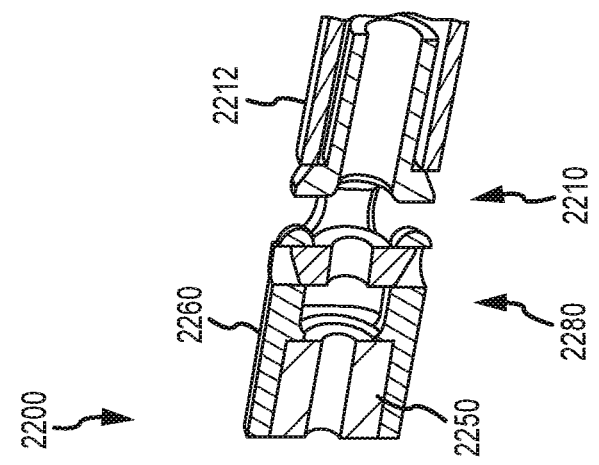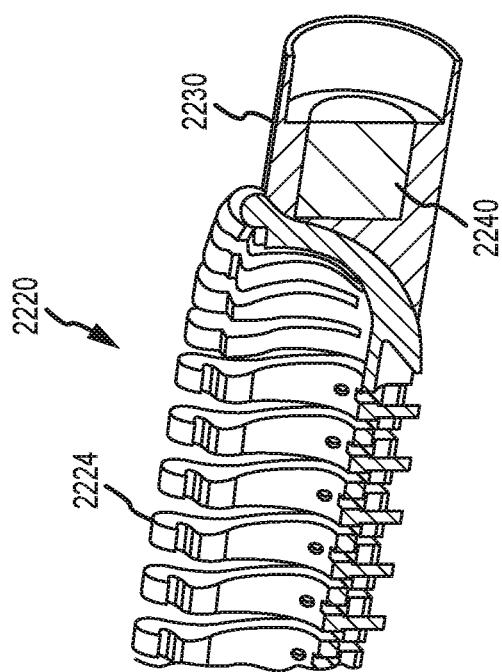
FIG.22

STABILIZED ABLATION SYSTEMS AND METHODS

CROSS-REFERENCES TO RELATED APPLICATIONS

This application is a continuation of U.S. patent application Ser. No. 16/286,173 filed Feb. 26, 2019, entitled STABILIZED ABLATION SYSTEMS AND METHODS," which is a continuation of U.S. patent application Ser. No. 15/334,157 filed Oct. 25, 2016, entitled "STABILIZED ABLATION SYSTEMS AND METHODS," which is a continuation of U.S. patent application Ser. No. 13/473,311, filed May 16, 2012, entitled "STABILIZED BIPOLAR ABLATION SYSTEMS AND METHODS," which is a continuation-in-part (CIP) of U.S. patent application Ser. No. 13/295,852 filed Nov. 14, 2011, entitled "STABILIZED BIPOLAR ABLATION SYSTEMS AND METHODS," which is a nonprovisional claiming the benefit of priority to U.S. Provisional Patent Application No. 61/456,918 filed Nov. 12, 2010, entitled "STABILIZED BIPOLAR ABLATION SYSTEMS AND METHODS." This application is also related to U.S. patent application Ser. Nos. 12/124,743 and 12/124,766, filed May 21, 2008. The entire content of each of the above filings is incorporated herein by reference for all purposes.

BACKGROUND OF THE INVENTION

Embodiments of the present invention related generally to the field of medical devices and methods, and in particular to therapeutic modalities involving tissue ablation or lesion formation.

There are many instances where it is beneficial to perform a therapeutic intervention in a patient, using a system that is inserted within the patient's body. One exemplary therapeutic intervention involves the formation of therapeutic lesions in the patient's heart tissue to treat cardiac conditions such as atrial fibrillation, atrial flutter, and arrhythmia. Therapeutic lesions may also be used to treat conditions in other regions of the body including, but not limited to, the prostate, liver, brain, gall bladder, uterus, and other solid organs. Typically, the lesions are formed by ablating tissue with one or more electrodes. Electromagnetic radio frequency ("RF") energy applied by the electrode heats and eventually kills or ablates the tissue to form a lesion. During the ablation of soft tissue (e.g. tissue other than blood, bone and connective tissue), tissue coagulation occurs, which leads to tissue death. Thus, references to the ablation of soft tissue are typically references to soft tissue coagulation. "Tissue coagulation" can refer to the process of cross linking proteins in tissue to cause the tissue to jell. In soft tissue, it is the fluid within the tissue cell membranes that jells to kill the cells, thereby killing the tissue. Depending on the procedure, a variety of different electrophysiology devices may be used to position one or more electrodes at the target location. Electrodes can be connected to power supply lines and, in some instances, the power to the electrodes can be controlled on an electrode-by-electrode basis. Examples of electrophysiology devices include catheters, surgical probes, and clamps.

Currently known surgical probes which can be used to create lesions often include a handle, a relatively short shaft that is from 4 inches to 18 inches in length and either rigid or relatively stiff, and a distal section that is from 1 inch to 10 inches in length and either malleable or somewhat flexible. One or more electrodes are carried by the distal section. Surgical probes are used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994, the content of which is incorporated herein by reference.

Clamps, which have a pair of opposable clamp members that may be used to hold a bodily structure or a portion thereof, are used in many types surgical procedures. Lesion creating electrodes have also been secured to certain types of clamps. Examples of clamps which carry lesion creating electrodes are discussed in U.S. Pat. No. 6,142,994, and U.S. Patent Publication Nos. 2003/0158549, 2004/0059325, and 2004/024175, the contents of which are incorporated herein by reference. Such clamps can be useful when the physician intends to position electrodes on opposite sides of a body structure in a bipolar arrangement.

Atrial fibrillation (AF) can refer to a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is a common clinical condition, and presents a substantial medical issue to aging populations. AF is costly to health systems, and can cause complications such as thrombo-embolism, heart failure, electrical and structural remodeling of the heart, and even death. Relatedly, AF typically increases the risk of acquiring a number of potentially deadly complications, including thrombo-embolic stroke, dilated cardiomyopathy, and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3%/year of those aged 50-59 to more than 7%/year of those aged 80 and over. AF is responsible for up to 35% of the strokes that occur in people older than age 85. Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be under prescribed for AF. Despite the fact that warfarin reduces stroke risk by 60% or more, only 40% of patients age 65-74 and 20% of patients over age 80 take the medication, and probably fewer than half are on the correct dosage. Patient compliance with pharmacological intervention such as warfarin is problematic, and the drug requires vigilant blood monitoring to reduce the risk of bleeding complications.

More recently, the focus has shifted toward surgical or catheter ablation options to treat or effect a cure for AF. The ablation techniques for producing lines of electrical isolation are now replacing the so-called Maze procedure. The Maze procedure uses a set of transmural surgical incisions on the atria to create fibrous scars in a prescribed pattern. This procedure was found to be highly efficacious but was associated with a high morbidly rate. The more recent approach of making lines of scar tissue with modern ablation technology has enabled the electrophysiologist or cardiac surgeon to create the lines of scar tissue more safely. Ideally, re-entrant circuits that perpetuate AF can be interrupted by the connected lines of scar tissue, and the goal of achieving normal sinus rhythm in the heart may be achieved.

Electrophysiologists often classify AF by the "three Ps": paroxysmal, persistent, or permanent. Paroxysmal AF, typically characterized by sporadic, usually self-limiting episodes lasting less than 48 hours, is usually the most amenable to treatment, while persistent or permanent AF can be much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is often characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Triggers for intermittent AF and drivers for permanent AF can be located at various places on the heart, such as the atria. For example, where triggers or drivers are located near the pulmonary veins, it follows that treatment may involve electrical isolation of the pulmonary veins. Technologies designed to isolate the pulmonary veins or ablate specific pulmonary foci appear to be very promising and are the focus of much of the current research in catheter-based ablation techniques.

Certain cardiac surgical procedures involve administering ablative energy to the cardiac tissue in an attempt to create a transmural lesion on the tissue. However, with some current ablation approaches, including RF, microwave, infrared laser, cryo-thermal, irreversible electroporation, and ultrasound ablation technologies, there may be difficulties in making transmural lesions as desired. Thus, although cardiac ablation devices and methods are currently available and provide real benefits to patients in need thereof, many advances may still be made to provide improved devices and methods for ablating epicardial tissue to treat AF and other arrhythmias. For example, there continues to be a need for improved systems and methods that can effectively deliver ablative energy to patient tissue in a flexible manner, especially on the actively working heart. Embodiments of the present invention provide solutions that address the problems described above, and hence provide answers to at least some of these outstanding needs.

BRIEF SUMMARY OF THE INVENTION

Embodiments of the present invention provide systems and methods for administering minimally invasive stand-alone atrial fibrillation therapy, optionally involving the use of unipolar and bipolar ablation techniques, and encompass treatments involving box lesions, connecting lesions, and conduction block. For example, embodiments encompass systems and methods for performing cardiac and other surgical procedures. As described herein, an ablative lesion can be created thermally by heating tissue with energy transmitted into tissue using, for example, microwave, infrared light, ultrasound waves, or radiofrequency (RF) energy. Alternatively, lesions can be formed by freezing tissues below −40° C., or by killing tissue by non-thermal means, such as with radiation, toxic chemicals, or with irreversible electroporation.

One of the preferred ablative technologies is RF ablation. As disclosed herein, the terms "unipolar" and "monopolar" may be used interchangeably. Exemplary techniques involve the administration of radiofrequency (RF) ablation energy, often in a temperature controlled manner. Temperature control can be used to maintain tissue at desired temperatures when producing a lesion or lesion set. In some cases, internal probe cooling and suction mechanisms also help to ensure reproducible transmural, or full-thickness, endocardial or epicardial lesions. Such systems and methods can be used for minimally invasive or traditional procedures either stand-alone or concomitant with valve or coronary artery bypass graft (CABG) surgery, for example with access via surgical access approaches including sternotomy, thoracotomy, port access, subxyphoid, transdiaphragmatic, or these in any combination.

Embodiments also encompass surgical systems that provide a minimally invasive epicardial surgical catheter which uses one or more electrodes to create contiguous lesions on a patient tissue. Exemplary techniques involve a bipolar linear ablation probe that can be applied with suction to a patient tissue. Suction stabilizer or pod mechanisms can operate to pull atrial tissue flush to the probe, so as to ensure a consistent and reproducible lesion set. System configurations can help to overcome or counteract the heat sink effect, while preventing or inhibiting the formation of coagulum at the tissue surface. Systems can be advanced through ports or small incisions, in order to create a lesion set on the patient tissue. Suction mechanisms can ensure the precise delivery of ablation energy with minimal or no gaps. Systems can incorporate electrode shielding mechanisms which help provide for the uni-directional delivery of ablation energy, without unwanted collateral tissue damage. The ablation energy output of individual ablation electrodes can be automatically adjusted so as to accommodate for variable tissue thicknesses. System and method embodiments of the present invention allow a surgeon to create a long contiguous lesion using standard surgical techniques or minimally invasive approaches, including without limitation unilateral port access protocols, bilateral port access protocols, right mini-thoracotomy protocols, bilateral mini-thoracotomy protocols, and sternotomy protocols. By using suction to assist in applying an ablation probe or mechanism, contact between the ablation probe or mechanism can be optimized, and tissue gaps and the potential for inadvertent heating or surrounding tissues can be eliminated. Power can be temperature regulated to use only the amount of energy desired to effectively create the lesion while maintaining tissue at safe temperatures. Exemplary system configurations can provide an effective lesion by overcoming the heat sink and minimizing char. For example, cooling features such as internal cooling mechanisms can prevent or inhibit char and coagulum which act as an impedance barrier at the tissue surface and prevent or inhibit the delivery of ablation energy to deep tissue structures. In some embodiments, saline or other cooling fluid can be circulated through an ablation probe or mechanism to prevent or inhibit such char and coagulum formation. The control of heat removal and conduction is helpful in maintaining tissue temperature at a desired level, for example above 50° Celsius, thus promoting a full-thickness lesion. In some instances, embodiments may include systems having electrodes which are cooled by any of a variety of cooling means. For example, a probe assembly may include internal cooling means disposed near or adjacent to one or more electrodes for cooling such electrodes.

Embodiments of the present invention further encompass bimodal systems and methods, wherein an energy delivery device can be designated or selected to perform in either a monopolar mode or a bipolar mode. For example, either a monopolar or a bipolar mode can be selected by the operator. In some instances, the operator may designate or select the monopolar mode or bipolar mode using a switch in the device handle. In some instances, the operator may designate or select the monopolar mode or bipolar mode using a switch of a generator or electrosurgical unit (or a switch device attached thereto). In some instances, selection of either a monopolar or a bipolar mode can be performed by an algorithm of the generator. Relatedly, embodiments encompass a computer-readable medium that stores instructions executable by one or more processors to perform a method of designating or selecting a monopolar mode or a bipolar mode for operation of an electrosurgical unit. In some instances, systems and methods may encompass a monopolar mode that involves a double monopolar approach, wherein dual side-by-side electrode sets can deliver energy to the tissue one at a time or both together. Such embodiments may include, for example, a first monopolar electrode set positioned alongside a second monopolar electrode set. In some instances, systems or methods may involve an electrode set, for example a single monopolar electrode set, disposed along or in alignment with a centerline of a flexible stabilizer mechanism. Such embodiments can form or provide an electrode planar or curved surface for contacting a tissue.

In one aspect, embodiments of the present invention encompass systems and methods for administering an ablation treatment to a patient tissue. Exemplary systems may include a flexible stabilizer mechanism having an inner recess, and an ablation mechanism coupled with the stabilizer mechanism. The ablation mechanism may include an active electrode assembly disposed along a first side of the inner recess of the stabilizer mechanism, and a return electrode assembly disposed along a second side of the inner recess of the stabilizer mechanism. In some cases, the flexible stabilizer mechanism is configured to deliver suction to a portion of the patient tissue, so as to draw the portion of the patient tissue into the inner recess of the stabilizer mechanism, and between the active electrode assembly and the return electrode assembly. In some cases, systems may also include a temperature sensor in thermal association with the active electrode. In some cases, systems may also include a temperature sensor in thermal association with the return electrode. In some cases, systems may also include a temperature sensor disposed along a central portion of the stabilizer mechanism inner recess. Embodiments of the present invention further encompass systems having a cinching mechanism configured to constrict the ablation mechanism about the patient tissue. In some instances, an active electrode assembly may include at least 6 active electrodes. In some instances, a return electrode assembly may include more than one return electrode. In some instances, systems may further include a second active electrode assembly disposed along the first side of the inner recess of the stabilizer mechanism. In some instances, systems may further include a second return electrode assembly disposed along the second side of the inner recess of the stabilizer mechanism. Optionally, a stabilizer mechanism may include a cooling lumen. In some cases, a stabilizer mechanism may include an irrigation lumen. In some cases, a stabilizer mechanism may include a pocket that channels a vacuum delivered by the stabilizer mechanism. In some instances, a surgical system may include an ablation device connector for coupling with an electrosurgical unit. An ablation device connector may include couplings for delivering a pacing protocol to the patient via the ablation mechanism. Some surgical systems may include a steerable member in operative association with the stabilizer mechanism. According to some embodiments, surgical systems may include a first rail coupled with a first external side of the stabilizer mechanism, and a second rail coupled with a second external side of the stabilizer mechanism. In some cases, surgical systems may include a clamping instrument that tracks along at least one of the first and second rails. In some instances, an active electrode assembly may include an active electrode having an active surface and a return electrode assembly may include a return electrode having a return surface, such that the active surface and return are angularly offset when the stabilizer mechanism is in a relaxed configuration and substantially parallel when the stabilizer mechanism is in a clamped configuration.

In another aspect, embodiments of the present invention encompass methods for administering an ablation treatment to a patient tissue. Exemplary methods may include placing a treatment assembly near the tissue of the patient. Such treatment assemblies may include a flexible stabilizer mechanism having an inner recess and an ablation mechanism coupled with the stabilizer mechanism. An ablation mechanism may include an active electrode assembly disposed along a first side of the inner recess of the stabilizer mechanism, and a return electrode assembly disposed along a second side of the inner recess of the stabilizer mechanism. Methods may also include delivering a vacuum through the stabilizer mechanism so as to draw a portion of the patient tissue into the inner recess of the stabilizer mechanism, and between the active electrode assembly and the return electrode assembly. Further, methods may include administering a bipolar ablation to the tissue via the ablation mechanism to create a lesion in the tissue. In some instances, methods may include cinching the flexible stabilizer mechanism against the patient tissue prior to administering the bipolar ablation.

In another aspect, embodiments of the present invention encompass systems for administering a treatment to a patient tissue. An exemplary system may include a flexible stabilizer mechanism having an inner recess, a sheath that translates longitudinally relative to the stabilizer mechanism, and an ablation mechanism coupled with the stabilizer mechanism. The ablation mechanism may include a first electrode assembly disposed along a first side of the inner recess of the stabilizer mechanism, and a second electrode assembly disposed along a second side of the inner recess of the stabilizer mechanism. In some instances, the system is configured to provide a tissue ablation treatment to the patient when the sheath is in a first configuration that exposes a first amount of electrode assembly surface area, and a tissue pacing treatment to the patient when the sheath is in a second configuration that exposes a second amount of electrode assembly area that is less than the first amount of electrode assembly surface area. According to some embodiments, systems may include a multifunction connector that connects the first and second electrode assemblies with an electrosurgical unit.

In still another aspect, embodiments of the present invention encompass surgical system for administering an ablation treatment to a patient tissue. Exemplary surgical systems may include a flexible stabilizer mechanism having an inner recess, and a ribcage mechanism disposed at least partially within the inner recess of the stabilizer mechanism. The ribcage mechanism can have an inner recess. Systems may further include an ablation mechanism coupled with the ribcage mechanism. An ablation mechanism may include an active electrode assembly disposed along a first side of the inner recess of the ribcage mechanism, and a return electrode assembly disposed along a second side of the inner recess of the stabilizer. In some instances, the flexible stabilizer mechanism can be configured to deliver suction to a portion of the patient tissue, so as to draw the portion of the patient tissue into the inner recess of the ribcage mechanism, and between the active electrode assembly and the return electrode assembly.

In yet another aspect, embodiments of the present invention encompass methods for administering an ablation treatment to a patient tissue. Exemplary methods may include placing a treatment assembly near the tissue of the patient. A treatment assembly may include a flexible stabilizer mechanism having an inner recess, a ribcage mechanism disposed at least partially within the inner recess of the stabilizer mechanism, the ribcage mechanism having an inner recess, and an ablation mechanism coupled with the ribcage mechanism, the ablation mechanism comprising an active electrode assembly disposed along a first side of the inner recess of the ribcage mechanism and a return electrode assembly disposed along a second side of the inner recess of the stabilizer. Methods may also include delivering a vacuum through the stabilizer mechanism so as to draw a portion of the patient tissue into the inner recess of the ribcage mechanism, and between the active electrode assembly and the return electrode assembly. Further, methods may include administering a bipolar ablation to the tissue via the ablation mechanism to create a lesion in the tissue.

In another aspect, embodiments of the present invention encompass surgical systems for administering an ablation treatment to a patient tissue. Exemplary surgical systems may include a flexible stabilizer mechanism having a pod assembly housing a ribcage mechanism that defines an inner recess, and an ablation mechanism coupled with the ribcage mechanism. The ablation mechanism may include an electrode assembly disposed along a first side of the inner recess of the ribcage mechanism, and a return electrode assembly disposed along a second side of the inner recess of the ribcage mechanism. In some instances, the flexible stabilizer mechanism can be configured to deliver suction to a portion of the patient tissue, so as to draw the portion of the patient tissue into the inner recess of the ribcage mechanism, and between the active electrode assembly and the return electrode assembly.

In another aspect, embodiments of the present invention encompass methods for administering an ablation treatment to a patient tissue. Exemplary methods may include placing a treatment assembly near the tissue of the patient. The treatment assembly may include a flexible stabilizer mechanism having a pod assembly housing a ribcage mechanism that defines an inner recess, and an ablation mechanism coupled with the ribcage mechanism. The ablation mechanism may include an electrode assembly disposed along a first side of the inner recess of the ribcage mechanism and a return electrode assembly disposed along a second side of the inner recess of the ribcage mechanism. Methods may also include delivering a vacuum through the stabilizer mechanism so as to draw a portion of the patient tissue into the inner recess of the ribcage mechanism, and between the active electrode assembly and the return electrode assembly. Further, methods may include administering a bipolar ablation to the tissue via the ablation mechanism to create a lesion in the tissue.

In still a further aspect, embodiments of the present invention encompass surgical systems or treatment assemblies for administering an ablation treatment to a patient tissue. Exemplary surgical systems or treatment assemblies may include a flexible stabilizer mechanism defining an inner recess, and a ribcage mechanism disposed within the inner recess of the stabilizer mechanism. The ribcage mechanism can define an inner recess. Surgical systems or treatment assemblies may also include an electrode mechanism disposed within the inner recess of the ribcage mechanism. The electrode mechanism can define an inner recess for receiving a portion of the tissue for administration of a monopolar ablation treatment. In some instances, the flexible stabilizer mechanism is configured to deliver suction through the ribcage mechanism, so as to draw the portion of the patient tissue into the inner recess of the electrode mechanism.

In another aspect, embodiments of the present invention encompass methods for administering an ablation treatment to a patient tissue. Exemplary methods may include placing a treatment assembly near the tissue of the patient. A treatment assembly may include a flexible stabilizer mechanism defining an inner recess, a ribcage mechanism disposed within the inner recess of the stabilizer mechanism and defining an inner recess, and an electrode mechanism disposed within the inner recess of the ribcage mechanism and defining an inner recess. Methods may also include delivering a vacuum through the stabilizer mechanism and through the ribcage mechanism so as to draw a portion of the patient tissue into the inner recess of the electrode mechanism. Further, methods may include administering a monopolar ablation to the tissue via the electrode mechanism to create a lesion in the tissue.

In yet another aspect, embodiments of the present invention encompass surgical systems for administering an ablation treatment to a patient tissue. Exemplary systems may include a flexible stabilizer mechanism having a pod assembly housing a ribcage mechanism that defines an inner recess. Systems may also include an electrode assembly disposed within the inner recess of the ribcage mechanism. An electrode assembly may define an inner recess configured to receive a portion of the patient tissue and configured to transmit a monopolar ablation treatment to the tissue portion. In some instances, a flexible stabilizer mechanism can be configured to deliver suction to the portion of the patient tissue, so as to draw the portion of the patient tissue into the inner recess of the electrode mechanism.

In still yet another aspect, embodiments of the present invention encompass methods for administering an ablation treatment to a patient tissue. Exemplary methods may include placing a treatment assembly near the tissue of the patient. The treatment assembly may include an electrode mechanism having an inner recess, a ribcage mechanism having an inner recess housing the electrode mechanism, and a flexible stabilizer mechanism having an inner recess housing the ribcage mechanism. Methods may also include delivering a vacuum through the stabilizer mechanism, the ribcage mechanism, and the electrode mechanism, so as to draw a portion of the patient tissue into the inner recess of the electrode mechanism. Further, methods may include administering a monopolar ablation to the tissue via the electrode mechanism to create a lesion in the tissue.

In another aspect, embodiments of the present invention encompass systems for administering an ablation treatment to a patient tissue. Exemplary systems may include a stabilizer mechanism having an inner recess, and an ablation mechanism disposed within the inner recess of the stabilizer mechanism. The ablation mechanism may include a first electrode side and a second electrode side opposing the first electrode side, the ablation mechanism configured to receive a portion of the tissue between the first electrode side and the second electrode side. In some instances, the stabilizer mechanism includes a pod assembly coupled with a ribcage mechanism. In some instances, the ablation mechanism includes a ribcage mechanism coupled with an electrode mechanism.

In still a further aspect, embodiments of the present invention encompass methods for administering an ablation treatment to a patient tissue. Exemplary methods may include placing a treatment assembly near the tissue of the patient. The treatment assembly may include a stabilizer mechanism having an inner recess, and an ablation mechanism disposed within the inner recess of the stabilizer mechanism. The ablation mechanism can have a first electrode side and a second electrode side opposing the first electrode side. Methods may also include delivering a vacuum through the stabilizer mechanism so as to draw a portion of the patient tissue into the inner recess of the stabilizer mechanism, and between the first electrode side and a second electrode side. Further, methods may include administering an ablation protocol to the tissue via the ablation mechanism to ablate the tissue portion.

In some instances, the stabilizer mechanism includes a pod assembly coupled with a ribcage mechanism. In some instances, the ablation mechanism includes a ribcage mechanism coupled with an electrode mechanism. In some instances, the ablation protocol includes administration of a bipolar ablation. In some instances, the ablation protocol includes administration of a monopolar ablation. In some instances, the ablation protocol includes administration of a bipolar ablation and a monopolar ablation.

In one aspect, embodiments of the present invention encompass surgical systems for administering a lesion forming treatment to a patient tissue. Exemplary systems may include a flexible stabilizer mechanism defining an inner recess, a ribcage mechanism disposed within the inner recess of the stabilizer mechanism, the ribcage mechanism defining an inner recess, and a lesion forming mechanism disposed within the inner recess defined by the ribcage mechanism. The inner recess of the ribcage mechanism can be configured to receive a portion of the tissue for administration of a lesion forming treatment. In some cases, the lesion forming mechanism includes a bipolar radiofrequency energy ablation mechanism, a monopolar radiofrequency energy ablation mechanism, a high voltage pulse mechanism, a microwave energy mechanism, an infrared laser mechanism, a cryo-thermal mechanism, an ultrasound ablation mechanism, a chemical ablation mechanism, or a radiation mechanism. In some cases, the flexible stabilizer mechanism is configured to deliver suction to a portion of the patient tissue, so as to draw the portion of the patient tissue into the inner recess defined by the ribcage mechanism, and into proximity with the lesion forming mechanism. In some cases, the stabilizer mechanism includes or defines a pocket that channels a vacuum delivered by the stabilizer mechanism. In some cases, a system also includes a temperature sensor disposed along a central portion of the stabilizer mechanism inner recess. Optionally, the system may also include a cinching mechanism configured to constrict the lesion forming mechanism about the patient tissue. In some cases, the stabilizer mechanism includes a pod assembly coupled with a ribcage mechanism.

In another aspect, embodiments of the present invention encompass methods for administering a lesion forming treatment to a patient tissue. Exemplary methods may include placing a treatment assembly near the tissue of the patient, where the treatment assembly includes a flexible stabilizer mechanism defining an inner recess, a ribcage mechanism disposed within the inner recess of the stabilizer mechanism and defining an inner recess, and a lesion forming mechanism disposed within the inner recess defined by the ribcage mechanism. Methods may also include delivering a vacuum through the stabilizer mechanism and through the ribcage mechanism so as to draw a portion of the patient tissue into the inner recess defined by the ribcage mechanism. Further, methods may include administering the lesion forming treatment to the tissue via the lesion forming mechanism to create a lesion in the tissue. In some cases, the lesion forming mechanism includes a bipolar radiofrequency energy ablation mechanism, a monopolar radiofrequency energy ablation mechanism, a high voltage pulse mechanism, a microwave energy mechanism, an infrared laser mechanism, a cryo-thermal mechanism, an ultrasound ablation mechanism, a chemical ablation mechanism, or a radiation mechanism. In some cases, the stabilizer mechanism includes or defines a pocket that channels the vacuum delivered through the stabilizer mechanism.

In another aspect, embodiments of the present invention encompass surgical systems for administering a lesion forming treatment to a patient tissue. Exemplary systems may include a suction mechanism defining an inner recess, and a lesion forming mechanism disposed within the inner recess defined by the suction mechanism. The suction mechanism is reinforced to resist collapse when a vacuum is present within the inner recess. The inner recess is configured to receive a curvilinear portion of the tissue for administration of the lesion forming treatment thereto. In some instances, the curvilinear portion of patient tissue includes a section having a thickness T, and wherein the inner recess defined by the suction mechanism is configured to receive the section therein, such that the section extends into the inner recess at a distance of greater than 0.5 T. In some instances, the suction mechanism includes a pod assembly housing a ribcage mechanism, and the ribcage mechanism operates to reinforce the suction mechanism so that the suction mechanism resists collapse when a vacuum is present within the inner recess. In some instances, the suction mechanism is configured to deliver suction to a portion of the patient tissue, so as to draw the portion of the patient tissue into an inner recess defined by the ribcage mechanism, and into proximity with the lesion forming mechanism. In some instances, the lesion forming mechanism includes a bipolar radiofrequency energy ablation mechanism, a monopolar radiofrequency energy ablation mechanism, a high voltage pulse mechanism, a microwave energy mechanism, an infrared laser mechanism, a cryo-thermal mechanism, an ultrasound ablation mechanism, a chemical ablation mechanism, or a radiation mechanism. In some instances, the lesion forming mechanism includes a ribcage mechanism, and the ribcage mechanism operates to reinforce the suction mechanism so that the suction mechanism resists collapse when a vacuum is present within the inner recess. Optionally, the suction mechanism may include or define a pocket that channels a vacuum delivered by the suction mechanism. In some cases, a system may also include a temperature sensor disposed along a central portion of the inner recess. In some cases, a suction mechanism may include or define a cooling lumen. In some cases, a suction mechanism may include or define an irrigation lumen.

In a further aspect, embodiments of the present invention encompass surgical systems for administering a lesion forming treatment to a patient tissue. Exemplary surgical systems may include a stabilizer mechanism defining an inner recess, and a lesion forming mechanism disposed within the inner recess of the stabilizer mechanism. In some cases, the stabilizer mechanism includes a pod assembly housing a ribcage mechanism. In some cases, the ribcage mechanism defines an inner recess configured to receive a portion of the patient tissue, and the lesion forming mechanism is disposed within the inner recess defined by the ribcage mechanism. In some cases, the lesion forming mechanism is configured to transmit the lesion forming treatment to the portion of the patient tissue. In some cases, the flexible stabilizer mechanism is configured to deliver suction to a portion of the patient tissue, so as to draw the portion of the patient tissue into an inner recess defined by the ribcage mechanism, and into proximity with the lesion forming mechanism. In some cases, the lesion forming mechanism includes a ribcage mechanism. In some cases, the lesion forming mechanism includes a bipolar radiofrequency energy ablation mechanism, a monopolar radiofrequency energy ablation mechanism, a high voltage pulse mechanism, a microwave energy mechanism, an infrared laser mechanism, a cryo-thermal mechanism, an ultrasound ablation mechanism, a chemical ablation mechanism, or a radiation mechanism. In some cases, the stabilizer mechanism includes or defines a pocket that channels a vacuum delivered by the stabilizer mechanism. In some cases, a surgical system may also include a temperature sensor disposed along a central portion of the ribcage mechanism inner recess. In some cases, a stabilizer mechanism may include or define a cooling lumen. In some cases, a stabilizer mechanism may include or define an irrigation lumen The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this Summary. This Summary is a high-level overview of various aspects of the invention and introduces some of the concepts that are further described in the Detailed Description section below. This Summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The above described and many other features and attendant advantages of embodiments of the present invention will become apparent and further understood by reference to the following detailed description when considered in conjunction with the accompanying drawings.

BRIEF DESCRIPTION OF THE DRAWINGS

Illustrative embodiments of the present invention are described in detail below with reference to the following drawing figures.

FIGS. 1A to 1M show aspects of surgical systems and methods according to embodiments of the present invention.

FIGS. 3A to 3E show aspects of surgical systems and methods according to embodiments of the present invention.

FIGS. 12, 12A, and 12B show aspects of surgical systems and methods according to embodiments of the present invention.

FIGS. 15, 15A, 15B, 15C-1, 15C-2, 15C-3, 15D-1, 15D-2, 15D-3, 15E-1, 15E-2, and 15E-3 show aspects of surgical systems and methods according to embodiments of the present invention.

FIG. 22 shows aspects of surgical systems and methods according to embodiments of the present invention.

DETAILED DESCRIPTION OF THE INVENTION

Figure 1A:
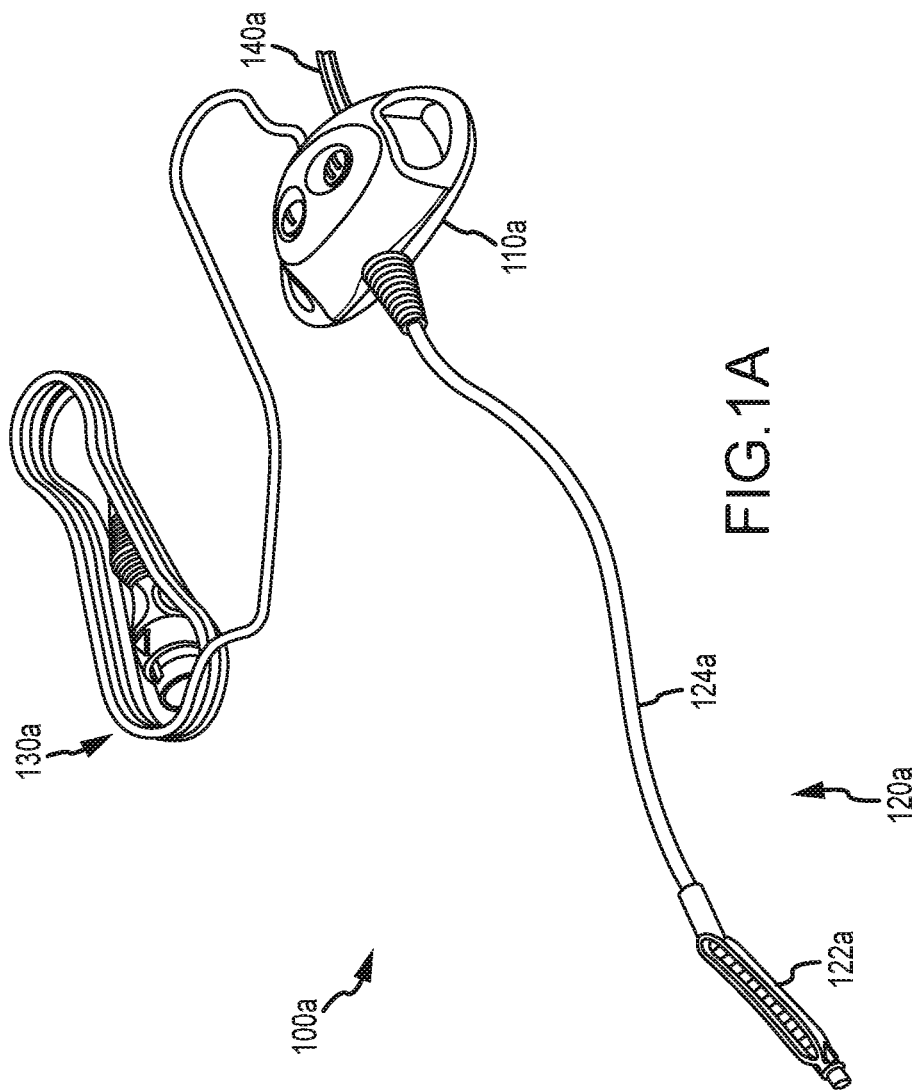

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Embodiments of the present invention encompass systems and methods for the ablation of patient tissue or the formation of one or more lesions therein. As such, exemplary techniques may employ any of a variety of lesion forming means, including bipolar radiofrequency energy ablation mechanisms, monopolar radiofrequency energy ablation mechanisms, high voltage pulse mechanisms, microwave energy mechanisms, infrared laser mechanisms, cryo-thermal mechanisms, ultrasound ablation mechanisms, chemical ablation mechanisms, and radiation mechanisms. Exemplary surgical systems can be employed during a treatment or procedure through any of a variety of surgical access modalities, including without limitation sternotomy, thoracotomy, port access, subxiphoid, and the like. According to some embodiments, a treatment method may include ablating and monitoring a cardiac tissue of a patient with a tissue treatment system. Treatment methods may also include techniques for placing a tissue treatment system at a desired location within a patient. For example, a treatment method may include positioning a tissue treatment system at or near the pulmonary veins of a patient. A surgeon or operator may use an obturator and introducer assembly to posit the tissue treatment system at or near a specific location or anatomical feature of the patient. A treatment assembly or system can include any of a variety of tissue ablation mechanisms. In some cases, a treatment assembly can include an ablation element that transmits or delivers RF energy to patient tissue. Optionally, suitable ablation elements can transmit or deliver infrared laser energy, high intensity focused ultrasound (HIFU) energy, microwave energy, cryoablation energy, high-voltage pulses to ablate tissue by electroporation, and the like. Embodiments encompass treatment assemblies having multiple ablation elements, such as RF electrodes. In some cases, an treatment assembly may include a single ablation element, such as a single RF ablation electrode. Typically, an RF electrode is activated in its entirety during an ablation procedure. Longer lesion lengths can be made by moving the electrode and ablating so that the ablations from the two ablation applications overlap. The procedure can be repeated until the desired lesion pattern is completed.

In some instances, systems provide a bipolar ablation device configured either as a short segment device or a long belt device. Such bipolar ablation devices can operate to produce a true bipolar transmural lesion, such that current is transmitted from one tissue surface to an opposing tissue surface, across the entire thickness of the tissue. Surgical systems as disclosed herein are well suited for use in producing linear lesions or encircling lesions that circumscribe tissue structures, such as one or more pulmonary veins. Ablation mechanisms can be configured so that some elements, for example a first electrode assembly, can operate to deliver RF energy and other elements, such as a second electrode assembly, can operate to provide a return path for the RF energy. The first and second electrode assemblies can be directly opposed to one another at opposite sides of a suction pod. For example, active and return electrode assemblies can be mounted on opposing sides of an inner recess or concave surface of a suction pod. Patient tissue, such as a portion of the atrial wall, can be drawn into the vacuum pod and sandwiched between the active and return electrodes. The suction pod causes the tissue to fold at least partially; reducing the effect of heat sink on target tissue or to fold fully to cause complete endocardial tissue apposition. In this way, any of the monopolar or bipolar ablation protocols can be applied to the patient tissue.

Any of a variety of electrode configuration design and arrays can be used for ablating tissue with RF thermal ablation or for delivering high-voltage pulses to the tissue to induce irreversible electroporation. For example, surgical systems may include planar electrodes, cylindrical helical electrodes, linear wire, cable, or strip type electrodes, flat electrodes, and the like. Exemplary techniques for delivering high-voltage pulse treatments to patient tissue are described in U.S. patent application Ser. No. 13/149,687 filed May 31, 2011, the content of which is incorporated herein by reference. Systems can include any desired number of active and return electrodes. For example, systems may include 6 to 7 active electrodes and 1 to 2 return electrodes. Exemplary systems can be configured to delivery various types of regulated energy, for example, RF energy which is controlled by maintaining a set tissue temperature. Temperature sensors can be placed at multiple locations along the length and cross-section of the device, for example in close contact with one or more active ablating electrodes. Temperature sensors can also be placed along the center line or central portion of the roof of the suction stabilizer to provide an indication of temperature at the tissue center away from ablation. In some embodiments, a treatment system may include a cinching mechanism to allow the circumference of the suction stabilizer to be adjustable to the tissue structure to be treated. A cinching mechanism may be facilitated by fixing a distal section of the suction stabilizer and retracting a proximal section of the suction stabilizer, or by a separate mechanism that cinches both distal and proximal sections.

A linear array can also be achieved with the same or a different device configured in various lengths. By withdrawing the probe into a housing so that only the distal portion of the electrode is exposed, the same device may be used to achieve bipolar pacing with a suction applicator to ensure tissue contact. Alternatively, distal leads can be wired or electrically coupled with the distal end of the device and terminate in different pins distinct from the RF wiring of the distal electrodes. A pacing function can be performed by an ablation generator. Alternatively, an adaptor connector can be configured as identical to a female connection of an ablation generator for insertion of the probe cable with positive and negative male pins compatible with an external pacemaker for subsequent suction applied pacing following an ablation procedure. Belt devices may include visualization and delivery systems, including without limitation, scopes with protective lenses and introducers with stylets, sheaths, or magnets, or combinations thereof. Belt devices can also include a marking system for identifying to the user which electrodes are or are not in contact with tissue for ablation.

Figure 1B:
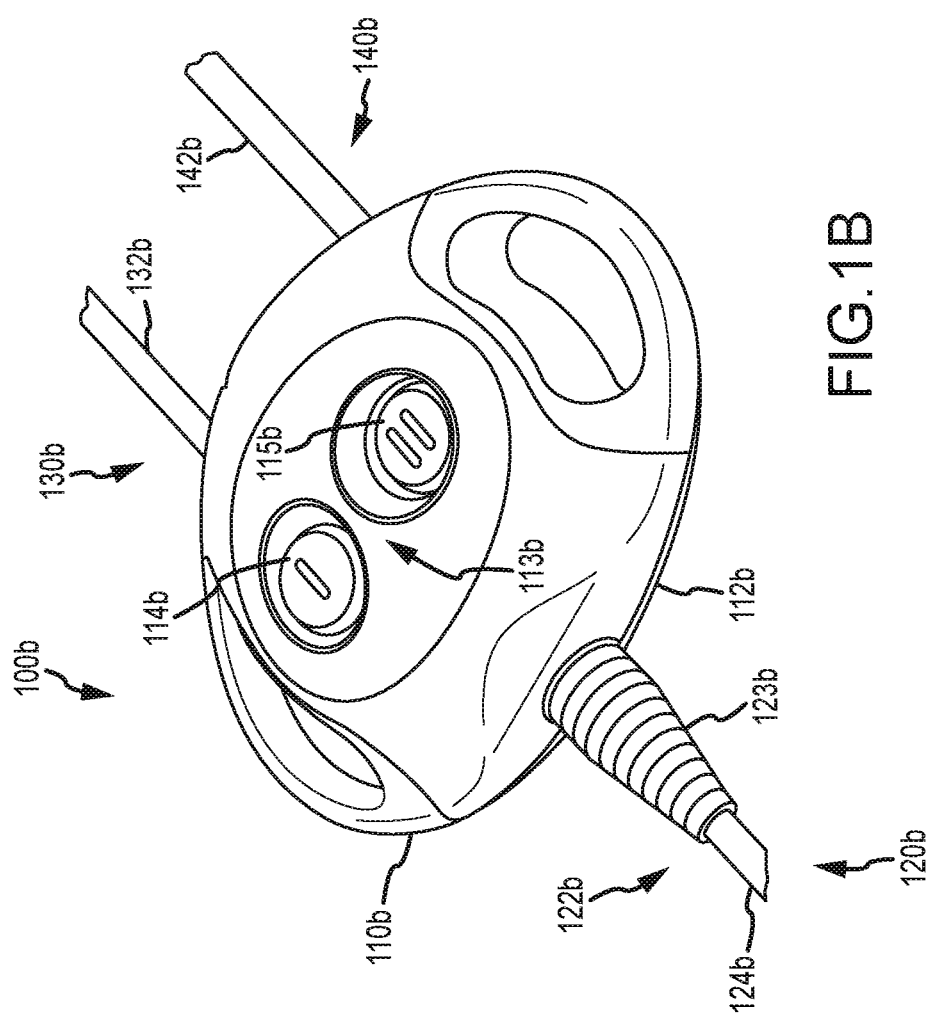

Turning now to the drawings, FIG. 1A illustrates aspects of a tissue surgical system 100a according to embodiments of the present invention. As shown here, surgical system 100a includes a handle mechanism 110a, an ablation assembly or ablation probe mechanism 120a, a power coupling assembly 130a that connects with a power source such as an electrosurgical unit (ESU), and a suction coupling assembly 140a that connects with a vacuum source. Ablation assembly 120a includes a distally positioned probe assembly 122a and a proximally positioned probe tubing assembly 124a. FIG. 1B shows additional aspects of surgical system 100b according to embodiments of the present invention. As depicted here, handle mechanism 110b may include or be in operational association with a probe tubing assembly 122b, a power coupling assembly 130b having a cable 132b that provides connectivity with an ESU, and a suction coupling assembly 140b having a suction tubing 142b. Probe tubing assembly 122b may include a strain-relieved swivel 123b that allows a grip assembly 112b of the handle to remain flat without influencing axial rotation of the tubing 124b, and a braided tube construction to flexibly transmit torque, probe power, temperature sensing, and suction, between various components of the surgical system.

The handle also contains a switching mechanism 113b for the user to select between monopolar and bipolar modes. As shown here, the switching mechanism 113b includes a monopolar button 114b and a bipolar button 115b. The buttons which actuate the switching mechanism have numerous features to enhance user feedback to help the user to differentiate and recognize quickly which mode the device is in, such as lighted buttons (e.g. 114b, 115b) that turn on when pushed, indicating that current is available to the circuit for the chosen mode. The handle is also shaped to minimize tubing snagging in the sterile field and is shaped to prevent accidental mode switching. For example, buttons 114b, 115b may be recessed within the body of the handle mechanism.

FIG. 1C illustrates further features of an ablation assembly 120c according to embodiments of the present invention. As shown here, ablation assembly 120c includes a suction stabilizer or pod mechanism 123c, one or more grab tabs 124c, a magnet assembly 125c located at a distal position on the ablation assembly, and a flexible proximal end 126c that provides a U-joint connection with an elongate member or tubing of the ablation assembly. Stabilizer mechanism 123c defines a suction zone 127c, which may contain or house electrodes or energy transmission members. In use, an operator may use an introducer or other attachment means for coupling with magnet assembly 125c, so as to allow the operator to maneuver the ablation assembly as desired. For example, the operator may employ attachment, grasping, positioning, or introducer systems and navigation techniques such as those described in U.S. Ser. No. 12/124,743 filed May 21, 2008, U.S. Ser. No. 12/124,766 filed May 21, 2008, U.S. Ser. No. 12/339,331 filed Dec. 19, 2008, and U.S. Ser. No. 12/879,106 filed Sep. 10, 2010, the contents of each of which are incorporated herein by reference. In some instances, a grasping instrument with a magnetic distal section can be used to magnetically couple with the ablation or probe assembly 120c. The grasping instrument can then be used to introduce, retrieve, or otherwise manipulate, maneuver, or position the ablation probe assembly 120c as desired. A grasping means 124c on the ablation probe assembly may include flat, round, and/or toothed zones, and can also include multiple grab tabs or fins for grasping with forceps or a similar instrument. Such features of a grasping means 124c may allow freedom of grasping angles while maintaining control over bending and torsion of the ablation probe assembly 120c. In some instances, a distal section 121c of the ablation probe assembly 120c may include any of a variety of shapes, in addition to or in place of grab tabs 124c and/or magnet assembly 125c, that can be grasped or coupled with an introducer assembly or other positioning device for maneuvering the ablation assembly. For example, distal section 121c may present ball shaped features, optionally with a neck, tabs with orientation features, keyhole slots, flat with grip ribs, and the like.

Figure 1D:
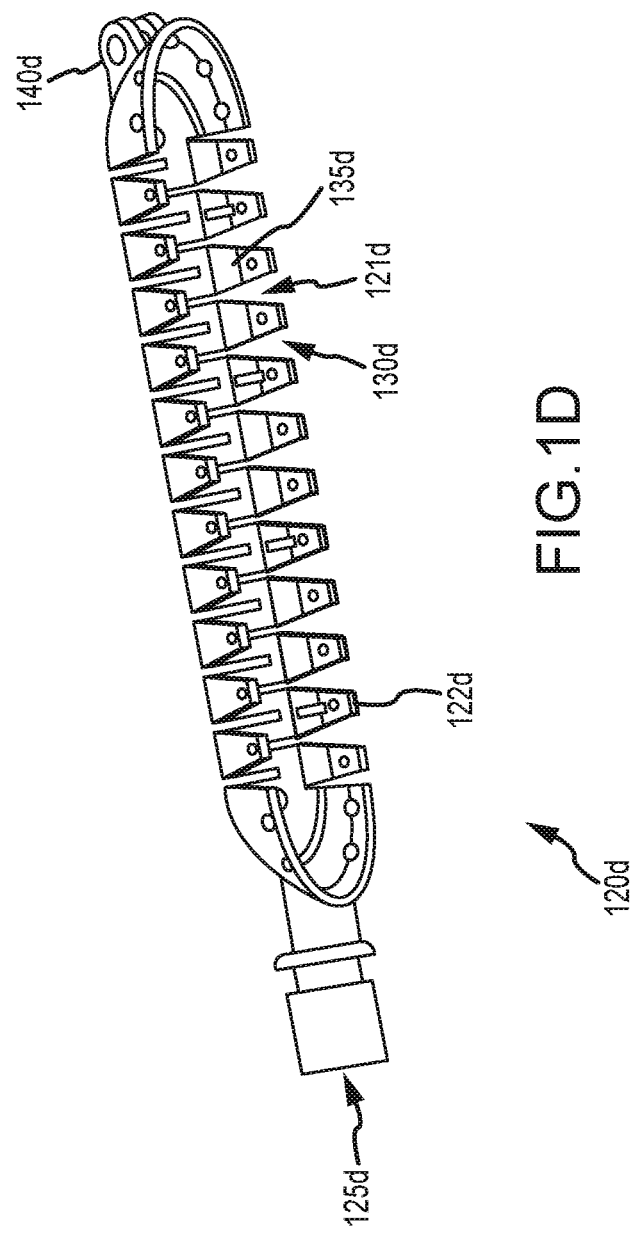

FIG. 1D depicts exemplary features of an ablation assembly 120d according to embodiments of the present invention. As shown here in an exemplary embodiment, ablation assembly 120d includes a magnet assembly 125d, a ribcage mechanism 130d having a flexible spine and rib configuration with electrode surfaces 135d, and a proximal U-joint connection 140d. In some embodiments, an ablation assembly may include a suction stabilizer and a ribcage as separate element. In some embodiments, an ablation assembly may include a suction stabilizer and a ribcage as a unified structure. Such a unified structure may be rigid or flexible. Further, such a separated or unified structure may be mechanically actuated in any of a variety of active or passive ways. For example, an ablation assembly, optionally in combination with a pod assembly, can be actuated by an external mechanism such as a clamp, by an internal mechanism contained within the probe assembly, or by either positive or negative pressure, such that moving parts of the ablation assembly or probe assembly are actuated. For example a tube or plurality of tubes may deliver either suction or pressure, in gas or liquid form, to the ablation assembly or probe assembly, such that the pressure differential across the structural chambers, recesses, partitions, or actuation mechanism causes movement or applies a force. In this way, the ablation assembly or probe assembly can squeeze tissue, open up space for tissue to enter, move electrodes into functional position, move the ribcage and/or suction pod into a shape, in cross section or into a curvature or shape down the length of the assembly, in order to access the tissue site or create a lesion. Still further, such as unified structure may include multiple rigid segments jointed together. In some cases, embodiments may involve a separate suction stabilizer and ribcage, and the ribcage may also be rigid or flexible. Relatedly, such a ribcage may be actuated in any of a variety of active or passive ways as described elsewhere herein. Still further, such a ribcage may be constructed of rigid segments jointed together. In use, the ribcage mechanism 130d can operate to prevent or inhibit the collapse of a suction pod mechanism (not shown) when a vacuum is applied therein. The ribcage mechanism 130d can also provide a degree of flexibility for electrodes attached therewith, to enhance or facilitate contact between the electrodes and the patient tissue. By presenting a series of ribs with intervening spaces, the ribcage mechanism can also function as a screen, thus allowing suction supplied from a vacuum source to pass through the intervening spaces and to reach the patient tissue.

Figure 1E:
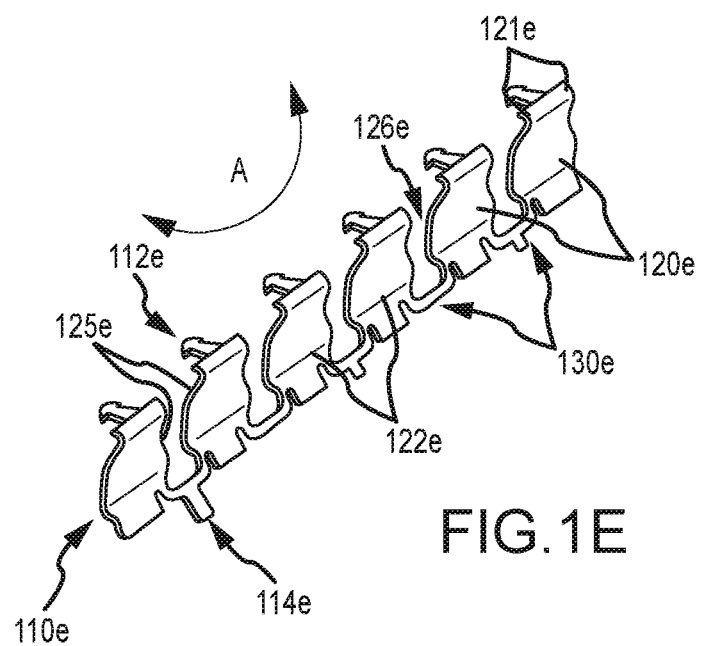
Figure 13:
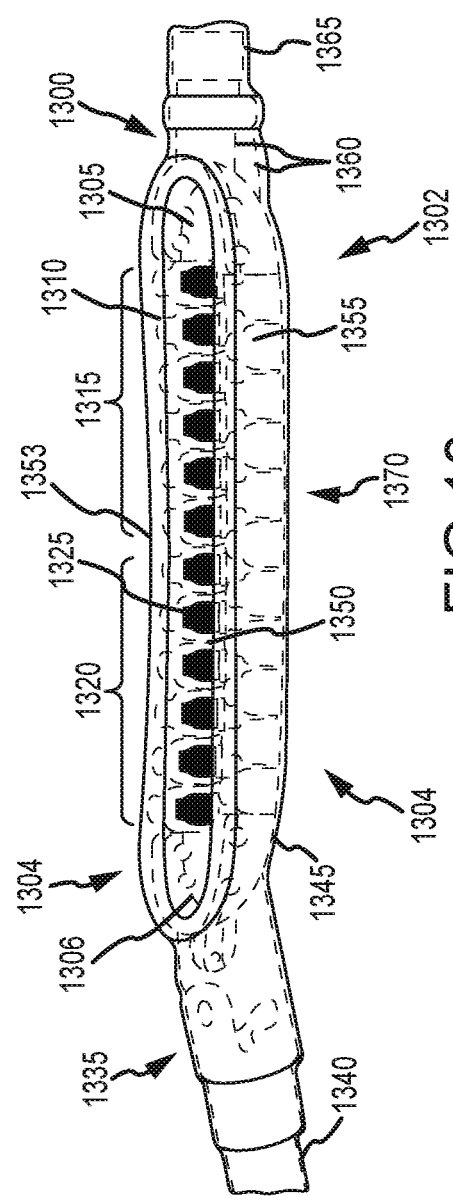
FIGS. 13 and 13A show aspects of surgical systems and methods according to embodiments of the present invention.
Figure 14:
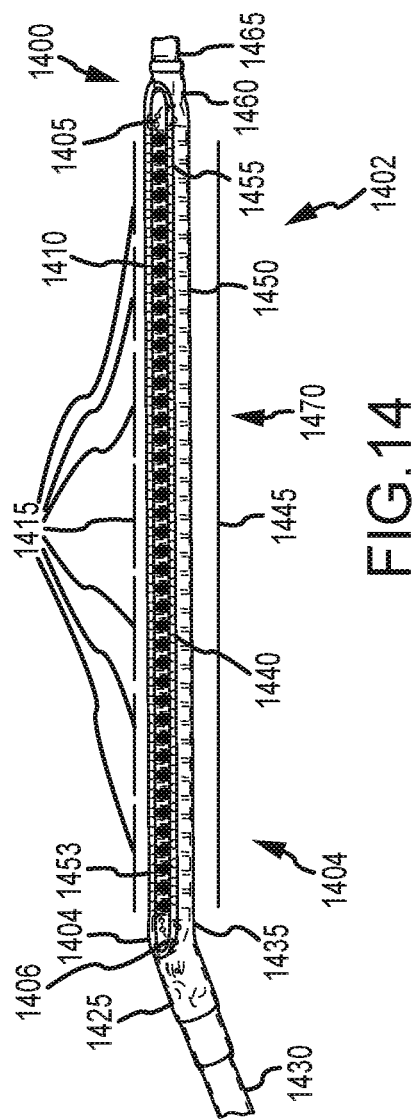
FIG. 14 shows aspects of surgical systems and methods according to embodiments of the present invention.

Surgical systems and methods for administering an ablation or lesion forming treatment to a patient tissue as described herein often involve a flexible stabilizer mechanism, a ribcage mechanism or reinforcement member, and an ablation or lesion forming mechanism. In some cases, the ablation assembly or lesion forming mechanism may include a bipolar radiofrequency energy ablation mechanism, a monopolar radiofrequency energy ablation mechanism, a high voltage pulse mechanism, a microwave energy mechanism, an infrared laser mechanism, a cryo-thermal mechanism, an ultrasound ablation mechanism, a chemical ablation mechanism, a radiation mechanism, or the like. As discussed elsewhere herein, lesion forming systems may include one or more electrodes. FIG. 1E shows an electrode mechanism 110e of an ablation assembly according to embodiments of the present invention. In some embodiments, an ablative element may present a cylindrical cross-section and be in the form of a microwave antenna, a light diffusing optical fiber, or an ablation electrode. In some embodiments, an ablation electrode may be flat and straight or flat and two dimensionally curved to conform to the tissue or to cause the tissue to take a particular shape within the suction recess or cavity that enhances transmural lesion creation. As shown here, an electrode mechanism may include distal barbs or coupling mechanisms 112e and proximal tabs 114e for coupling with a ribcage mechanism or other ablation assembly components as shown in FIG. 1H. As shown in FIG. 1E, electrode mechanism 110e includes certain features that confer flexibility to the electrode, and allow the electrode to maintain apposition to ribs of a ribcage mechanism during the administration of a treatment procedure. For example, the electrode includes a set of individual plates 120e connected by intervening junctions 130e. Plates 120e may be curved or contoured, for example as shown here presenting a concave surface, which can enhance contact or engagement with patient tissue during use. Junctions 130e may be constructed of thin or flexible wires or connector portions (e.g. having a small diameter or cross-section), which facilitate the flexibility of the electrode mechanism 110e in any three dimensional direction (e.g. along any x, y, z coordinate), and also facilitate twisting or torsional flexibility of the electrode mechanism about a longitudinal axis. As shown here, a first or upper portion 121e of a plate 120e may be narrower than a second or lower portion 122e of plate 120e, so that when the electrode is bent in-plane in a curve as indicated by arrow A, an enhanced range of motion is achieved, until edges 125e contact one another or other mechanical interference within the electrode prevents further bending. According to some embodiments, portions of a suction pod mechanism, which may include or be constructed of a flexible material such as silicone rubber, may extend into spaces 126e (e.g. intercostal spacings or gaps) between individual plates or tines 120e. With continued reference to FIG. 1E, plates 120e can be shaped or contoured so as to contact the tissue with a desired shape and surface area for delivering energy to the tissue or receiving energy from the tissue. Junctions 130e can connect plates 120e together as a group or string, mechanically and/or electrically, so as to provide one continuous electrode. Junctions 130e can be shaped with a small cross-section, curvature, and relatively long length in order to allow flexibility between adjacent plates 120e. The electrode mechanism 110e shown here is well suited for use in a bipolar ablation approach to thermally heat tissue with RF ablation or to apply high-voltage pulses to ablate tissue with an irreversible electroporation technique, wherein a probe assembly may include two or more of such electrode mechanisms. For example, a probe assembly may include one electrode mechanism on one side of a ribcage mechanism, and another electrode mechanism on an opposing side of the ribcage mechanism, as discussed elsewhere herein. In some cases, a probe assembly may include multiple mechanisms along a side of a ribcage mechanism. For example, an ablation assembly as depicted in FIG. 13 may include a set of two active electrode mechanisms along one side of a ribcage mechanism. Relatedly, an ablation assembly as depicted in FIG. 14 may include a set of seven active electrode mechanisms along one side of a ribcage mechanism.

Figure 1F:
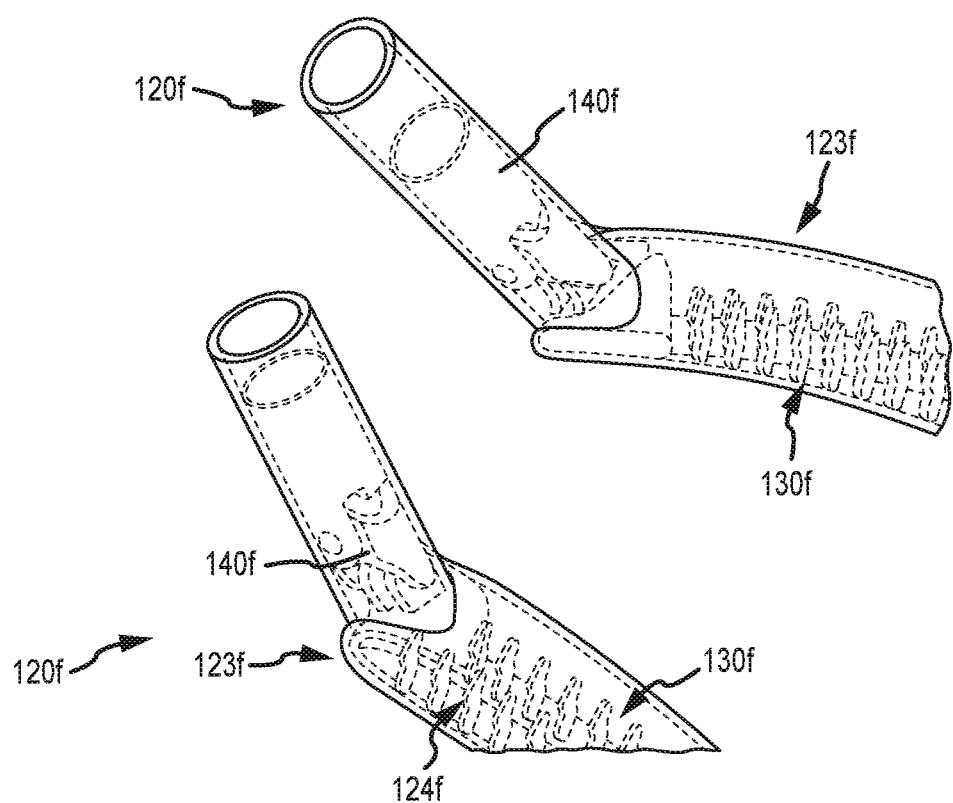
Figure 1G:
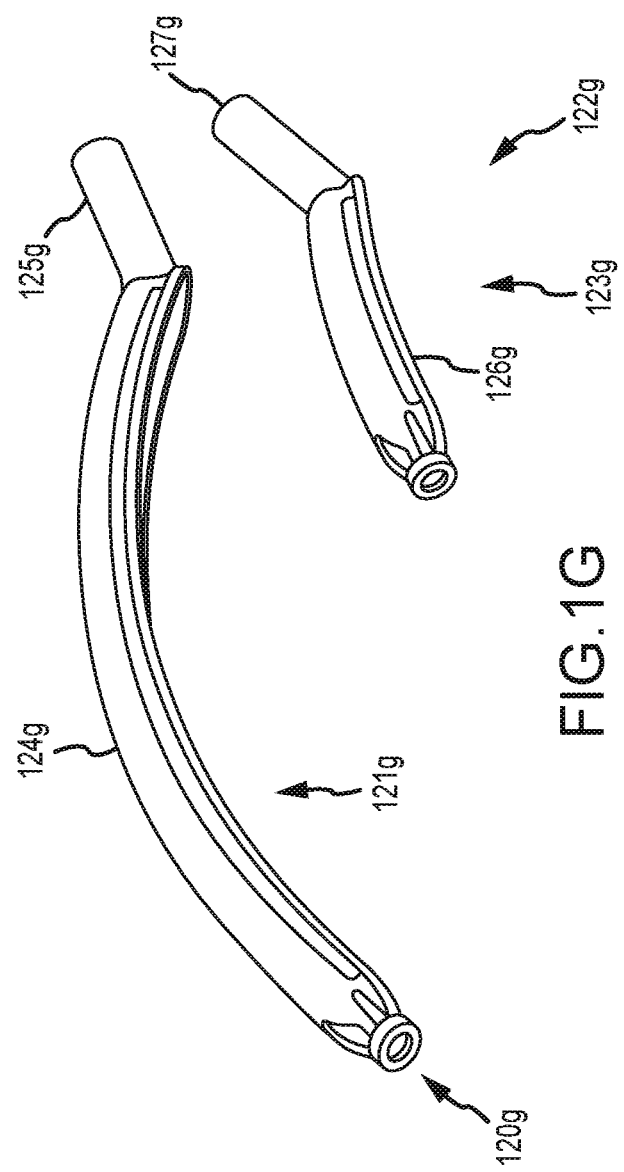

FIG. 1F shows aspects of an ablation assembly 120f having a suction pod mechanism 123f (depicted transparently, here), a ribcage mechanism 130f disposed in the suction pod mechanism 123f, and a U-joint assembly 140f. In use, a suction recess or cavity 124f defined by the suction pod mechanism 123f can operate to allow suction or negative pressure to draw tissue into the recess, and against or toward one or more electrodes of the ablation mechanism. As shown in FIG. 1G, an ablation assembly may have a suction pod mechanism defining suction zones in various sizes. For example, ablation assembly configuration 120g presents a longer suction pod assembly 121g, and ablation assembly configuration 122g presents a shorter suction pod assembly 123g. As shown here, ablation assembly 120g includes a long probe assembly 124g and a probe tubing assembly 125g. Similarly, ablation assembly 122g includes a short probe assembly 126g and a probe tubing assembly 127g.

FIG. 1H depicts exemplary features of an ablation assembly 120h according to embodiments of the present invention. As shown here, ablation assembly 120h includes a magnet assembly 125h, a ribcage mechanism 130h having a flexible spine and rib configuration, an electrode mechanism 135h coupled with the ribcage mechanism 130h, and a U-joint connection 140h. As shown here, a probe assembly may include the ribcage and electrode assemblies, and a probe tubing assembly may include elongate element 150h which is coupled to the ribcage mechanism by a coupling mechanism 160h. Elongate element 150h and coupling mechanism 160h can facilitate the transmission of a vacuum to the ribcage mechanism 130h, for example when elongate element 150h and coupling mechanism 160h are disposed within a tubing (not shown) that is in fluid communication with a suction pod (not shown) disposed about the ribcage mechanism. The U-joint allows flexibility in all axes of bending at the probe tube connection to the probe (as indicated by arrows A and B), allowing the positioning of the probe into tight anatomical corners and pockets, maintaining suction and electrical connections from probe to handle, all the while allowing transmission of torque to control the axial rotation of the probe from the external aspect of the probe tubing. The system also includes a suction pod or suction mechanism, such as those shown in FIG. 1C, 1F, or 1G, which covers or houses the ribcage mechanism. In use, the sidewalls of the ribcage mechanism 130h are flexible, and can conform with a variety of tissue thicknesses.

According to some embodiments, the ribs or opposing walls of the ribcage mechanism are semi-rigid, so as to provide some degree of flex in response to tissue and some degree of rigidity in response to suction. For example, the semi-rigid side walls or ribs can flex so as to facilitate the ingress of thicker tissue by spreading wider as the tissue moves between the side walls or opposing ribs and into the chamber. Relatedly, the semi-rigid side walls or ribs can resist excessive flex so as to avoid collapse either outwardly or inwardly when suction is administered through the suction pod and to the patient tissue.

In some instances, the suction pod, ribcage, and electrodes move together in unison, with the suction pod in contact with ribcage, and the ribcage in contact with electrodes. Various types of movement or flexing may affect interactions between these ablation assembly components. Similarly, use of the ablation assembly with tissues of varying thickness may also affect interactions between these ablation assembly components.

According to some embodiments, the entire probe (e.g. suction pod, ribcage, and electrodes) can flex up and down, flex side to side, and twist in either direction (i.e. levorotation and dextrorotation), either alone or in any combination thereof. Such flexibility can be conferred at least in part by a ribcage mechanism having a serpentine spine construction with spacings between rib that change to accommodate such movement, by a suction pod mechanism constructed of a material that stretches and compresses, and by one or more electrodes having flexible features which can maintain apposition to ribs of the ribcage mechanism.

Relatedly, according to some embodiments, each individual rib of a ribcage mechanism can flex, such that ribs on one side (e.g right side) of the ribcage can flex either toward or away from ribs on an opposing side (e.g. left side) of the ribcage. In some cases, the ribs are relatively inflexible but not rigid. For example, the ribs can be sufficiently inflexible so that they can help to hold the suction pod or chamber in an open orientation (see, e.g., cross-section view of FIG. 15). Also, the ribs can be sufficiently non-rigid, so that they can adjust to variations in tissue thickness (see, e.g., cross-section view of FIG. 15B).

In some instances, very thin tissue to medium thickness tissue gets drawn into suction chamber without affecting rib flex significantly. In some instances, thick tissue may cause ribs to spread away from each other in cross section several degrees. By providing a ribcage with ribs providing passive stationary sidewalls with sufficient flexibility, tissues of varying thickness are allowed ingress into the chamber or between the opposing electrodes, thus enhancing electrode-tissue contact and tissue ablation.

In some instances, surgical systems may include ribcage mechanisms, suction pod mechanisms, or both, having active side walls, where movement of the ribcage and/or suction pod side walls can be drive by mechanisms other than suction. For example, clamping mechanisms may be used to actuate the side walls, thereby releasing or applying clamping pressure to tissue disposed between the opposing electrodes or ribs.

Exemplary surgical systems or belt devices may include or be used in conjunction with visualization and delivery systems including scopes with protective lenses and introducers with stylets, sheaths, and or magnets. Surgical systems or belt devices can also include a marking system for identifying to the user which electrodes are or are not in contact with tissue for ablation.

Tissue surgical systems disclosed herein are well suited for use in surgical procedures that involve ablating any of a variety of patient tissues, including without limitation the cardiac tissue of a human heart. Exemplary tissue treatment systems may include an ablation assembly or an ablation probe mechanism, and a suction stabilizer or pod mechanism. These components can be maneuvered or positioned within a patient as desired, optionally with the use of an introducer mechanism. A suction stabilizer or pod mechanism can operate to engage tissue under negative pressure such that contact or proximity between the ablation probe or electrode and the tissue to be coagulated is maintained as desired throughout a procedure. An ablation probe mechanism can be configured to conform to the specific anatomy of the target tissue area. In some cases, a distal section of the probe mechanism can include one or more ablation or coagulating electrodes. As disclosed herein, an ablation probe mechanism or ablation assembly may provide a dual alignment electrode configuration, having a first electrode assembly and a second electrode assembly, arranged in a parallel manner. The first and second electrode assemblies can be configured for the administration of RF energy or high-voltage pulses to the patient tissue. For example, a first electrode assembly can operate to deliver the RF energy or high voltage pulses, and a second electrode assembly can operate to provide a return path. Surgical systems can be configured such that electrode assemblies are directly opposed to one another at opposite sides of a suction pod. As disclosed herein, the electrode assemblies can be positioned along a recessed trough or channel of the stabilizer mechanism. Hence, surgical systems can provide a bipolar linear probe. By mounting active and return electrodes on opposite walls of a suction pod, tissue can be drawn into the vacuum pod and sandwiched or positioned between the active and return electrodes for the application of bipolar ablation. The surgical system can also include one or more holders that can hold components of the ablation probe mechanism or treatment assembly within or relative to the suction stabilizer mechanism or tissue contacting assembly. Typically, during a surgical procedure the ablation probe mechanism is coupled with an energy source, and the suction stabilizer mechanism is coupled with a vacuum source. In use, tissue is drawn into the stabilizer channel or cavity, so as to be positioned between the electrodes. When a treatment or medical procedure is completed, the ablation probe mechanism may be decoupled from the energy source.

Placement of the electrode assemblies within an inner recess or chamber of the stabilizer pod allows the system to provide enhanced direct heating of the tissue with RF or provides a more uniform field pattern to enable irreversible electroporation with lower applied voltages than would be possible with other electrode configurations. Moreover, in use such configurations can significantly reduce the amount of convective cooling in tissue which might otherwise occur. This reduction of convective cooling is especially important when the system is engaged with the epicardial surface of the working heart, in which case a dimple is created in the endocardium and convective cooling is reduced or eliminated at that location.

This reduction of endocardial convective cooling also occurs when the system is engaged with the epicardial surface of the working heart using thermal ablative elements other than RF within an inner recess or chamber of the stabilizer pod. The resultant structure of the chamber of the stabilizing pod with strategic placement of the ablation elements therein enable transmural lesion creation with ablative energy sources that do not ordinarily create lesions through the full thickness of the atrial wall. In one alternative embodiment, piezoelectric ultrasonic transducers capable of heating tissue to ablation temperatures can be placed along the opposing walls of the chamber at locations similar to the locations of electrodes used for bipolar RF ablation. For example, FIG. 15C-1 depicts a cross-section view of aspects of a surgical system 1500*c* according to embodiments of the present invention. Surgical system 1500*c* includes an ablation assembly or lesion forming mechanism 1510*c* at least partially disposed within an inner recess 1530*c* defined by a suction or stabilizer mechanism 1520*c*. As depicted here, lesion forming mechanism or ablation assembly 1510*c* includes two opposing lesion forming elements. FIG. 15C-2 illustrates a top plan view of additional aspects of the surgical system. The lesion forming mechanism or ablation assembly 1510*c* includes a first lesion forming element 1515*c* and a second lesion forming element 1525*c*. The lesion forming elements may include individual transducers T with spaces S therebetween. In some cases, each transducer T is shaped to emit a non-converging ultrasonic beam and has a length within a range from about 0.5 cm to about 2 cm, and spaces S between transducers T have a length within a range from about 1 to about 3 cm. In some case, the transducers on the facing walls are equal in size and are located to center on the spaces between the transducers on the facing walls. For this ablative technology, the suction stabilizer pod structures not only reduces endocardial cooling, but also ensures that the tissue is drawn into intimate air-free contact with the ultrasound transducer surface to enable effective transfer of ultrasound energy into the tissue. Ultrasound energy provided by the transducer can be unfocused, or slightly focused. Often, the transducer will generate a uniform ultrasound field. The intensity of the delivered ultrasound may diminish as the energy radiates throughout the tissue, for example as a function of the distance from the transducer. The amount or degree to which the intensity diminishes may depend on the frequency of the ultrasound applied. During operation of the system, the ultrasound energy may be absorbed by the patient's tissue due to vibrational absorption. Higher frequency ultrasound may be absorbed more strongly than lower frequency ultrasound. The transducer configuration (e.g. crystal type) may be selected based on a dimension (e.g. width, height, cross-section area) of the recess or chamber 1530*c*. For example, for recesses having a smaller width, it may be desirable to use a transducer that provides a higher frequency (e.g. such that energy is absorbed in a smaller area). Often, it will be desirable to provide uniform heating at a distance from the transducer. Such heating can be a result of the patient tissue absorbing the ultrasound energy. Hence, the transducer configuration and the dimensions of the recess can be carefully selected, so as to be able to provide ultrasound energy to a well-defined amount of tissue in a controlled manner. As depicted elsewhere herein, suction can be used to draw a portion of the tissue into the recess, thus eliminating or reducing the amount of air in the ultrasound administration region, thus further enhancing the effectiveness of the ultrasound treatment. In some cases, the system can provide an even temperature gradient within the recess. In some cases, for example where relatively higher frequencies are used, there may be a localized temperature gradient within the tissue, as tissue closer in proximity to the transducer becomes hotter more quickly. In some instances, a transducer configuration or frequency is selected so that a majority of the ultrasound energy is absorbed over the first half of the distance between opposing sides of the recess. As depicted in FIG. 15C-3, a conductive heating pattern can radiate from one side to another (as indicated by arrow A) and also laterally (as indicated by arrows B). As such, the heating pattern can radiate outwardly from a transducer, within the patient tissue. In some instances, the system can be configured so that the energy intensity is about 50% at a distance of about halfway between opposing sides of the recess. Techniques for determining ultrasound parameters are discussed at, for example, Ergün, "Analytical and numerical calculations of optimum design frequency for focused ultrasound therapy and acoustic radiation force" Ultrasonics, 51(7):786-94 (October 2011), the content of which is incorporated herein by reference.

For cryoablation applications, the structure of chamber or inner recess of the stabilizing pod can be used effectively to greatly reduce or eliminate endocardial convective warming. Such convective warming ordinarily prevents transmural lesion formation with epicardial application of a cryoablation probe to the epicardium of the working heart. In one embodiment of the invention, tissue is cooled along the opposing walls of the chamber or inner recess using cooling members contained within the wall of the suction stabilizing pod. For example, FIG. 15D-1 illustrates a cross-section view of a treatment system 1500*d* having a suction stabilizing pod 1510*d* that defines an inner recess 1520*d*, and two opposing lesion forming mechanisms 1530*d*, 1540*d*. In some cases, lesion forming mechanisms may include a balloon (1532*d*, 1542*d*) disposed about a hypotube (1534*d*, 1544*d*), and a thermal conductive element (1536*d*, 1546*d*) adjacent the balloon. FIG. 15D-2 provides a corresponding side view of aspects of a lesion forming mechanism having a balloon 1542*d* and hypotube 1544*d*. In one exemplary embodiment, a lesion forming mechanism or cooling assembly can include an elongate balloon having a diameter within a range from about 2 mm to about 3 mm, that is mounted over a hypotube having an internal diameter within a range from about 0.2 mm to about 0.3 mm. In some cases, within the balloon, the hypotube may contain holes H (for example having a diameter within a range from about 0.01 mm to about to 0.03 mm) that are spaced apart (for example with a spacing of about 1 cm between adjacent holes) through which coolent can be sprayed to cool and inflate the balloon during the active freezing cycle. Liquid $N_2O$ is one preferred coolent, but various other coolents could be used as well, such as DuPont ISCEON Refrigerents, Argon or Nitrogen. For croyablation systems, cooling results from the Joule-Thompson effect and if the coolent is delivered as a liquid, from the latent heat of vaporization. For the preferred coolent of liquid $N_2O$, it is believed that the latent heat of vaporization contributes to the majority of the cooling with balloon structure described. With returning reference to FIG. 15D-1, the cooling balloons 1532*d*, 1542*d* can be placed in direct physical contact with conductive elements or metallic structures 1536*d*, 1546*d* to facilitate thermal transfer between the tissue within the pod and the cooling balloon. These metallic structures can be similar to RF electrodes described elsewhere herein, because the metallic structures can be very flexible and can provide good thermal conduction along their length. During the administration of a lesion forming or ablative treatment, cold temperature from the balloon is transmitted to patient tissue which is positioned within the recess 1520*d*, for example via the conductive element or metallic structure. Generally, the pressure within the hypotube is such that the cryogenic material is maintained in a liquid state until exiting the holes. For example, the hypotube may be at room temperature (e.g. 20 to 25° C.) or body temperature (e.g. 35 to 38° C.), and the cryogenic material is pressurized so that it is liquid at this temperature. As shown in FIG. 15D-3, a pressurized liquid that is delivered through hypotube 1544*d* can exit holes H of the hypotube, and convert to gas as it enters the space between the hypotube and the balloon walls 1542*d*. Typically, there is a drop in pressure, as the material moves from an area of higher pressure (within the hypotube) to an area of lower pressure (between the hypotube and the balloon walls). Also, the cryogenic liquid typically expands upon passing through the holes H. In this way, the flow of cryogenic material from the inside of the hypotube to the outside of the hypotube generates a cooling mechanism in two ways. First, the cryogenic substance (e.g. $N_2O$) becomes cooler due to the pressure drop (e.g. decompression). Second, the cryogenic substance become cooler due to evaporation, as it transitions from a liquid to a gas. As depicted in FIG. 15D-2, holes H can be spaced along the length of the hypotube. Accordingly, the cooling effect, which is generated at the holes, is distributed along the length of the hypotube and balloon. In this way, it is possible to control where the cooling occurs. Typically, the hypotube is a small flexible and/or elastic pipe. In some instances, the hypotube may be constructed of nitinol or another material having similar shape memory and elasticity properties. In some instances, the hypotube can be constructed of stainless steel. The hypotube can be configured so that it presents appropriate flexing and bending properties. The dimensions of the holes or apertures are selected so that the desired amount of back-pressure is maintained (thus keeping the material in a liquid state) within the hypotube as the cryogenic material exits the holes. The pressure within the balloon (e.g. between the hypotube and balloon wall) can be near or slightly above atmospheric pressure. Hence, the cryogenic material or coolant enters the hypotube/balloon mechanism in a liquid state, and exits therefrom in a gaseous state. In some cases, the cryogenic material or coolant enters the hypotube/balloon mechanism in a gaseous state (high pressure) and exits therefrom in a gaseous state (low pressure). As the cryogenic material exits the holes H, it operates to expand the balloon from a relaxed configuration to an expanded configuration.

Figure 15:
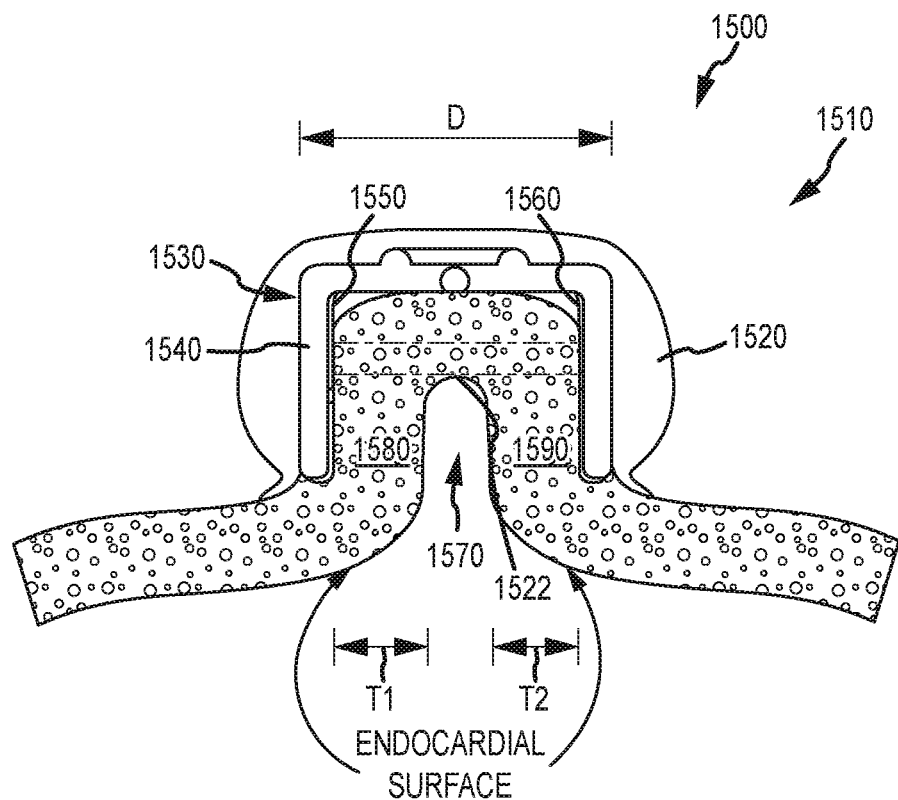
Figure 15A:
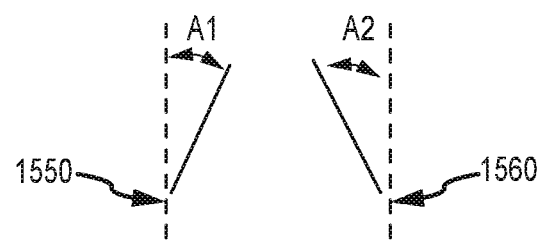
Figure 15B:
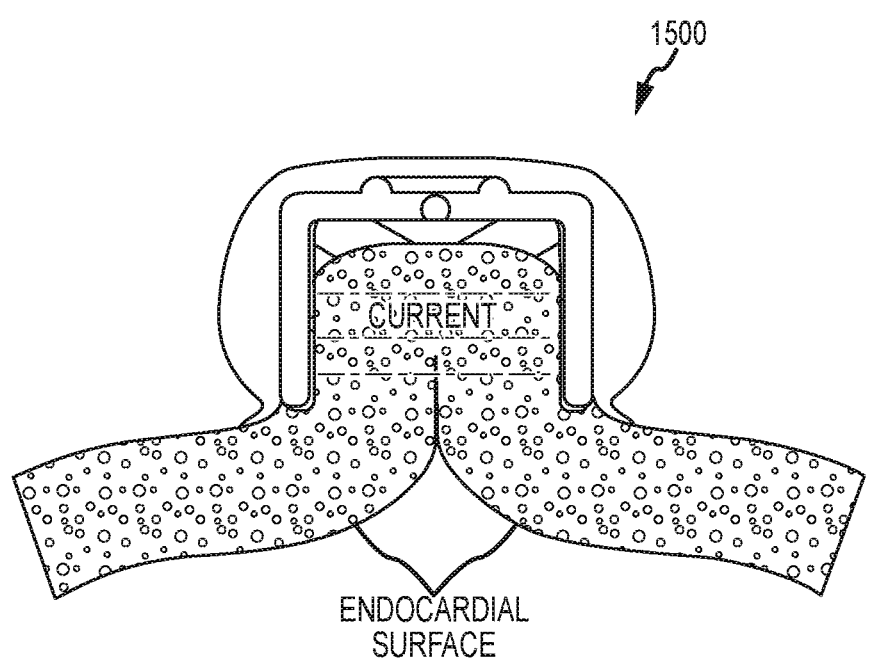
Figures 1, 15D:
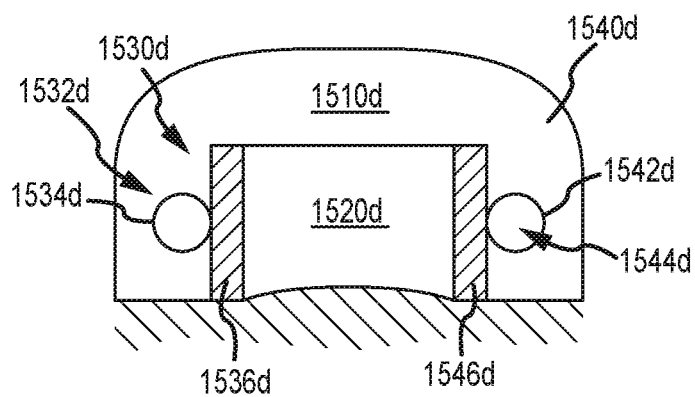
Figures 2, 15D:
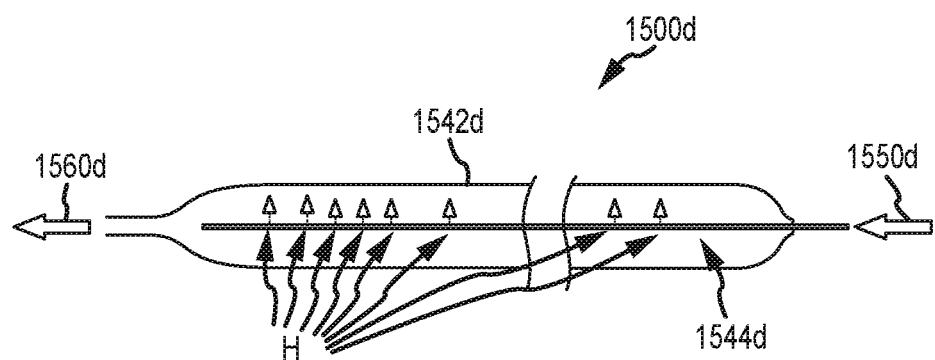
Figures 3, 15D:
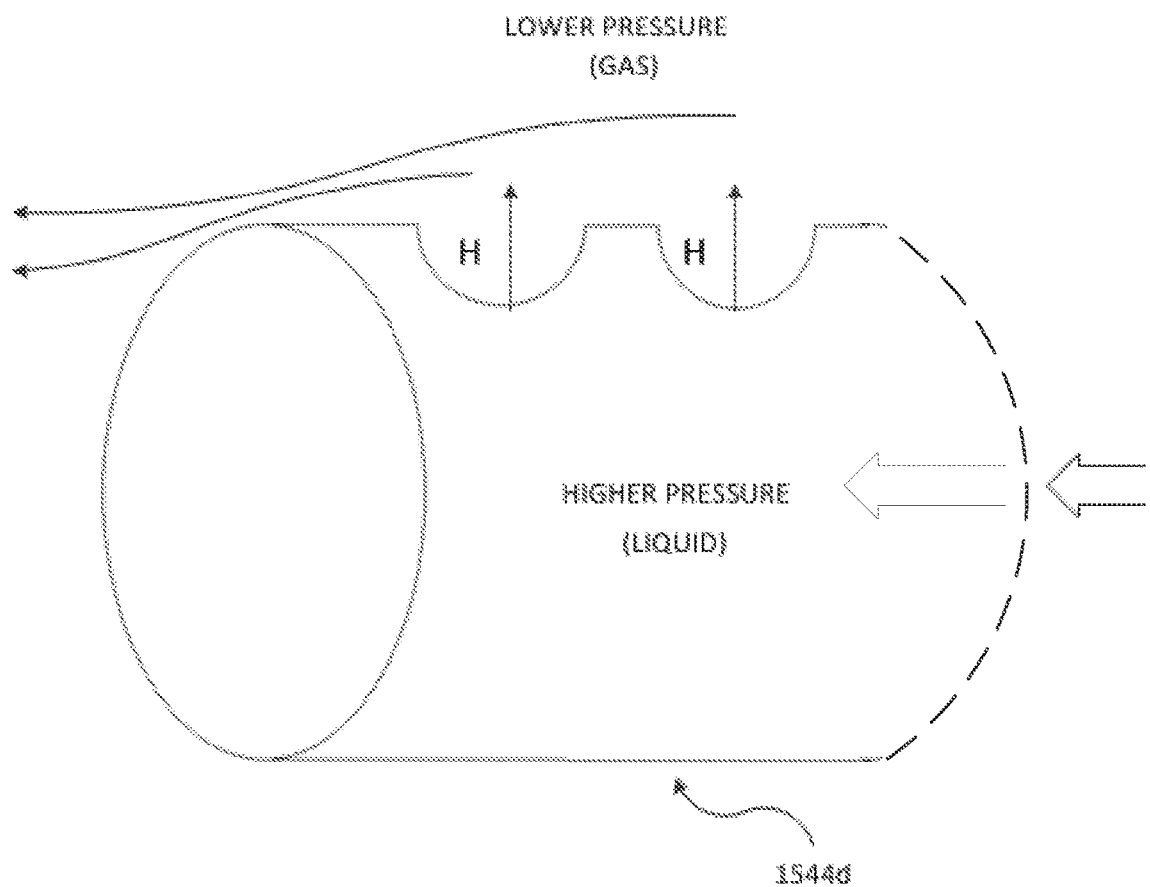
Figures 1, 15E:
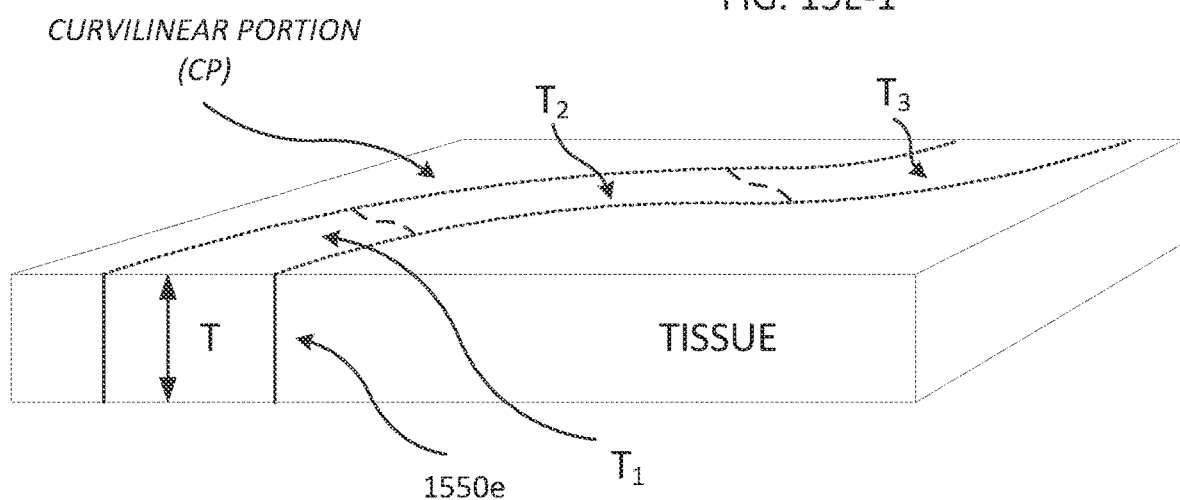
Figures 2, 3, 15E:
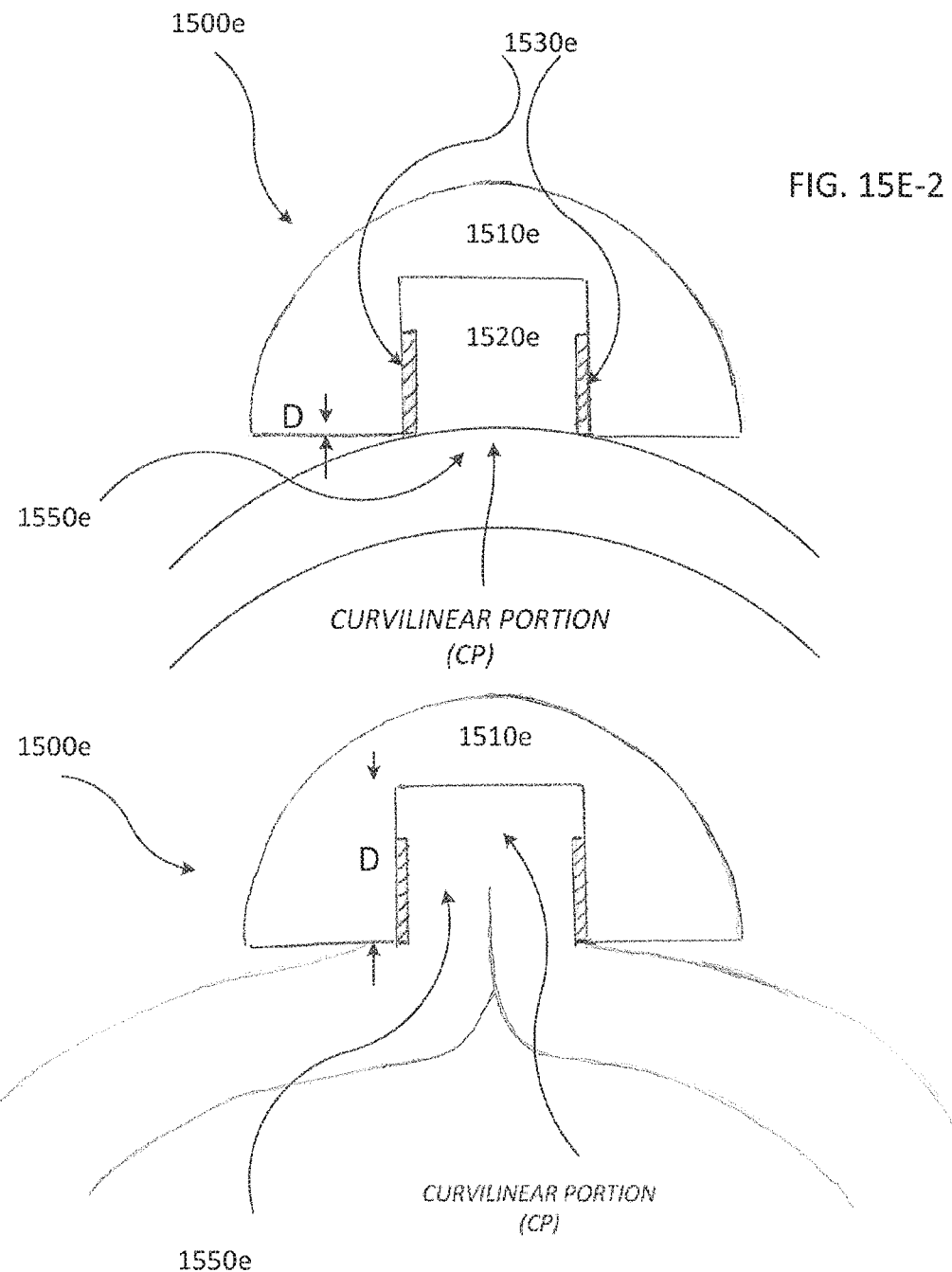

In some instances, as depicted in FIGS. 15E-1, 15E-2, and 15E-3, a surgical system 1500e for administering a lesion forming treatment to a patient tissue may include a suction mechanism 1510e defining an inner recess 1520e, and a lesion forming mechanism 1530e disposed within the inner recess 1520e. The suction mechanism 1510e can be reinforced (e.g. with a ribcage mechanism) to resist collapse when a vacuum is present within the inner recess 1520e. As illustrated here, the inner recess 1520e can be configured to receive a curvilinear portion CP to which the lesion forming treatment is administered. The curvilinear portion of tissue may have a section 1550e having a thickness T. As shown here, the curvilinear portion CP of tissue includes three regions or section along its length having tissue thickness values of $T_1$, $T_2$, and $T_3$, respectively. In some cases, the values of $T_1$, $T_2$, and $T_3$ are equivalent. In some cases, the values of $T_1$, $T_2$, and $T_3$ may differ from one another. FIG. 15E-2, depicts a cross-section view of the patient tissue, before suction is applied. As shown here, only a small portion 1550e of the patient tissue extends into the recess 1520e. For example, the tissue as depicted here extends into the recess by a distance D. In some instances, the tissue does not extend into the recess before suction is applied. This may represent a normal curved or undistorted configuration of the patient tissue, for example atrial tissue, before the tissue is drawn in suction recess. The amount to which the tissue extends into the recess (e.g. distance D) can be due to the normal curvature and may also depend on the thickness or flexibility of the tissue. For example, a thin tissue may extend further into the recess than a thick tissue. FIG. 15E-3, depicts the tissue (e.g. the curvilinear portion CP) after it has been drawn into the recess 1520e, due to application of the suction. The amount of or degree to which the tissue extends into the recess may depend on various factors, such as tissue thickness. For example, for a long lesion, for a portion of the lesion length, the entire wall thickness may be within the chamber, but along other portions, where the tissue is thicker, only 50% of the wall thickness may be within the chamber. For a curvilinear length of 15 cm, for example, the wall thickness may vary by 3-fold or more along the length of the anticipated lesion. The amount to which the tissue extends into the recess (e.g. distance D) can be due to the normal curvature and may also depend on the thickness or flexibility of the tissue. For example, FIGS. 6B and 6C illustrate that a thin tissue may extend further into the recess than a thick tissue. In some cases, the inner recess 1520e can be configured to receive the section 1550e therein, such that the section 1550e extends into the inner recess at a distance D that is greater than 0.5 T. As shown in FIG. 15E-3, the tissue become distorted, deviating from its normal cross section, as it is drawn into the recess 1520e. The recess depicted in this drawing is mostly filled with tissue.

According to some embodiments, a surgical system can include two or more metallic RF ablation electrode assemblies coupled with a silicone suction stabilizer pod. For example, a first electrode assembly can include two active (−) electrodes, and a second electrode assembly can include one return (+) electrode. During the administration of a surgical treatment procedure, the system can be inserted through a port positioned at the side of a patient, and between the patient's ribs. The system can then be advanced along a posterior surface of the heart, for example so that the exposed electrodes encircle one or more of the patient's pulmonary veins. When the stabilizer pod is positioned as desired, a vacuum or negative pressure can be applied via the stabilizer pod. Tissue is drawn into or toward the stabilizer inner recess, and the suction operates to approximate the ablation electrodes with the tissue. Ablation energy can then be applied to the tissue via the electrodes so that current flows from the active electrodes to the return electrodes, thereby establishing a current density within the intervening tissue so as to create a transmural lesion therein. In some instances, delivery and return wires can pass through the stabilizer outer surface to connect with the electrodes.

As described herein, ablation assemblies can include active electrodes and return electrodes. Often, return electrodes may also be referred to as indifferent or passive electrodes. Both active electrodes and return electrodes may be considered to provide electrical conductivity or conduction, and hence both can be considered to function electrically. Typically, power or energy (e.g. current pulses having an amplitude) is provided by an active electrode.

Suction stabilizer or pod mechanisms may present any of a variety of cross-section configurations. As shown in FIG. 1I, pod mechanism or assembly 120i provides a backbone structure having a curved convex outer surface 121i and a curved concave inner surface 122i. FIG. 1J illustrates a suction pod mechanism or assembly 120j having a backbone structure with a square or rectangular outer surface 121j and a square or rectangular inner surface 122j. FIG. 1K illustrates a suction pod mechanism or assembly 120k having a backbone structure with a trapezoidal outer surface 121k and a trapezoidal inner surface 122k. FIG. 1K-A illustrates a suction pod mechanism or assembly 120k-a having a backbone structure with a hourglass outer surface 121k-a and a trapezoidal inner surface 122k-a. Exemplary suction pod mechanisms can present any of a variety of combinations of such outer and inner surface shapes. Pod mechanism inner and outer surface shapes can configured to meet various criteria or objectives. For example, pod mechanism inner and outer surface shapes can be configured to fit within the confines of a desired port or delivery system. In some instances, pod mechanism inner and outer surface shapes can be configured to decrease or minimize the friction and catch points during axial advancement and retraction through the tissue planes and past structures along the delivery path. In some instances, pod mechanism inner and outer surface shapes can be configured to increase or maximize the range of tissue thicknesses that can be drawn into the suction recess. In some instances, pod mechanism inner and outer surface shapes can be configured to remain stable and controllable with the suction opening oriented toward target tissue. In some instances, pod mechanism inner and outer surface shapes can be configured to maintain an inner suction recess shape while allowing flexibility under the application of suction. In some instances, pod mechanism inner and outer surface shapes can be configured to allow a degree of expansion of the suction opening when engaging thick tissues as a function of differential wall thickness, wall angles, materials, contact edge geometry, electrode mounting, and suction pressure. In some instances, pod mechanism inner surface shapes or margin dimensions can be configured to enhance tissue ingress within the probe assembly. For example, tissue slides past the suction pod margins or edges as it is drawn into the pod, and margins or edges can be shaped and/or sized to facilitate this ingress.

Figure 1L:
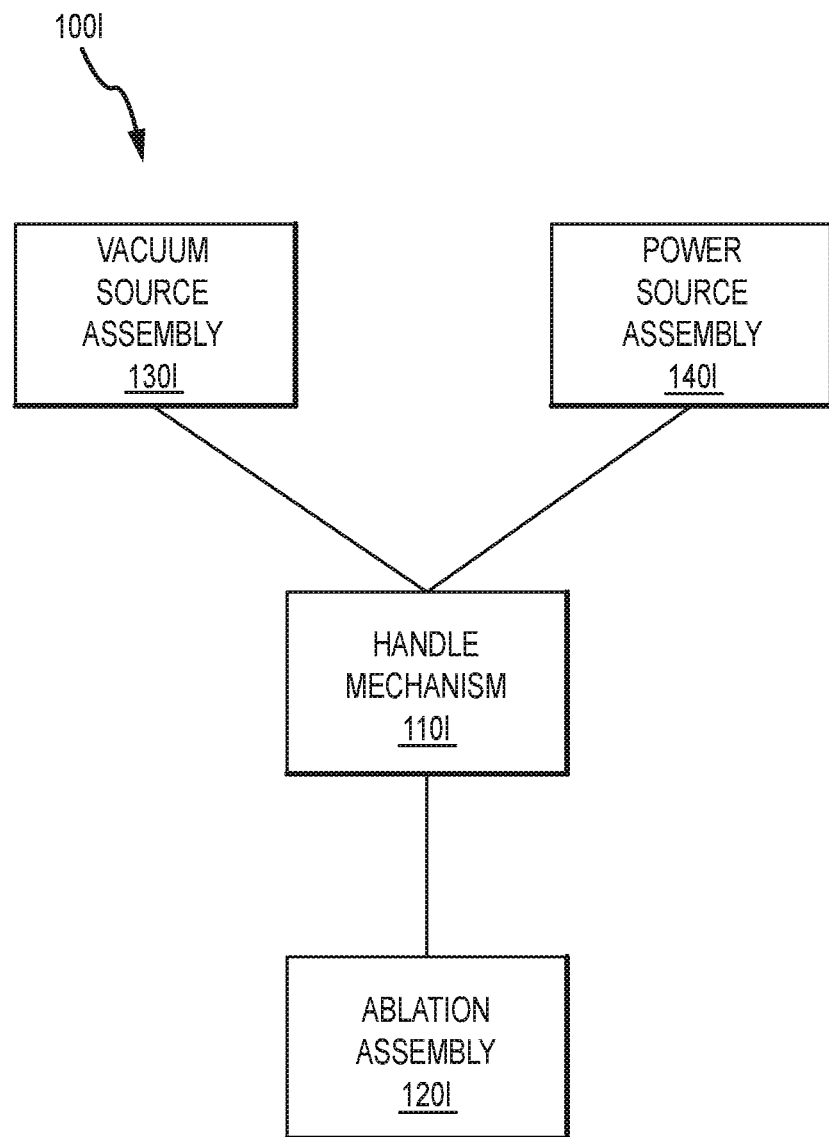

FIG. 1L shows a schematic for a surgical system 1001 according to embodiments of the present invention. Surgical system 1001 includes a handle mechanism 1101 coupled or in operative association with an ablation assembly or ablation probe mechanism 1201, a power source assembly 1401 such as an electrosurgical unit (ESU), and a vacuum source assembly 1301.

Figure 1M:
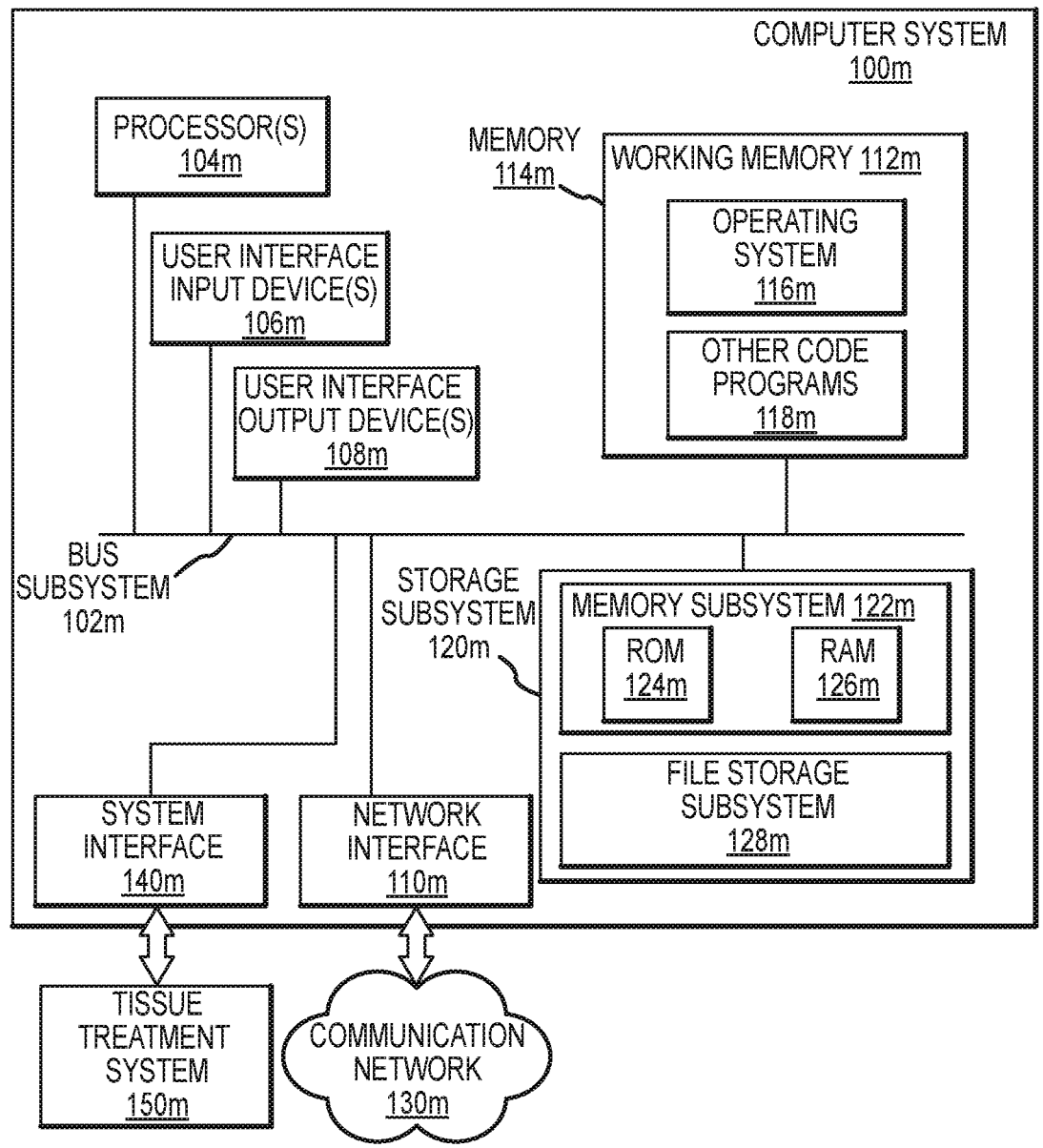

According to some embodiments, a power source assembly or electrosurgical unit (ESU) may include or be in operative association with a computer system for controlling various aspects of a surgical system. FIG. 1M is a simplified block diagram of an exemplary computer system 100m that broadly illustrates how individual system elements or aspects of a tissue treatment computer system may be implemented in a separated or more integrated manner. For example, an ESU may include a computer system that provides instructions to or interfaces with an ablation mechanism. Computer system 100m is shown comprised of hardware elements that are electrically coupled via a bus subsystem 102m, including one or more processors 104m, one or more input devices 106m such as user interface input devices, one or more output devices 108m such as user interface output devices, and a network interface 110m.

In some embodiments computer system 100m also comprises software elements, shown as being currently located within working memory 112m of memory 114m, including an operating system 116m and other code 118m, such as a program designed to implement method embodiments of the present invention. In some instances, code may be embodied on computer-readable media, such as register memory, processor cache, or RAM.

Likewise, in some embodiments computer system 100m may also include a storage subsystem 120m that can store the basic programming and data constructs that provide the functionality of the various embodiments of the present invention. For example, software modules implementing the functionality of the methods of the present invention, as described herein, may be stored in storage subsystem 120m. These software modules are generally executed by the one or more processors 104m. In a distributed environment, the software modules may be stored on a plurality of computer systems and executed by processors of the plurality of computer systems. Storage subsystem 120m can include memory subsystem 122m and file storage subsystem 128m. Memory subsystem 122m may include a number of memories including a main random access memory (RAM) 126m for storage of instructions and data during program execution and a read only memory (ROM) 124m in which fixed instructions are stored. File storage subsystem 128m can provide persistent (non-volatile) storage for program and data files, and may include tangible storage media which may optionally embody patient, device, treatment, evaluation, positioning, or other medical data. File storage subsystem 128m may include a hard disk drive, a floppy disk drive along with associated removable media, a Compact Digital Read Only Memory (CD-ROM) drive, an optical drive, DVD, CD-R, CD-RW, solid-state removable memory, other removable media cartridges or disks, and the like. One or more of the drives may be located at remote locations on other connected computers at other sites coupled to computer system 100m. The modules implementing the functionality of embodiments of the present invention may be stored by file storage subsystem 128m. In some embodiments, the software or code can provide protocols to allow the computer system 100m to communicate with communication network 130m. Often such communications can include dial-up or internet connection communications, wireless communications, or any other desired or suitable connectivity.

It is appreciated that system 100m can be configured to carry out various method aspects of the present invention. For example, processor component or module 104m can be a microprocessor control module configured to receive data or signals from input device or module 106m, and transmit data or signals to output device or module 108m and/or network interface device or module 110m. Each of the devices or modules of the present invention can include software modules on a computer readable medium that is processed by a processor, hardware modules, or any combination thereof. Any of a variety of commonly used platforms, such as Windows, MacIntosh, and Unix, along with any of a variety of commonly used programming languages, such as C or C++, may be used to implement embodiments of the present invention. In some cases, tissue treatment systems include FDA validated operating systems or software/hardware modules suitable for use in medical devices. Tissue treatment systems can also include multiple operating systems. For example, a tissue treatment system can include a FDA validated operating system for safety critical operations performed by the treatment system, such as data input, power control, diagnostic procedures, recording, decision making, and the like. A tissue treatment system can also include a non-validated operating system for less critical operations.

User interface input devices 106m may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 106m may also download a computer executable code from a tangible storage media or from communication network 130m, the code embodying any of the methods of the present invention. It will be appreciated that terminal software may be updated from time to time and downloaded to the terminal as appropriate. In general, use of the term "input device" is intended to include a variety of conventional and proprietary devices and ways to input information into computer system 100m.

User interface output devices 108m may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 100m to a user. In some cases, a tissue treatment system can include an integrated user interface device, where features of user interface input device 106m are combined with features of user interface output device 108m.

Bus subsystem 102m provides a mechanism for letting the various components and subsystems of computer system 100*m* communicate with each other as intended. The various subsystems and components of computer system 100*m* need not be at the same physical location but may be distributed at various locations within a distributed network. Although bus subsystem 102*m* is shown schematically as a single bus, alternate embodiments of the bus subsystem may utilize multiple busses.

Network interface 110*m* can provide an interface to an outside network 130*m* and/or other devices. Outside communication network 130*m* can be configured to effect communications as needed or desired with medical personnel, institutions, or other entities. It thus can receive an electronic packet from computer system 100*m* and transmits any information or signal as needed or desired back to computer system 100*m*. In addition to providing such infrastructure communications links internal to the system, the communications network system 130*m* may also provide a connection to other networks such as the internet and may comprise a wired, wireless, modem, and/or other type of interfacing connection. As noted above, in some embodiments, a computer system can be in integrated into a tissue treatment system, and in some embodiments, a computer system can be separate from, but in connectivity with, a tissue treatment system. Hence, a computer system 100*m* can include a system interface 140*m* that provides an interface to a tissue treatment system 150*m*. In some cases, a tissue treatment system 150*m* may include an ablation assembly, optionally in combination with a vacuum assembly or a handle mechanism, as disclosed elsewhere herein.

It will be apparent to those skilled in the art that substantial variations may be used in accordance with any specific requirements. For example, customized hardware might also be used and/or particular elements might be implemented in hardware, software (including portable software, such as applets), or both. Further, connection to other computing devices such as network input/output devices may be employed. Computer terminal system 100*m* itself can be of varying types including a computer terminal, a personal computer, a portable computer, a workstation, a network computer, or any other data processing system. Due to the ever-changing nature of computers and networks, the description of computer system 100*m* depicted in FIG. 1M is intended only as a specific example for purposes of illustrating one or more embodiments of the present invention. Many other configurations of computer system 100*m* are possible having more or less components than the computer system depicted in FIG. 1M. Relatedly, any of the hardware and software components discussed above can be integrated with or configured to interface with other medical treatment or information systems used at other locations.

Figure 2A:
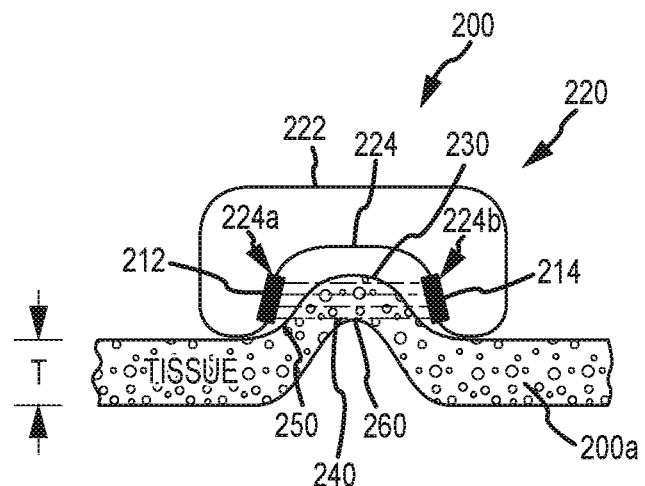
FIGS. 2A to 2D show aspects of surgical systems and methods according to embodiments of the present invention.

FIG. 2A provides a cross-section view of a surgical system 200 in operational engagement with a patient tissue 200*a* having a thickness T. Surgical system 200 includes an ablation probe mechanism having a first electrode assembly 212 and a second electrode assembly 214. The ablation probe mechanism is coupled with a suction stabilizer mechanism 220. As shown here, suction mechanism 220 includes an outer convex surface or shell 222 and an inner concave recess or cavity 224. First electrode assembly 212 is located at a first position 224*a* along inner cavity 224, and second electrode assembly 214 is located at a second position 224*b* along inner cavity 224 opposite the first position 224*a*. First electrode assembly 212 and second electrode assembly 214 can present a bipolar configuration. For example, first electrode assembly 212 can provide an active electrode for delivering RF energy, and second electrode assembly 214 can provide a return electrode for returning RF energy. As shown here, a section 230*b* of patient tissue is drawn into the inner recess of the suction stabilizer. During the administration of a bipolar ablation treatment, current 240 passes through this section of patient tissue, from the active electrode 212 to the return electrode 214. As the current sufficiently heats the tissue, for example by passing from one tissue surface 250 to an opposing tissue surface 260, across the entire thickness T of the tissue, a transmural lesion is created.

Figure 2B:
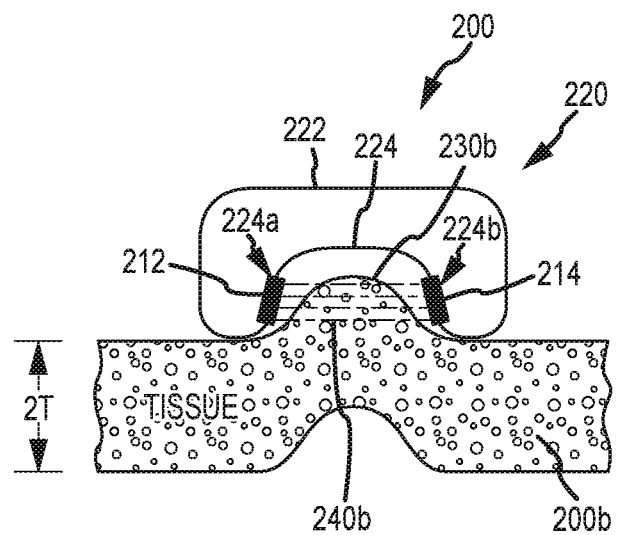

FIG. 2B provides a cross-section view of a surgical system 200 in operational engagement with a patient tissue 200*b* having a thickness 2 T, which is twice the tissue thickness represented in FIG. 2A. Surgical system 200 includes an ablation probe mechanism having a first electrode assembly 212 and a second electrode assembly 214. The ablation probe mechanism is coupled with a suction stabilizer mechanism 220. As shown here, suction mechanism 220 includes an outer convex surface or shell 222 and an inner concave recess or cavity 224. First electrode assembly 212 is located at a first position 224*a* along inner cavity 224, and second electrode assembly 214 is located at a second position 224*b* along inner cavity 224 opposite the first position 224*a*. First electrode assembly 212 and second electrode assembly 214 can present a bipolar configuration. For example, first electrode assembly 212 can provide an active electrode for delivering RF energy, and second electrode assembly 214 can provide a return electrode for returning RF energy. As shown here, a section 230 of patient tissue is drawn into the inner recess of the suction stabilizer. During the administration of a bipolar ablation treatment, current 240*b* passes through this section of patient tissue, from the active electrode 212 to the return electrode 214. As shown here, the increased thickness 2 T of the patient tissue can make it difficult for system 200 to administer a fully transmural lesion.

Figure 2C:
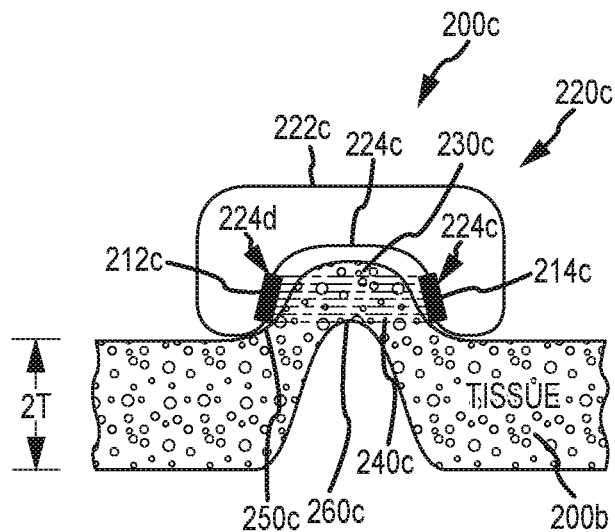

Hence, it may be desirable to use a surgical system having a larger suction stabilizer when treating thicker tissue. A suction stabilizer having a larger recess can be helpful for accommodating a thicker tissue, so that the tissue, which may be the atrial wall of a patient, is drawn sufficiently into the recess and between the electrodes. For example, FIG. 2C, shows a cross-section view of surgical system 200*c* in operational engagement with a patient tissue 200*b* having a thickness 2 T. Surgical system 200*c* includes an ablation probe mechanism having a first electrode assembly 212*c* and a second electrode assembly 214*c*. The ablation probe mechanism is coupled with a suction stabilizer mechanism 220*c*. As shown here, suction mechanism 220*c* includes an outer convex surface or shell 222*c* and an inner concave recess or cavity 224*c*. First electrode assembly 212*c* is located at a first position 224*d* along inner cavity 224*c*, and second electrode assembly 214*c* is located at a second position 224*e* along inner cavity 224*c* opposite the first position 224*d*. First electrode assembly 212*c* and second electrode assembly 214*c* can present a bipolar configuration. For example, first electrode assembly 212*c* can provide an active electrode for delivering RF energy, and second electrode assembly 214*c* can provide a return electrode for returning RF energy. As shown here, a section 230*c* of patient tissue is drawn into the inner recess of the suction stabilizer. During the administration of a bipolar ablation treatment, current 240*c* passes through this section of patient tissue, from the active electrode 212*c* to the return electrode 214*c*. As the current sufficiently heats the tissue, for example by passing from one tissue surface 250*c* to an opposing tissue surface 260*c*, across the entire thickness 2 T of the tissue, a transmural lesion is created.

Exemplary systems described herein are well suited for use in ablating atrial tissue, which typically has a thickness of about 4 mm. For atrial wall ablation, some configurations for the suction pod cavity or recess can have a well depth of about 5 to 10 mm, and a well width at the sidewall opening of about 5 to 10 mm. Similarly, systems with suction pods that are somewhat deeper and wider can be used for ablating the epicardium of the ventricle.

Figure 2D:
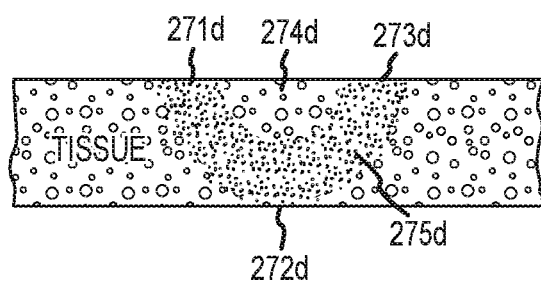

As indicated in FIG. 2C, tissue is sucked up into the "U" shaped suction stabilizer, and current density 240c spreads through or across the patient tissue disposed between the electrodes. In turn, the tissue becomes heated and a lesion forms. Upon heating and ablation, a change in tissue color (e.g. red changing to brown) can be observed from the opposing side of the tissue, at location 260c. Upon removal of the system 200c, the patient tissue resumes a flattened or straightened configuration. As shown in the tissue cross-section view of FIG. 2D, the resulting ablation pattern 275d can generally have a shape of a "V" or "U". The lesion is transmural, for example between first upper location 271d and lower location 272d, or between second upper location 273d and lower location 272d. Hence, although there may be an area of unablated or underablated tissue between first upper location 271d and second upper location 273d, at central upper location 274d, a true transmural bipolar lesion is produced as the lesion is present across the entire thickness of the tissue, from one surface to the opposing surface.

As depicted in FIGS. 2A to 2D, for example, embodiments of the present invention include methods and systems for enfolding tissue into a recess to enhance contact or approximation between the tissue and the system electrodes. Hence, the transmurality of ablations delivered by the system can be enhanced or optimized. What is more, embodiments of the present invention encompass systems and methods that provide dual electrode sets along sides of an inner recess of an ablation mechanism or suction pod, where an electrode set along one side operates as an active electrode assembly, and an electrode set along an opposing side operates as a return electrode assembly.

Embodiments of the present invention also encompass systems having various multiple electrode spacing schemes. For example, FIG. 3A, provides a cross-section view of a surgical system 300a that includes an ablation mechanism 310a having a first electrode assembly 312a and a second electrode assembly 314a. System 300a also includes a suction stabilizer mechanism 320a coupled with or in operative association with the ablation mechanism. As shown here, suction stabilizer mechanism 320a defines a recess 324a having a depth D, and each of the electrode assemblies 312a and 314a define a height H, such that depth D and height H are approximately the same or equal. In some cases, depth D is about 10 mm. In some cases, the distance between electrodes is about 10 mm. Optionally, ablation probe assemblies can be configured for treating tissues having any of a variety of widths, including for example tissue thicknesses of 2 mm, 3 mm, 4 mm, 5 mm, 6 mm, 7 mm, 8 mm, and the like.

FIG. 3B provides a cross-section view of a surgical system 300b that includes an ablation mechanism 310b having a first electrode assembly 312b and a second electrode assembly 314b. System 300b also includes a suction stabilizer mechanism 320b coupled with or in operative association with the ablation mechanism. As shown here, suction stabilizer mechanism 320b defines a recess 324b having a depth D, and each of the electrode assemblies 312b and 314b define a height H, such that depth D is greater than height H. At a first side of the stabilizer recess, the stabilizer presents a recess wall 330b having a proximal section 332b and a distal section 334b. At a second side of the stabilizer recess, opposite the first side, the stabilizer presents an opposing recess wall 331b having a proximal section 333b and a distal section 335b. First electrode assembly 312b is positioned at or near recess wall distal section 334b, and second electrode assembly 314b is positioned at or near opposing recess wall distal section 335b.

FIG. 3C provides a cross-section view of a surgical system 300c that includes an ablation mechanism 310c having a first electrode assembly 312c and a second electrode assembly 314c. System 300c also includes a suction stabilizer mechanism 320c coupled with or in operative association with the ablation mechanism. As shown here, suction stabilizer mechanism 320c defines a recess 324c having a depth D, and each of the electrode assemblies 312c and 314c define a height H, such that depth D is greater than height H. At a first side of the stabilizer recess, the stabilizer presents a recess wall 330c having a proximal section 332c, a central section 334c, and a distal section 336c. At a second side of the stabilizer recess, opposite the first side, the stabilizer presents an opposing recess wall 331c having a proximal section 333c, a central section 335c, and a distal section 337c. First electrode assembly 312c is positioned at or near recess wall central section 334c, and second electrode assembly 314c is positioned at or near opposing recess wall central section 335c.

FIG. 3D provides a cross-section view of a surgical system 300d that includes an ablation mechanism 310d having a first electrode assembly 312d and a second electrode assembly 314d. System 300d also includes a suction stabilizer mechanism 320d coupled with or in operative association with the ablation mechanism. As shown here, suction stabilizer mechanism 320d defines a recess 324d having a depth D, and each of the electrode assemblies 312d and 314d define a height H, such that depth D is greater than height H. At a first side of the stabilizer recess, the stabilizer presents a recess wall 330d having a proximal section 332d, a central section 334d, and a distal section 336d. At a second side of the stabilizer recess, opposite the first side, the stabilizer presents an opposing recess wall 331d having a proximal section 333d, a central section 335d, and a distal section 337d. First electrode assembly 312d is positioned at or near recess wall distal section 336d, and second electrode assembly 314d is positioned at or near opposing recess wall proximal section 333d.

Figure 3E:
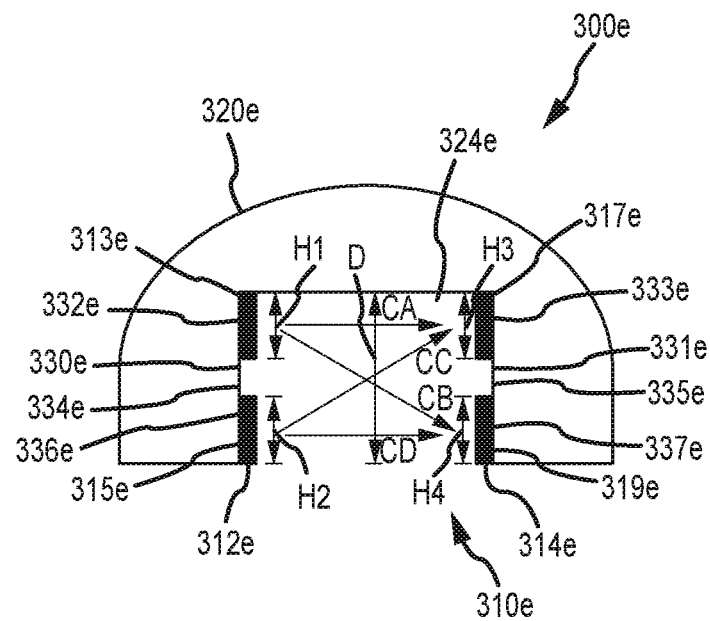

FIG. 3E provides a cross-section view of a surgical system 300e that includes an ablation mechanism 310e having a first electrode assembly 312e and a second electrode assembly 314e. First electrode assembly 312e includes a proximal electrode 313e and a distal electrode 315e. Second electrode assembly 314e includes a proximal electrode 317e and a distal electrode 319e. System 300e also includes a suction stabilizer mechanism 320e coupled with or in operative association with the ablation mechanism. As shown here, suction stabilizer mechanism 320e defines a recess 324e having a depth D, and each of the electrodes 313e, 315e, 317e, and 319e define a height H1, H2, H3, and H4, respectively, such that depth D is greater than each of height H1, H2, H3, and H4. At a first side of the stabilizer recess, the stabilizer presents a recess wall 330e having a proximal section 332e, a central section 334e, and a distal section 336e. At a second side of the stabilizer recess, opposite the first side, the stabilizer presents an opposing recess wall 331e having a proximal section 333e, a central section 335e, and a distal section 337e. Electrode 313e is positioned at or near recess wall proximal section 332e, electrode 315e is positioned at or near recess wall distal section 336e, electrode 317e is positioned at or near recess wall proximal section 333e, and electrode 319e is positioned at or near recess wall distal section 337e.

Any of a variety of current flow pathways and combinations of pathways can be implemented by providing energizing and return circuits between the various electrodes. For instance, when electrodes 313e and 317e are configured as a circuit, for example by coupling them with a related power delivery and return interfaces of an electrosurgical unit (not shown), system 300e can provide a current flow pathway as indicated by arrow CA. When electrodes 313e and 319e are configured as a circuit, for example by coupling them with a related power delivery and return interfaces of an electrosurgical unit (not shown), system 300e can provide a current flow pathway as indicated by arrow CB. When electrodes 315e and 317e are configured as a circuit, for example by coupling them with a related power delivery and return interfaces of an electrosurgical unit (not shown), system 300e can provide a current flow pathway as indicated by arrow CC. When electrodes 315e and 319e are configured as a circuit, for example by coupling them with a related power delivery and return interfaces of an electrosurgical unit (not shown), system 300e can provide a current flow pathway as indicated by arrow CD. Relatedly, systems 300e is configurable to deliver combinations of current flow pathways, for example pathway CA in combination with pathway CD, and the like. Hence, embodiments of the present invention encompass systems that provide multiple electrode spacing and activation schemes.

As depicted in FIGS. 3A to 3E, for example, embodiments of the present invention encompass systems and methods that can switch between monopolar electrode capability and bipolar electrode capability. Systems and methods may also include multiple electrode sets having opposed active and/or return electrodes. Various structural elements of an ablation mechanism, such as a ribcage assembly, a suction pod assembly, or a combination thereof can operate to allow suction or negative pressure to draw tissue into a recess and against or toward the electrodes.

Figure 4:
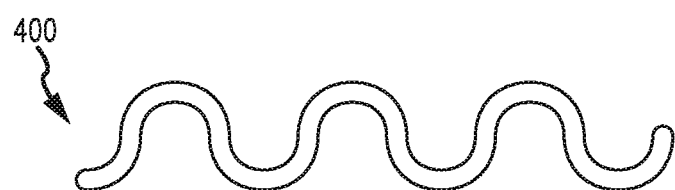
FIG. 4 shows aspects of an electrode mechanism according to embodiments of the present invention.

Embodiments of the present invention also encompass systems having various ablation element design and shape configurations. For example, FIG. 4 shows an electrode 400 having a serpentine configuration. Exemplary electrode mechanisms can have an electrode shaped lengthwise to allow bending and length changes. Electrode mechanisms can provide one or more electrodes shaped lengthwise in a straight, serpentine, or other shape. Hence, several electrode designs and arrays are possible, including without limitation planar electrodes, cylindrical helical electrodes, and linear wire/cable/strip type electrodes. According to some embodiments, electrode configuration can provide a screen mechanism whereby suction provided by a vacuum source can be transmitted therethrough, for application to a patient tissue.

Figure 5:
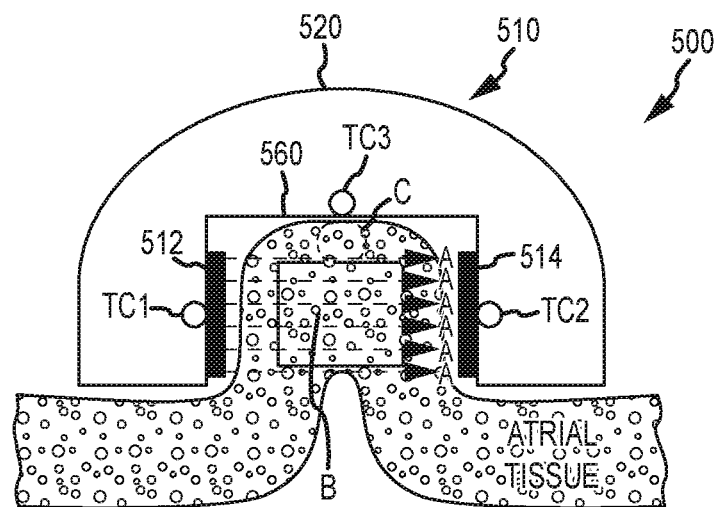
FIGS. 5 and 5A show aspects of surgical systems and methods according to embodiments of the present invention.

In some instances, tissue treatment systems can include one or more temperature sensors for detecting the temperature at selected locations. FIG. 5 illustrates a cross-section of a surgical system 500 according to embodiments of the present invention. System 500 includes an ablation mechanism 510 having a first electrode assembly 512 and a second electrode assembly 514. System 500 also includes a suction stabilizer mechanism 520 coupled with or in operative association with the ablation mechanism. As shown here, system 500 further includes a first temperature sensor, such as a thermocouple TC1, in operative association with first electrode assembly 512, and a second temperature sensor, such as thermocouple TC2, in operative association with second electrode assembly 514. For example, thermocouples TC1 and TC2 can be in thermal contact with electrodes 512 and 514, respectively. System 500 also includes a third temperature sensor, such as thermocouple TC3, located at a central recess wall portion 560 of suction stabilizer mechanism 520.

When ablation mechanisms or electrodes 512 and 514 are configured as a circuit, for example by coupling them with a related power delivery and return interfaces of an electrosurgical unit (not shown), system 500 can provide a current flow pathway as indicated by arrows A. Current passing through this section B of the patient tissue causes an increase in tissue temperature, due to ohmic heating and the electrical resistance properties of the tissue. The system is configured such that current passing through the ablation elements 512, 514 does not directly lead to an increase in electrode temperature. Changes in temperature sensed by the temperature sensors TC1, TC2, TC3 are due to heat conducted from the heated tissue to the sensors. Section C, and relatedly temperature sensor TC3, are at the coolest identifiable or measurable location. There is less current density flowing through section C of the patient tissue as compared with the directly heated tissue at section B. Section C is furthest from the directly heated tissue at section B, and the increase in temperature at section B precedes the increase in temperature at section C. In some instances, the temperature at thermocouple TC3 or section C can be used to confirm or assess the status of a transmural ablation, while the temperature at thermocouples TC1 and TC2 (which is higher than the temperature at thermocouple TC3) can be used for controlling amounts of the energy delivered between electrodes 512 and 514. Relatedly, the temperature at thermocouple TC3 or section C can be used to confirm that a transmural lesion has been completed. For example, if temperature sensor TC3 indicates a temperature of 60° Celsius at tissue section C, it is possible to conclude that the temperature at tissue section B is 60° Celsius or higher (e.g. 80° Celsius). Because transmural lesions in atrial tissue often occur where the tissue is heated above 50° Celsius across the full thickness of the tissue, a reading of 60° Celsius at temperature sensor TC3 can be considered to signal the successful formation of a lesion. Embodiments of the present invention also encompass systems having thermal sensors positioned at various locations on or within the system.

Figure 5A:
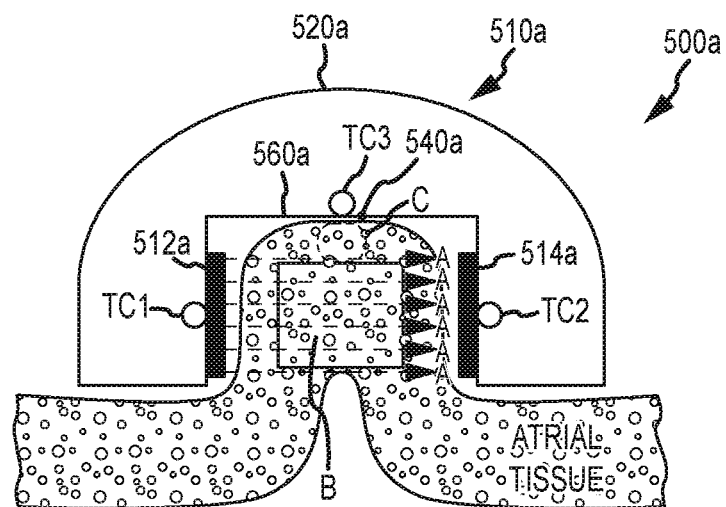

According to some embodiments, systems can include stimulation mechanisms for pacing or sensing mechanism for evaluating resistivity. FIG. 5A illustrates a cross-section of a surgical system 500a according to embodiments of the present invention. System 500 includes an ablation mechanism 510a having a first electrode assembly 512a and a second electrode assembly 514a. System 500a also includes a suction stabilizer mechanism 520a coupled with or in operative association with the ablation mechanism. As shown here, system 500a further includes a first temperature sensor, such as a thermocouple TC1, in operative association with first electrode assembly 512a, and a second temperature sensor, such as thermocouple TC2a, in operative association with second electrode assembly 514a. System 500a includes a third temperature sensor, such as thermocouple TC3, located at a central recess wall portion 560a of suction stabilizer mechanism 520a. System 500a also include a transmission element 540a. In some instances, transmission element 540a can include a small surface area electrode for placement at or near location C to enable pacing or to be used to sense local tissue resistivity. The transmission element could include a spot electrode having a diameter of about 2 mm, or it could include a thin elongate wire or electrode strip that is the same length as the ablation electrodes 512a and 514a. In some instances, transmission element 540a may be narrower than the ablation electrodes. For example, transmission element may have a diameter within a range from about 0.5 mm to about 1.5 mm.

Prior to the application of an ablation, transmission element 540a can be used in a pacing mode to determine if the patient tissue was drawn sufficiently far enough into the stabilizer channel, so that transmission element 540a contacts region C of the patient tissue. If the transmission element can not pace the heart using 20 Volt 1 msec wide pacing pulses, then it is possible to conclude that contact between the transmission element and the patient tissue has not been established and the success of the ablation is less likely. Typically, pacing is an all-or-none phenomenon, and stimulation of just a few cells at a sufficiently high local voltage gradient leads to stimulation of the surrounding tissue due to the propagation properties of the tissue. When contact is established, which may be observed by a pacing response as the stimulation is propagated through the tissue, a baseline resistance reading using a frequency of 50 kHz to 500 KHz can be taken from the transmission element to electrodes 514a and 512a. All other factors being equal, tissue resistivity decreases by 2%/° C. Since the measured resistance is primarily dependent on the resistivity within 1-2 mm of transmission element 540, the measured resistance provides an estimate of the weighed-average temperature of tissue near the transmission element. The weighted average is inversely proportional or related to the current density. The weighted average can be used to determine an average temperature along the entire contacted region, and hence the resistivity provides a distributed measurement parameter of temperature. A reduction of 35% from baseline indicates that the local tissue temperature is about 60° C., and is a good indication that lesion transmurality is achieved. Such spatial heat averaging techniques can be used to determine current density in tissue, as a change in resistivity is reflective of what is occurring in the tissue locally.

In some instances, the cross-section of transmission element 540 may be circular. Optionally, transmission element 540 may include a spot electrode or a thin wire or layer of conductive material for pacing or impedance sensing. Optionally, transmission element 540 may be equal in length to that of either or both of the electrode assemblies. The transmission element can be sized so that in use it samples only tissue that is positioned relatively near to it. Typically, the tissue closest to the transmission element, for example within about one to two millimeters of the transmission element, provides a significant percentage of the resistivity measured. System 500 can be used to perform pacing techniques such as those described in U.S. patent application Ser. No. 12/463,760 filed May 11, 2009, the content of which is incorporated herein by reference.

According to some embodiments, the pacing technique can allow the transmission element 540 to operate as a contact sensor. Hence, if a sufficiently high pacing voltage is applied through the transmission element such that contact between the transmission element and tissue will likely result in a stimulation response, then the presence of such a stimulation response can be used as an indication of contact between the transmission element and the tissue. In the absence of contact, for example where the transmission element and the tissue are separated by a distance of 0.1 mm or 0.01 mm, there will not be enough current passing into the tissue so as to generate a stimulation response.

Generally, resistivity can provide an accurate measurement of temperature, particularly where the tissue remains sufficiently hydrated. Excessive temperatures may cause tissue to lose hydration, however. Because transmission element 540 is positioned along the tissue at a relatively cool location at section C, away from electrode assemblies 512a and 514a, there is less loss of hydration and hence the accuracy of the temperature measurement remains high during the application of an ablation treatment when tissue section B is heated to create a lesion.

Moreover, because this technique provides a ratiometric measurement, as long as the tissue at section C does not significantly change during the measurement period, even if there was some degree of drying or char there prior to ablation, it will not impact the impedance measurement; the percentage change in resistivity provides a good reflection of the temperature change in the sample tissue during a particular ablation application, and the lesion confirmation functionality of transmission element 540 remains viable.

Surgical systems such as treatment system 500 can include any desired number of active and return electrodes. For example, surgical systems can include 6 or 7 active electrodes and 1 or 2 inactive electrodes. Systems can be configured to deliver various types of regulated energy delivery, such as RF energy which is controlled by maintaining a set tissue temperature. Temperature sensors can be placed at multiple locations along the length and cross-section of the device, for example in close contact with the active ablating electrode(s) and along the center line of the roof of the suction stabilizer to provide an indication of temperature at the tissue center away from ablation.

With reference to FIGS. 5 and 5A, for example, and as further disclosed herein, exemplary systems and methods provide ablation functions, pacing functions, and combinations thereof, at multiple locations along the same or opposing walls of a suction pod or ribcage mechanism. In some instances, treatment systems may include a temperature sensor in operative association with a return electrode. In some instances, treatment systems may include a temperature sensor disposed along a central inner recess. In some instances, treatment systems may include a temperature sensor in operative association with an active electrode.

In some instances, tissue treatment systems can include one or more cooling or irrigation mechanisms for cooling or irrigation of selected system features. For example, a surgical system may include an ablation mechanism having a first electrode assembly and a second electrode assembly. The system may also include a suction stabilizer mechanism coupled with or in operative association with the ablation mechanism. Moreover, the system may include multiple cooling or irrigation lumens, such as first, second, and third cooling or irrigation lumens, respectively. Such lumens can be, for example, formed as open or closed channels along suction stabilizer mechanism. Saline or other fluid can be transmitted through the lumens to accomplish cooling or irrigation of the device, the patient tissue, or both. In some instances, fluid passing through a first lumen can help to regulate the temperature of a first electrode, and fluid passing through a second lumen can help to regulate the temperature of a second electrode. Fluid passing through or along lumens or channels can help to irrigate or regulate the temperature of patient tissue T.

Figure 6A:
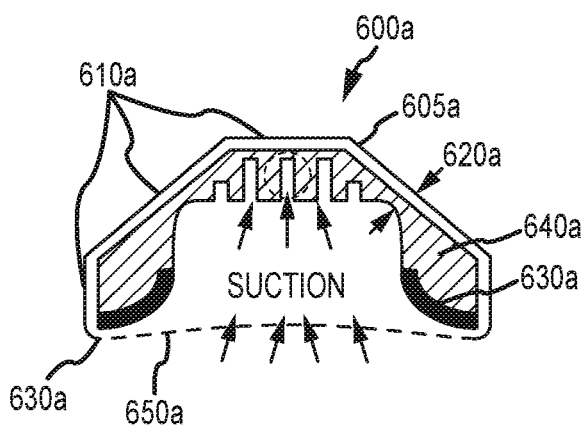
FIGS. 6A to 6D show aspects of surgical systems and methods according to embodiments of the present invention.
Figure 6B:
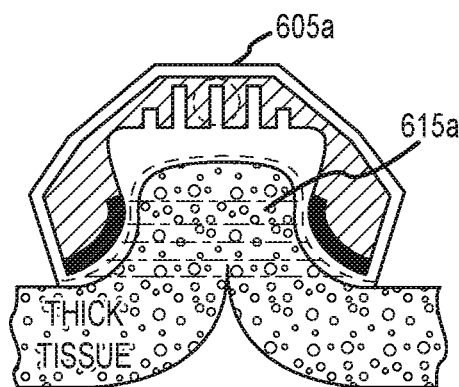
Figure 6C:
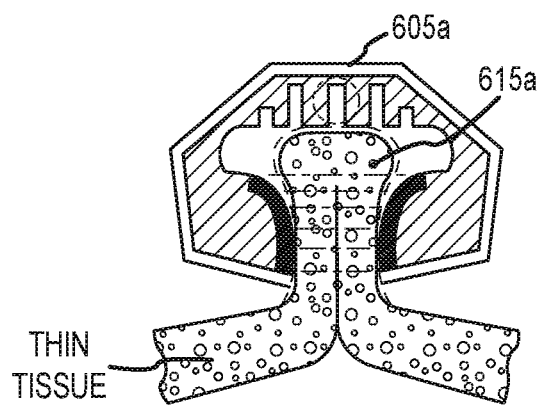

FIG. 6A depicts aspects of a surgery system 600a according to embodiments of the present invention. Such systems are well suited for use in epicardial transmural ablation procedures, including bipolar ablation approaches. As shown in this probe assembly cross-section, the system includes a membrane or pod mechanism 610*a* that encases a ribcage mechanism 640*a* therein. The probe assembly provides a hinge point 620*a* about which the membrane and ribcage may flex. In some instances, a probe assembly may include a web mechanism 650*a* having a porous, elastic or non-elastic, flexible material that bridges a span between the suction pod arms or electrode arms. As tissue is drawn into the probe assembly and between the arms, the web mechanism 650*a* is drawn in as well, thus pulling the arms together, for example until a fold is created in the tissue.

Figure 6D:
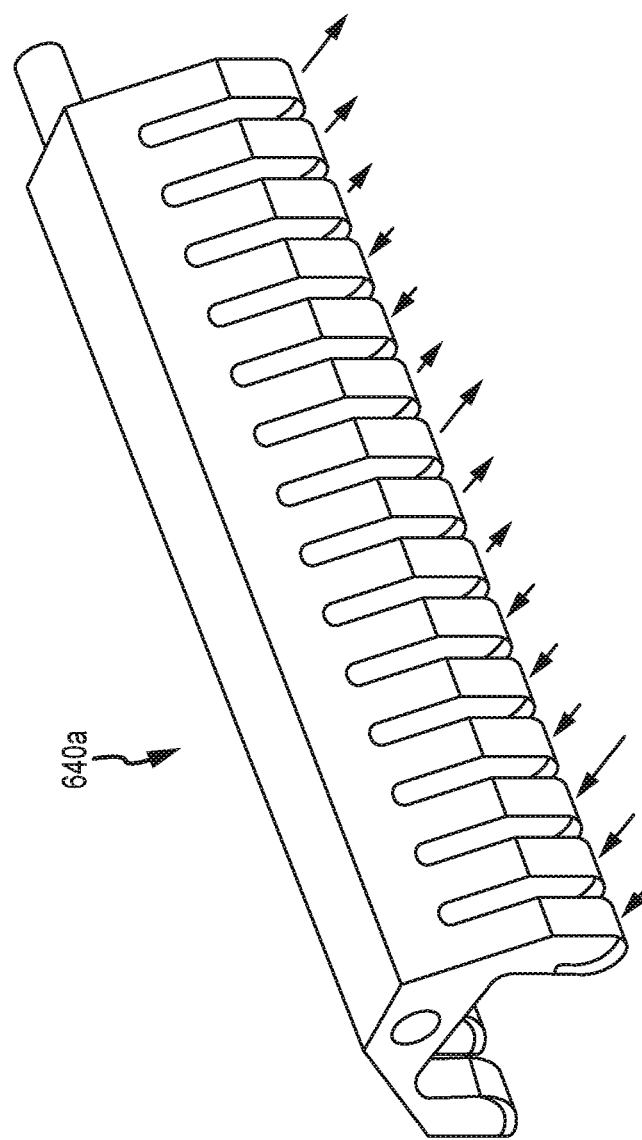

As shown in FIGS. 6B and 6C, and as with other embodiments disclosed herein, the probe assembly 605*a* allows the electrodes to be in apposition to tissues having a variety of thicknesses (e.g. thick tissue as shown in FIG. 6B, or thin tissue as shown in FIG. 6C), and can be used to create transmural lesions without epicardial lesion gaps or excessively wide lesions. The dotted lines 615*a* within the tissue represent current flow through the tissue. When the tissue is released from the probe assembly 605*a*, the tissue is thereafter provided with a transmural lesion. As shown in FIG. 6D, a flexible ribcage mechanism 640*a* can have individual fingers or ribs that can bend or flex either toward or away from the center of the ribcage, thus enabling the ribcage 640*a* to accommodate tissues of varying thickness and to provide width adjustability along its length.

In some instances, surgical systems may include ribcage mechanisms, suction pod mechanisms, or both, having active side walls, where movement of the ribcage and/or suction pod side walls can be driven by mechanisms other than suction. For example, clamping mechanisms may be used to actuate the side walls, thereby releasing or applying clamping pressure to tissue disposed between the opposing electrodes or ribs. In some cases, a surgical system may include lengthwise clamps or tongs disposed along the exterior of opposing sides of a suction pod mechanism, whereby such clamps or tongs can actuate to squeeze tissue between the suction pod side walls. In some cases, beating heart tissue can be drawn by suction into the a probe suction chamber or recess, and can conform to a degree to the confines of the chamber or recess, between the ribcage sidewalls or ablation electrodes. In some cases, the electrodes are shaped to follow the geometry of the infolded tissue, thus enhancing contact between the electrodes and the tissue. For example, electrodes may be curved, straight, angled inward at the top, or otherwise configured to both conform to and help shape the infolding tissue. In some cases, a ribcage mechanism may include a central spine, with ribs disposed either inside or outside of a suction pod. As indicated above, FIGS. 6A to 6D depict aspects of a treatment system that delivers a bipolar epicardial transmural ablation, according to embodiments of the present invention. As shown here, the system presents hinge points, and includes electrodes and a membrane that encases the structure to seal a vacuum within. The system also includes a very porous, non-elastic, flexible web material that forms a bridge between the flexible electrode arms. As tissue is drawn between the arms, the web material is drawn in as well, and the arms are pulled together until a tissue fold is created. Such embodiments allow electrodes to be in apposition to various thickness of tissue so as to create a transmural lesion without an epicardial lesion gap or an excessively wide lesion. In the upper panels showing the pinched thick and thin tissues, the dotted lines represent current flow through tissue. When tissue is released, the lesion is transmural. These embodiments allow for overall flexibility, including upward, downward, and sideways movements. In some instances, individual electrode fingers can enable the treatment of varying tissue thicknesses, and provide adjustability along the length of the device. The system can be configured as a short connecting lesion device as described with reference to FIG. 13, or as a long loop device as described with reference to FIG. 14. The system can accommodate differing thicknesses of tissue, and further, can accommodate different thickness of tissue in the same bite or clamping step where tissue thickness changes along the length of the system.

Figure 7:
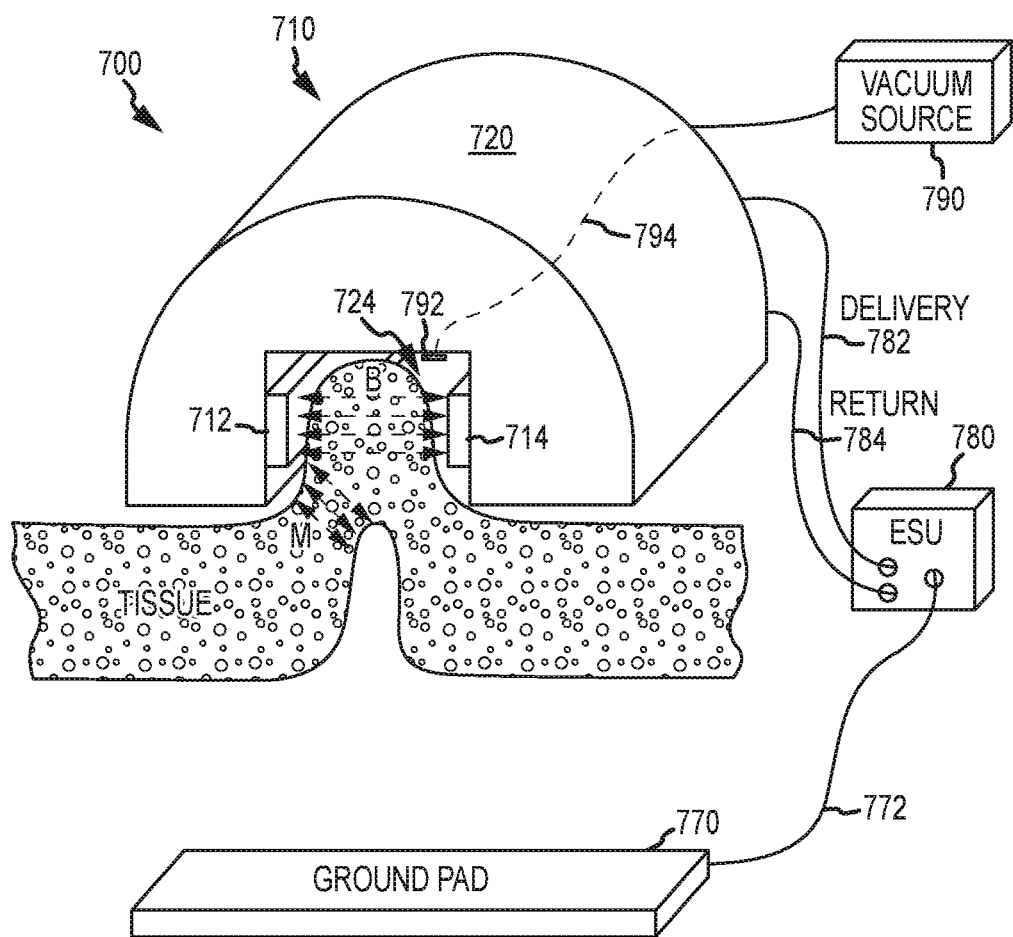
FIGS. 7, 7A, and 7B show aspects of surgical systems and methods according to embodiments of the present invention.
Figure 7A:
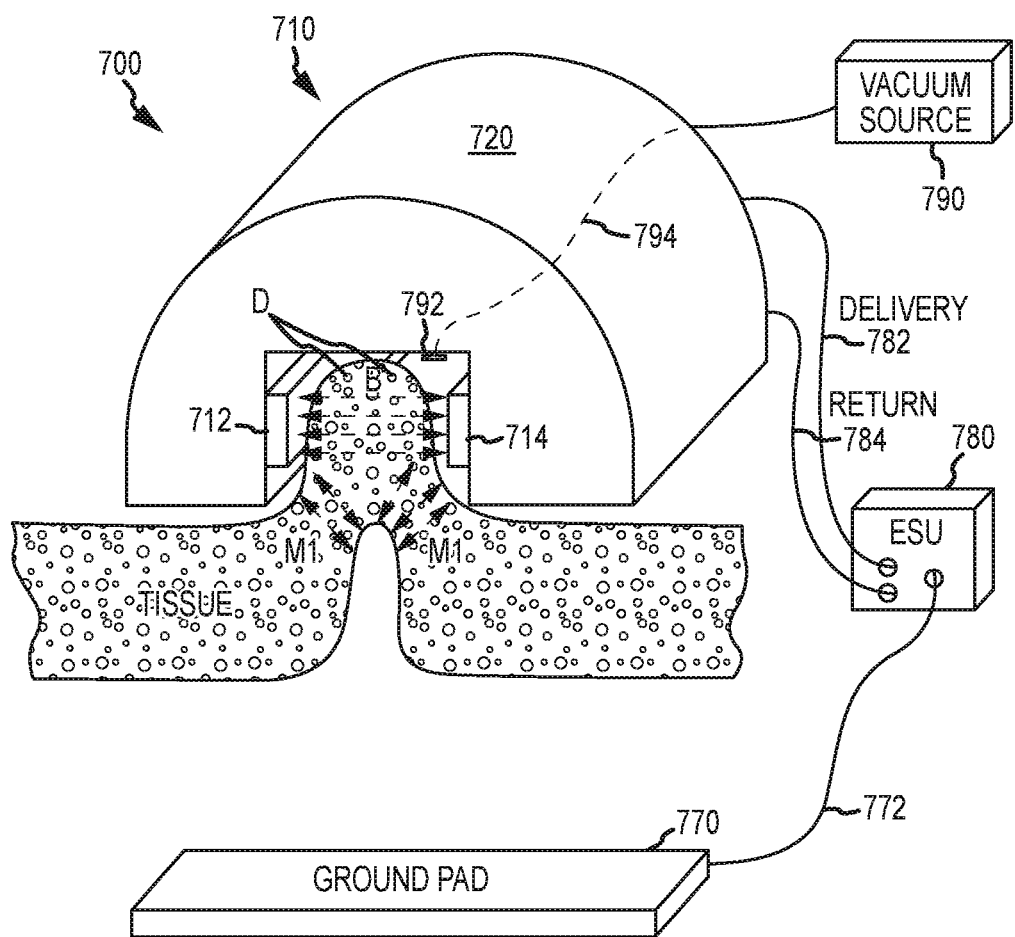
Figure 7B:
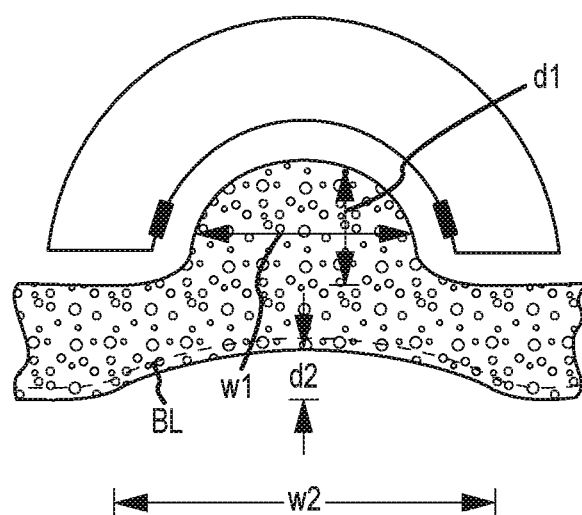

As depicted in FIGS. 7 to 7B, embodiments of the present invention encompass systems that provide a pocket, recess, cavity, or channel, which may be defined by a suction pod, ribcage mechanism, or both, into which tissue can be drawn. Relatedly, as shown in these drawings, embodiments provide techniques for drawing tissue into such recesses, optionally with the use of suction, and against or toward electrode mechanisms which are positioned therein. In some instances, such a cavity can be presented along the entire length, or a portion of the entire length, of a suction pod mechanism. Hence, the system can provide suction to the tissue along the full length, or a portion of the full length, or an electrode mechanism. Further, embodiments of the present invention encompass systems and methods that provide for the application of either monopolar ablation energy, or bipolar ablation energy, or a combination thereof. For example, in use, the system may be switched back and forth between a monopolar electrode capability and a bipolar electrode capability. In some instances, one or more temperature sensors may be located along a central inner recess of a suction pod mechanism.

Embodiments of the present invention encompass systems and methods that involve the combined or bimodal application of bipolar and monopolar ablation protocols. FIG. 7 shows a surgical system 700 that includes an ablation mechanism 710 having a first electrode assembly 712 and a second electrode assembly 714. System 700 also includes a suction stabilizer mechanism 720 coupled with or in operative association with the ablation mechanism. As shown here, suction stabilizer mechanism 720 defines a recess or cavity 724 into which patient tissue can be drawn, for example by creating a vacuum or introducing a relative negative pressure within the recess. As depicted here, system 700 includes or is in operative association with a vacuum source 790, which is in fluid communication with a vacuum port or aperture 792 via a vacuum line or passage 794. When electrodes 712 and 714 are configured as the only electrodes in the circuit serving as active and return electrodes respectively, for example by coupling them with a related power delivery and return interfaces of an electrosurgical unit (ESU) 780, system 700 can provide a bipolar current flow pathway as indicated by arrows B. When electrode 712 serves as the active electrode and a ground pad 770 serves as the return electrode, for example by coupling electrode 712 and ground pad 770 with related power delivery and return interfaces, respectively, of ESU 780, system 700 can provide a monopolar current flow pathway as indicated by arrows M. Conversely, it is understood that electrodes 712 and 714 can be operated as return and active electrodes, respectively, in an alternative bipolar configuration, and that electrode 714 can operate as an active electrode and ground pad 770 can operate as a return mechanism, in an alternative monopolar configuration.

As shown in FIG. 7A, when electrodes 712 and 714 both serve as active electrodes and ground pad 770 serves as a return electrode, for example by coupling electrodes 712 and 714 with an ESU power delivery interface and ground pad 770 with an ESU return interface, system 700 can provide a monopolar current flow pathway as indicated by arrows M1, where the current paths come from both active electrodes and flow toward the ground pad. In contrast with the monopolar flow shown in FIG. 7, when both electrodes are active as depicted in FIG. 7A, current from each of the electrodes is less focused toward the intervening location between the electrodes, and more strongly directed toward paths that extend downward and across the full tissue wall, due to the propensity of the current to maintain separate flow paths and travel toward areas of lower potential. Hence, the upper central portion of tissue D typically will be cooler during the dual active electrode monopolar modality shown in FIG. 7A, as compared with the bipolar modality. Relatedly, heating of section D during bipolar ablation will be primarily due to direct heating or conduction which is proportional to the square of the current density locally, whereas heating of section D during dual active electrode monopolar ablation will be primarily due to conduction.

Patient tissue that is not drawn into the suction stabilizer chamber or trough can be heated more effectively when current is flowing downward toward the ground pad during monopolar ablation, because it is less likely that tissue will be ablated during bipolar ablation where lesion formation occurs primarily between the electrodes within the suction stabilizer trough. Hence, for tissue outside of the suction stabilizer recess, monopolar current provides more heating to that tissue. Bipolar ablation may provide heat to this tissue outside of the stabilizer, but this is due to approximation conduction, where heat flows from the hotter tissue within the stabilizer recess to tissue outside of the recess. In contrast, monopolar ablation can deliver direct heating for this tissue.

Heat convection can play a significant role in tissue ablation and the size of the resulting lesion during monopolar and bipolar radiofrequency treatments. For example, for monopolar ablations, heat convection may be responsible for about 90% of the lesion. Similarly, for bipolar ablations, heat convection may be responsible for about 67% of the lesion. The process of heat convection can also facilitate the continuous or cumulative administration of ablation energy, as heat is convected away from the electrode where the most intense direct tissue heating occurs, and into other nearby tissue.

As tissue is drawn into the suction stabilizer channel, the tissue may be distorted. As shown in FIG. 7B, a section of tissue having a depth of d1 is drawn into the channel, leaving a corresponding tissue divot or recess having a depth of d2. In some instances, depth d1 may be twice as large as depth d2. Hence, if tissue is drawn into the stabilizer recess to a depth d1 of about 1 cm, the corresponding divot on the opposing side of the tissue may have a depth d2 about 0.5 cm. Similarly, the section of tissue drawn into the channel can have a width of w1, leaving a corresponding tissue divot or recess having a width of w2. In some instances, width d2 may be twice as large as width d1. Hence, if tissue is drawn into the stabilizer recess such that width w1 is about 0.5 cm, then the corresponding divot on the opposing side of the tissue may have a width w2 about 1 cm.

During ablation a thermal boundary layer can form along the surface of the tissue opposing the ablation electrodes. For example, as illustrated in FIG. 7B, a boundary layer BL may form along an inner section of the atrial tissue. In some cases, the boundary layer may have a thickness of about 1 mm, and due to convective cooling within the heart, the tissue temperature at boundary layer may be maintained at about 37 degrees Celsius. The phenomenon of convective cooling also may make it difficult to sufficiently heat the boundary layer BL of patient tissue. Not only is blood conductively removing heat from the boundary layer due to contact proximity, but blood is also convectively removing heat from the boundary layer as it flows away due to circulation. As the velocity of blood flowing along the boundary layer increases, the thickness of the boundary layer becomes smaller, and the thickness of tissue being heated primarily by conduction increases. When tissue has been drawn into the suction stabilizer channel so as to create a divot or recess on the opposing side of the tissue, typically there is less blood flow or movement within the resulting tissue recess, and blood tends to remain there. Hence, the effect of convective cooling by blood at the boundary layer BL is reduced.

With continuing reference to FIGS. 7 and 7A, the ablation accomplished by monopolar current M or M1 is localized in an area adjacent to the active electrode or electrodes, where the current density is higher. Due to dissipation effects, monopolar current does not ablate tissue as it travels farther beyond this area toward the ground pad. When in the bipolar configuration, the ground pad can be disconnected or electrically disassociated from the ESU, and when in the monopolar configuration, electrode 712 or 714 (FIG. 7) can be disconnected or electrically disassociated from the ESU. In some cases, bipolar current B and monopolar current M or M1 are applied simultaneously during a treatment. Ground pad 770 can be affixed or placed against an external portion of the patient's body. For example, the ground pad can be adhered to skin tissue on the patient's back. In some cases, a ground pad or mechanism 770 can be placed at a desired location within the patient's anatomy. As illustrated here, line 782 provides connectivity between the ESU and electrode 712, line 784 provides connectivity between the ESU and electrode 714, and ground line 772 provides connectivity between ground pad 770 and the ESU. By using a ground pad it is possible to achieve a certain type of tissue burn or ablation. Conversely, by not using a ground pad it is possible to achieve a different type of tissue burn or ablation. With reference to FIG. 7, it can be seen that the application of monopolar current flow, as indicated by arrows M, can be helpful in achieving transmural ablations, for example when treating tissues having greater thicknesses. Without this additional monopolar ablation, in some cases the tissue may be too thick to accomplish transmural lesions with bipolar energy between electrodes 712 and 714 alone, because although the top layer of tissue is sufficiently drawn into the suction stabilizer recess, the lower layer of tissue may remain extending outside of the recess, and therefore receive insufficient energy from the delivered ablation energy so that tissue ablation is not achieved as desired.

When bipolar and monopolar ablation is applied simultaneously, some current passes from the active electrode (e.g. 712) to the return electrode (e.g. 714), and some current passes from the active electrode (e.g. 712) to ground pad 770. As noted above, such bipolar and monopolar administration of ablation energy can be applied in an alternating fashion. For example, the ground pad can be unplugged or electrically dissociated from the ESU for application of bipolar energy. Similarly, the return electrode can be unplugged or electrically disassociated from the ESU for application of monopolar energy. In some cases, the ESU may also be referred to as a generator or a control box.

According to some embodiments, ablation treatment may switch rapidly between a bipolar ablation and a monopolar ablation during a single RF ablation application. For example, an ESU can be configured to automatically change modes between bipolar and monopolar modes, within the course of a treatment. Such switched ablation protocols can be effective in creating tissue lesions. In some cases, switching may occur at 15 second intervals or faster. In some instances, switching may occur as fast as 0.1 second intervals. Various ablation mode protocols are described in Table 1. As shown here, a treatment system can be switched between any of a variety of bipolar and monopolar operating modes.

TABLE 1

| Electrode 712 status | Electrode 714 status | Pad 770 status | Ablation Mode |
| --- | --- | --- | --- |
| switched to active | switched to active | switched to return | dual electrode monopolar |
| switched to active | switched to return | switched off | bipolar (712 to 714) |
| switched to return | switched to active | switched off | bipolar (714 to 712) |
| switched to active | switched off | switched to return | monopolar (from 712) |
| switched off | switched to active | switched to return | monopolar (from 714) |
| switched to active | switched to return | switched to return | combined bipolar and monopolar |
| switched to return | switched to active | switched to return | combined bipolar and monopolar |

When switched to an active configuration, an electrode is typically in operative association with an active channel of the ESU. Similarly, when switched to a return configuration, an electrode or pad is typically in operative association with a return channel of the ESU. When switched off, an electrode or pad can be disassociated from the active and return channels. With regard to any of the ablation modes, the power or energy delivered to each electrode can be feedback controlled based on electrode temperature. In some instances, switching can be performed by processors, electronic circuits, software, firmware, or any combination thereof.

Figure 8:
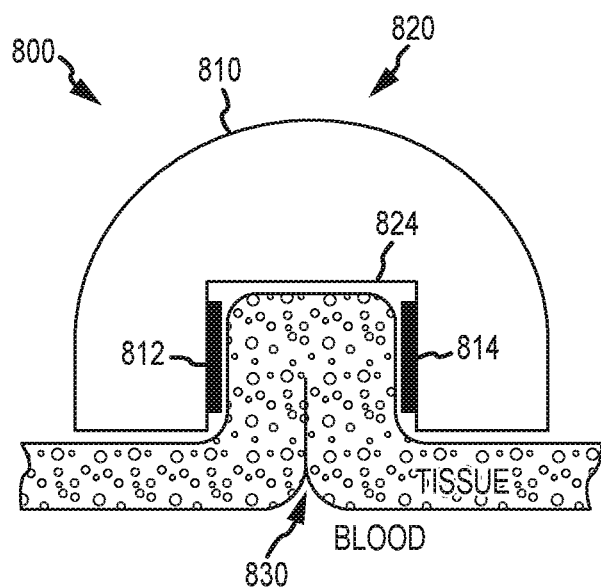
FIGS. 8 and 8A show aspects of surgical systems and methods according to embodiments of the present invention.

In some instances, embodiments of the present invention encompass systems and methods which counteract or overcome a heat sink effect, which can be caused by relatively cool blood drawing heat away from the tissue. FIG. 8 shows a surgical system 800 that includes an ablation mechanism 810 having a first electrode assembly 812 and a second electrode assembly 814. System 800 also includes a suction stabilizer mechanism 820 coupled with or in operative association with the ablation mechanism. As shown here, suction stabilizer mechanism 820 defines a recess 824 into which patient tissue can be drawn, for example by creating a vacuum or introducing a relative negative pressure within the recess. When the tissue is pulled into recess 824, it bunches and becomes more uniformly compressed. The portion of the tissue being ablated is drawn out of the blood stream, or otherwise thermally isolated from the heat sink effect caused by the blood. Hence, heat generated within the tissue via application of current is not dissipated into the blood stream, and consistent temperatures are maintained within the treated tissue. As depicted in FIG. 8, a suction pod mechanism or ribcage mechanism can provide a pocket, recess, cavity, or channel, into which tissue can be drawn. Relatedly, as shown here, embodiments provide techniques for drawing tissue into such recesses and against or toward electrode mechanisms which are positioned therein. In some instances, systems include one or more temperature sensors in association with an electrode, such as an active electrode.

Figure 8A:
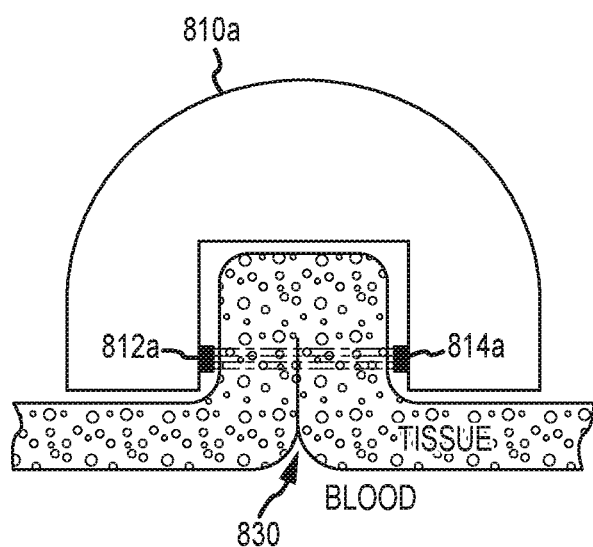

Accordingly, as shown in the FIG. 8 cross-section, tissue can be drawn and folded into the recess 824 between electrodes 812 and 814, and the folded tissue can be ablated. In some instances, the tissue is folded so as to provide a valley 830 that runs along the length of a probe assembly. Hence, there is a continuous and linear tissue apposition, whereby two sections of the same tissue are positioned in a side-by-side manner. In this way, the surgical system facilitates the formation of an overall continuous lesion. As depicted in FIG. 8A, an ablation probe assembly 810a can be configured with electrodes 812a, 814a that are disposed near the recess entrance, such that treatment of the tissue results in a lesion pattern having two parallel lines or sections (e.g. when the tissue is removed from the recess and unfolds). In comparison, a probe assembly and treatment configuration as shown in FIG. 8 can result in a single lesion line or section having a trapezoidal cross-section, with a wider length along the endocardial surface and a narrower length along the epicardial surface. Hence, depending on the geometry of the ablation probe assembly, the thickness of the tissue, or a combination of both, there may be two parallel lines epicardially and endocardially (e.g. FIG. 8A), or two parallel lines epicardially and only one endocardially (e.g. FIGS. 2D, 6B). Relatedly, in some embodiments, because of conductive heating, the lesion may spread somewhat beyond the electrode contact surface area and the two epicardial lines may merge into one. Generally speaking, clinically a wider lesion may create a more permanent conduction block; one reason being that any healing, live cell in-growth into the lesion scar, and/or remodeling over time is less likely to bridge a wider gap. In this way, two parallel ablated lines or wider ablation lesions can provide a safety feature, and relatedly, where there are double ablation lines, one lesion can compensate for a possible gap (if such occurs) in other lesion.

Figure 9:
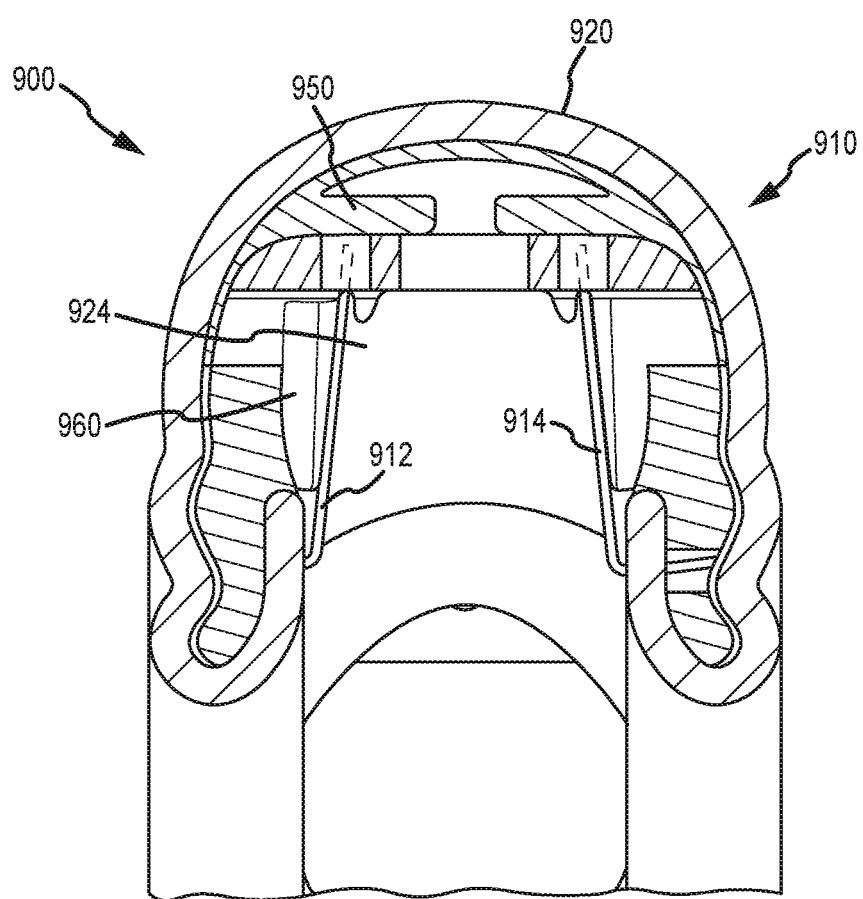
FIG. 9 shows aspects of surgical systems and methods according to embodiments of the present invention.

FIG. 9 illustrates a surgical system 900 that includes an ablation mechanism 910 having a first electrode assembly 912 and a second electrode assembly 914. System 900 also includes a suction stabilizer mechanism 920 coupled with or in operative association with the ablation mechanism. Suction stabilizer mechanism 920 defines a recess 924 into which patient tissue can be drawn, for example by creating a vacuum or introducing a relative negative pressure within the recess. As shown here, suction stabilizer 920, optionally in combination with an electrode, can provide or define recess 924 or integral lumens 950, 960 to help channel the vacuum or negative pressure and draw tissue into contact with the electrodes. Such pockets, lumens, or other surface contours or features along the inner wall or ceiling of the suction stabilizer recess, can help facilitate the administration of a vacuum or negative pressure along a desired length of the suction stabilizer, for example by preventing or inhibiting fluid flow blockages from developing at a proximal portion, which could diminish the opportunity for applying a vacuum or negative pressure at a more distal portion of the device.

Embodiments of the present invention encompass systems and methods which help to deliver and maintain vacuum or negative pressure along a length of the suction stabilizer. In some instances, embodiments provide an ablation mechanism having a first electrode assembly and a second electrode assembly, and a wide stabilizer mechanism or ribcage mechanism with a low, perforated ceiling. When vacuum or negative pressure is delivered via a port, tissue is drawn into channel. The tissue is prevented from contacting the vacuum port or entering a vacuum track, due to the presence of the perforated ceiling. In this way, the ceiling may operate as a screen. Hence, a vacuum or negative pressure can be maintained within a vacuum track without disruption from the tissue. In some instances, a perforated ceiling may include a plastic sheet having a thickness of about 0.5 mm, with multiple holes or apertures. In some instances, such perforations, apertures, or gaps may be an integral part of a ribcage mechanism. For instance, a ribcage mechanism may have a ribcage spine with a serpentine shape, and intercostal or alternating spaces between the serpentine loops provide such apertures or gaps along the length of the ribcage mechanism. A ribcage mechanism presenting a fishbone configuration can also provide such gaps or apertures.

In some instances, systems may include an ablation mechanism having a first electrode assembly and a second electrode assembly, and a stabilizer mechanism with a screen ceiling. When vacuum or negative pressure is delivered via a port, tissue is drawn into a trapezoidal channel. The tissue is prevented from contacting a vacuum port or entering a vacuum track, due to the presence of the screen ceiling. Hence, a vacuum or negative pressure can be maintained within vacuum track without disruption from the tissue. In some cases, electrode assemblies may include angled electrodes. In some instances, a system may include a narrow stabilizer mechanism.

Figure 10:
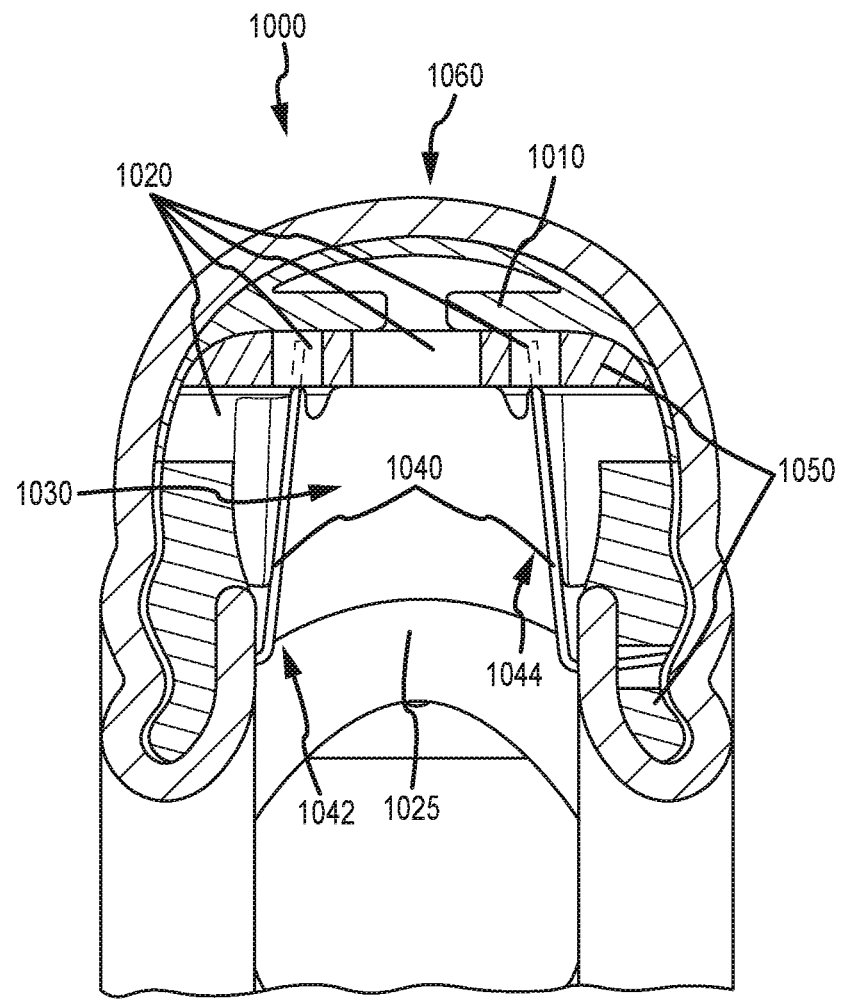
FIGS. 10 and 10A show aspects of surgical systems and methods according to embodiments of the present invention.

FIG. 10 illustrates a surgical system 1000 that includes an ablation mechanism 1040 having a first electrode assembly 1042 and a second electrode assembly 1044. The electrode assemblies can be coupled with or in operative association with a ribcage mechanism 1050. In some instances, the ablation mechanism 1040 is considered to include or incorporate the ribcage mechanism 1050. System 1000 also includes a suction stabilizer mechanism or pod 1060 coupled with or in operative association with the ablation mechanism. Suction stabilizer mechanism 1060 defines a recess 1030 into which patient tissue can be drawn, for example by creating a vacuum or introducing a relative negative pressure within the recess. As shown here, suction stabilizer 1060, optionally in combination with an electrode and/or a ribcage mechanism, can provide or define recess 1030 and/or other open spaces or lumens 1010 disposed behind the ribcage and/or electrodes, so as to help channel the vacuum or negative pressure and draw tissue into contact with the electrodes. Such pockets, lumens, or other surface contours or features along the inner wall or ceiling of the suction stabilizer recess, can help facilitate the administration of a vacuum or negative pressure along a desired length of the suction stabilizer, for example by preventing or inhibiting fluid flow blockages from developing at a proximal portion, which could diminish the opportunity for applying a vacuum or negative pressure at a more distal portion of the device. Hence, the ribcage mechanism 1050 can provide apertures, rib spacings, or openings 1020, such that when suction is applied, the vacuum or relative negative pressure is transmitted from the open spaces or lumens 1010, through the openings 1020, and into the recess 1030, where the suction or relative negative pressure operates to draw tissue into the recess as indicated by arrow 1025. Put another way, the suction can operate to evacuate air or fluid from the recess 1030, by virtue of the openings 1020 provided by a porous screen or portion or slotted structure of the ribcage mechanism 1050. Accordingly, tissue is pulled or drawn into contact with electrodes 1042 and 1044. According to some embodiments, the ribcage mechanism 1050 also provides a degree of structural rigidity, so as to help maintain the recess 1030 as a non-collapsible space when suction is applied. In this way, the ribcage structure 1050 can provide a screen or porous portion for transmitting the suction, and can also help to maintain the volume and geometry of the recess 1030 when the suction is applied.

In some embodiments, a surgical system may include a probe assembly having a non-adjustable length that can be used to form a full box lesion loop. In some embodiments, a surgical system may include a probe assembly having an adjustable length that can be used to form a full box lesion loop. In some embodiments, a surgical system may include a cinching mechanism that operates to adjust the size of a working area of the probe assembly. Such cinching techniques can be used to form full box lesion loops as well. Any of the surgical systems disclosed herein, including those providing full length probe loops and partial length probe loops, can also be used to create connecting lesions.

Figure 10A:
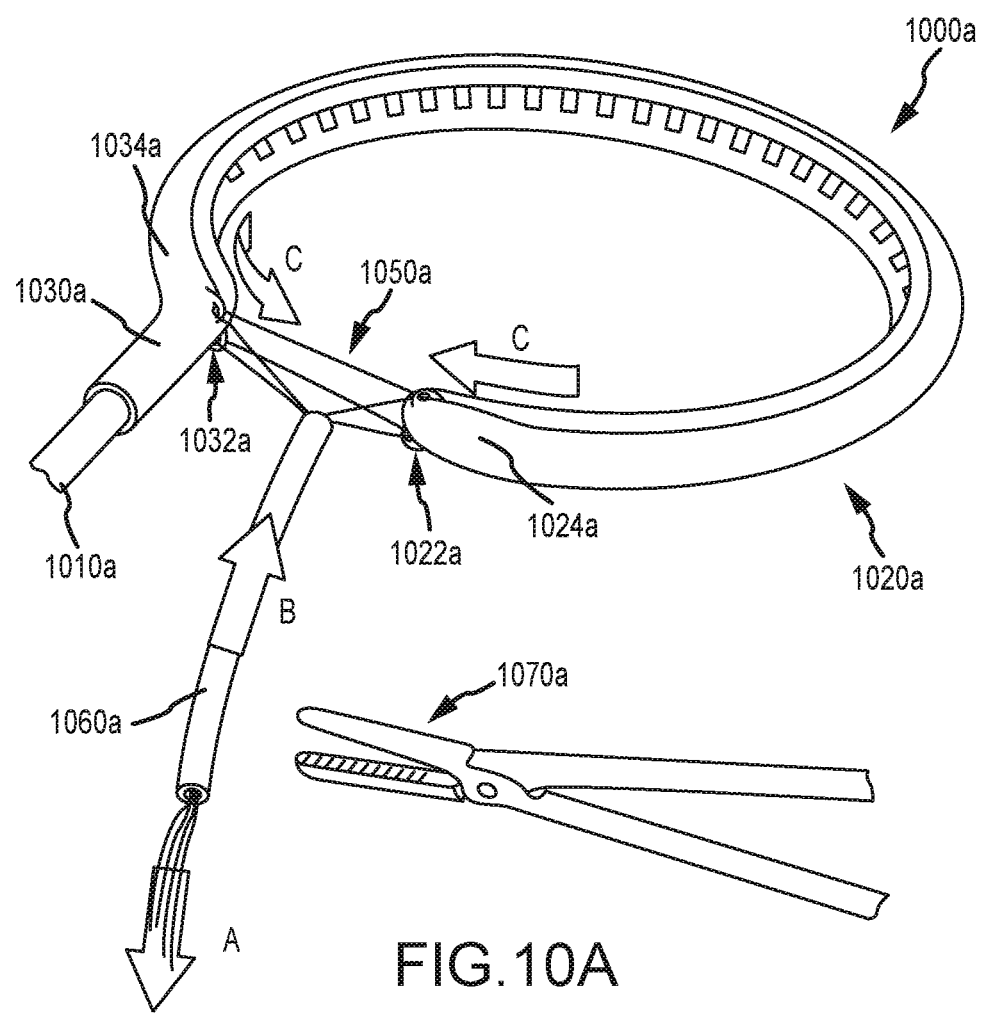

FIG. 10A depicts aspects of a cinching mechanism and method according to embodiments of the present invention. As shown here, surgical system 1000a includes a flexible tubing mechanism 1010a in operative association with a probe assembly 1020a (e.g. a long probe assembly as depicted in FIG. 14), for example via a U-joint mechanism or coupling mechanism 1030a. As described elsewhere herein, probe assembly 1020a may include an elastic pod assembly, a flexible or semi-flexible ribcage mechanism, and an electrode assembly. As depicted here, probe assembly 1020a includes one or more apertures, holes, or lacing mechanisms (e.g. loops or hooks) 1022a disposed at a distal portion 1024a of the probe assembly, and one or more apertures, holes, or lacing mechanisms (e.g. loops or hooks) 1032a disposed at a proximal portion 1034a of the probe assembly. In use, these lacing mechanisms 1022a, 1032a can be threaded with a suture or string 1050a (e.g. looping through apertures or hooks, in any imaginable sequence). The two loose ends of the suture can be threaded through a shaft or flexible tube 1060a and when pulled (e.g. arrow A) with counter-traction on the tube (e.g. arrow B), so as to cinch the ends of the probe together (e.g. arrows C). The tube can then be clamped off Rommel style with forceps 1070a so that the cinching remains tight. Hence, as depicted here, a long ablation assembly with eyelets on distal and proximal ends can be used with a cinching mechanism, for example a suture (or a pair of sutures) and a tube. The suture or sutures can be threaded through a flexible tube, then between the eyelets (in any imaginable sequence), then back through the flexible tube. As the tube is advanced and the loose ends of the threads are retracted, the proximal and distal ends of the ablation assembly are drawn together. When suction and satisfactory position is achieved, a clamping instrument can be clamped across the flexible tubing, securing and locking the suture within in its tensioned position, maintaining the cinched condition of the ablation assembly. Releasing the clamping instrument releases the suture which can be pulled out at will.

Figure 11:
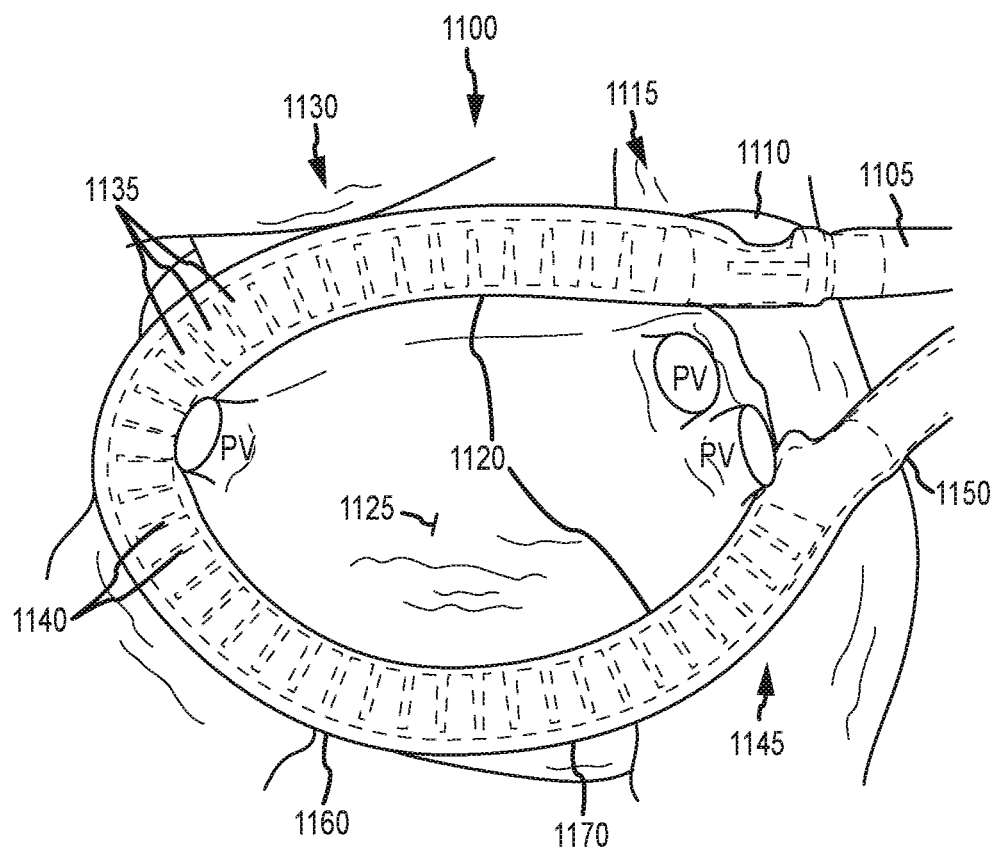
FIGS. 11, 11A, 11B-1, 11B-2, and 11B-3 show aspects of surgical systems and methods according to embodiments of the present invention.
Figure 11A:
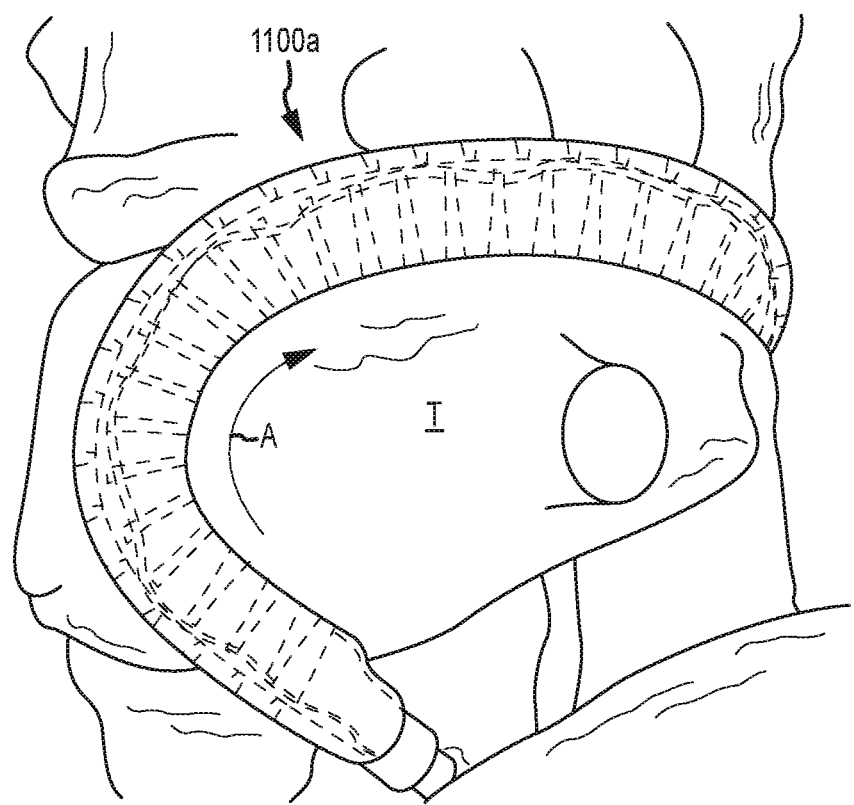
Figures 1, 11B:
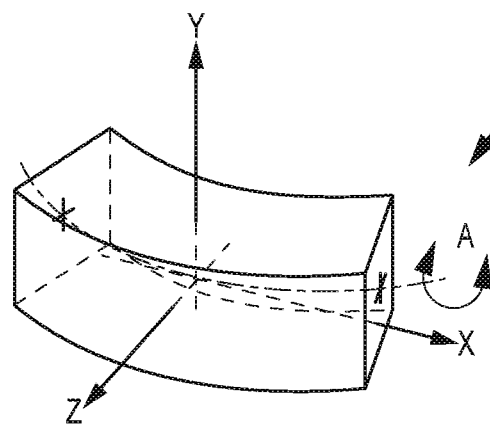
Figures 2, 11B:
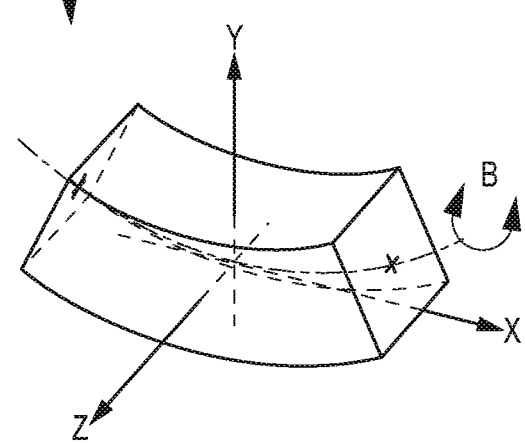
Figures 3, 11B:
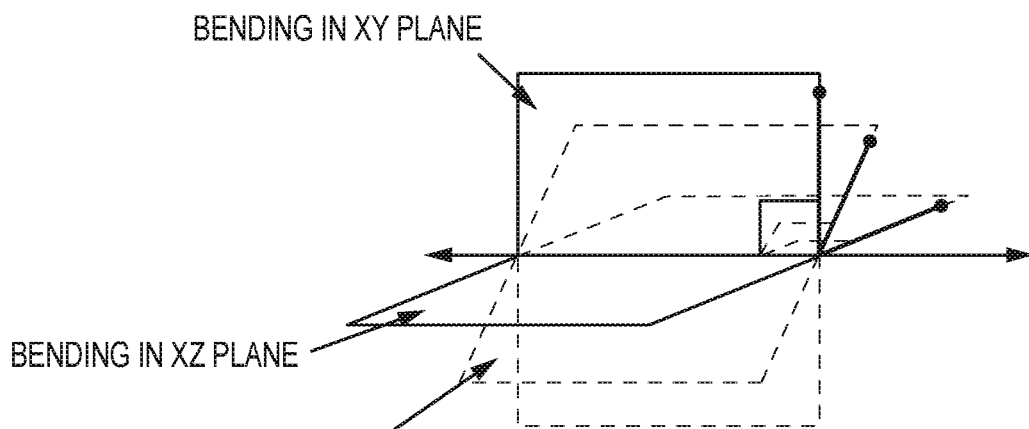

FIG. 11 depicts a surgical system 1100 according to embodiments of the present invention. Surgical system 1100 includes a probe assembly 1130 making a partial loop around an anatomical structure or tissue 1125 of a patient. The probe assembly 1130 provides a suction opening or recess that can be engaged with a portion of the tissue, thereby forming a treatment zone or area 1120 where electrodes 1135 can deliver energy to the tissue, thus forming an ablation. As shown here, a proximal portion 1145 of the probe assembly 1130 can be held in place (e.g. in contact with the patient tissue) or otherwise maneuvered by adjusting a tubing assembly 1150. For example, the tubing assembly 1150 can be used to rotate the proximal end 1145 axially into a desired orientation. In some cases, the tubing assembly 1150 is coupled with the probe assembly 1130 via a U-joint as discussed elsewhere herein. Further, as shown here, a distal portion 1115 of the probe assembly 1130 can be held in place (e.g. in contact with the patient tissue) or otherwise maneuvered by adjusting an introducer mechanism 1105. In some cases, the introducer mechanism 1105 is coupled with the probe assembly 1130 via a magnetic coupling assembly as discussed elsewhere herein. For example, the distal portion 1115 can be held in place by tension and rotationally by a magnetic coupling to the introducer 1105. As depicted here, probe assembly 1130 includes suction stabilizer pod mechanism 1160, ribcage mechanism 1170, and electrodes 1135. Ribcage mechanism 1170 can provide rib spaces 1140 between ribs of the ribcage mechanism, and these spaces can facilitate or allow contraction of the suction surface or treatment area 1120 without buckling of the suction pod mechanism or membrane 1160. In operation, the probe assembly 1130 can be used to create multiple lesions on the patient tissue. For example, the probe assembly 1130 can be placed in a first position on the patient tissue, and energy can be delivered to form a first lesion. Thereafter, the probe assembly 1130 can be placed in a second position on the patient tissue, and energy can be delivered to form a second lesion. In some instances, all active electrodes of the probe assembly can be activated to deliver an ablation. In other instances, a subset of the active electrodes of the probe assembly can be activated to deliver an ablation. In some cases, a number of electrodes can be activated to deliver an ablation which forms a lesion having a first length. In some cases, a number of electrodes can be activated to deliver an ablation which forms a lesion having a second length. In some instances, the lesion having the first length is longer than the lesion having the second length. A probe assembly 1130 may be provided as a longer length mechanism. For example, probe assembly 1130 may have a length that is within a range from about 15 cm to about 30 cm. Relatedly, probe assembly 1130 may have a length sufficient to encircle cardiac tissue about the pulmonary veins of a patient. In some cases, a probe assembly 1130 may be provided as a shorter length mechanism. For example, probe assembly 1130 may have a length that is less than 15 cm in length. Relatedly, probe assembly 1130 may have a length that is within a range from about 6 cm to about 15 cm. In some instances, a probe assembly 1130 may have a length that is about 10 cm. FIG. 11A shows a probe assembly 1100a of a surgical system applied to a tissue surface T. As depicted here, the probe assembly 1100a can bend, flex, and twist to conform with any irregular tissue geometry. Relatedly, a probe assembly 1100b can bend or flex in an XZ plane as depicted in FIG. 11B-1, in an XY plane as depicted in FIG. 11B-2, and/or any other plane illustrated by example in FIG. 11B-3. As depicted by arrows A and B of FIGS. 11B-1 and 11B-2, respectively, a probe assembly can also twist or undergo torsion about its longitudinal axis, optionally while bending or flexing at the same time. In some cases, a first portion of the probe assembly may bend with an a y-axis bending moment (either positive or negative) for example as shown in FIG. 11B-1, and a second portion adjacent the first portion may bend with a z-axis bending moment (either positive or negative) for example as shown in FIG. 11B-2. Relatedly, such first and second portions may also undergo twisting, either in the same direction (e.g. right handed), or in opposing directions (e.g. first portion with left hand twist, and second portion with right hand twist). Such bending and twisting can be achieved by the flexible nature of the probe assembly components. For example, elements of a probe assembly, such as a suction pod mechanism, a ribcage mechanism, or an electrode mechanism, can be torsionally flexible and flexurally flexible, either alone, or when present in any combination thereof. Accordingly, the suction surface of a probe assembly can be positioned in any desired out-of-plane orientation. Because a probe assembly can flex up, down, and side to side, and can also twist while bending, it is possible for a probe assembly to accommodate a suction surface to any of a variety of tissue curvatures. The path around the left atrium, for example, is generally circular but bends and twists slightly out of plane around the associated anatomical structures. Even if these were ignored there is another combination bend and roll requirement of the probe as follows: Relatedly, because of the hemispherical shape of the atrium, an ablation probe may twist along its length as if it were suctioned onto a wide cone shape, where the probe assembly is bent into a circular shape while twisting the suction plane along its full length slightly to one side.

Figure 12:
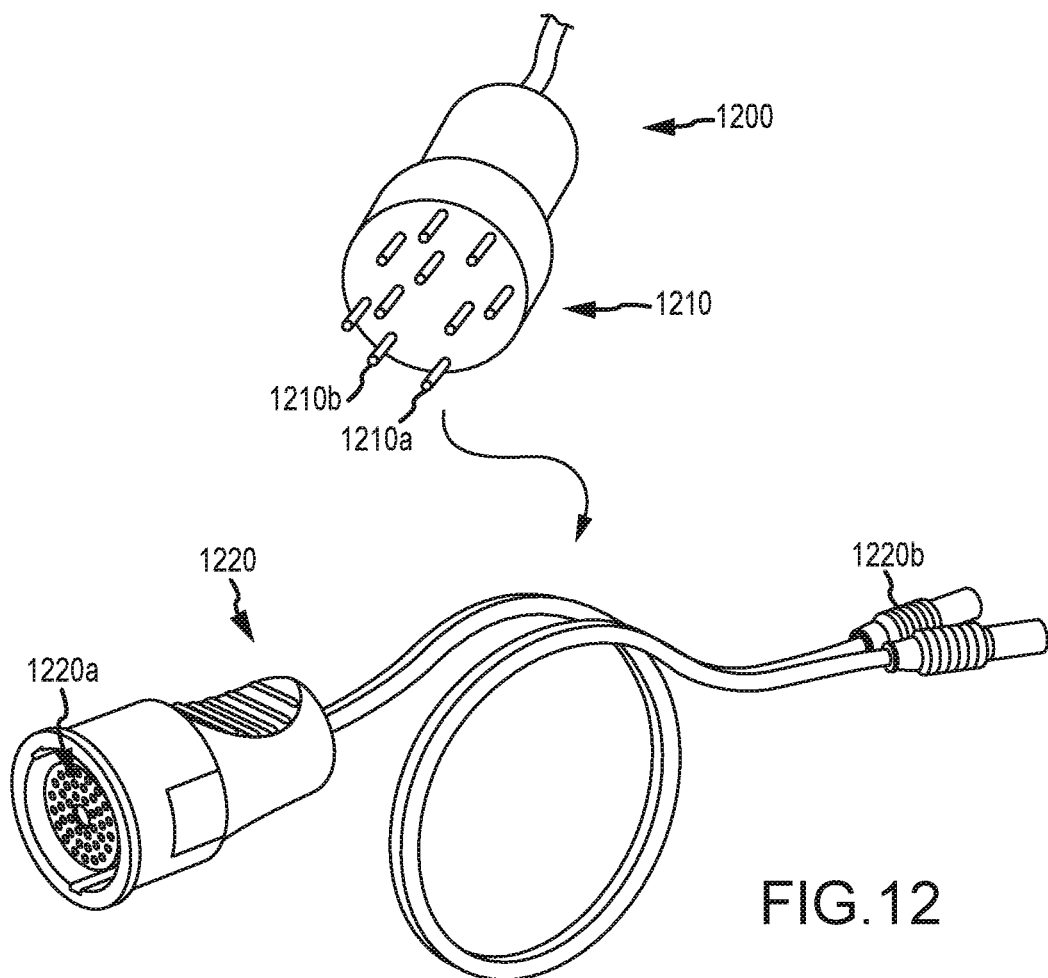

Embodiments of the present invention further encompass systems and methods for pacing patient tissue. In some instances, systems include a multifunction cable connector, which may connect various electrical components of the system with an electrosurgical unit (ESU). FIG. 12 shows an exemplary ablation device connector 1200 having one or more pins 1210 configured to interface with a generator or ESU (not shown). Device connector 1200 may include specific pins 1210a, 1210b that connect with pacing electrodes or leads on a treatment device, for delivering a pacing treatment from the generator to the patient. Optionally, systems and methods may include the use of an adapter 1220 having a female section 1220a (e.g. having hollow receptacles, pin holes, or slots) that interfaces with pins 1210 and a male section 1220b (e.g. having pins) that interfaces with the generator or pacemaker. Relatedly, distal leads can be wired to or coupled with a distal section of the device and terminate in different pins distinct from the RF wiring of the distal electrodes. An ablation generator or ESU can have an integral pacing function. Alternatively, an adaptor connector can be configured identical to a female connection of the ablation generator for insertion of the probe cable with positive and negative male pins compatible with an external pacemaker for subsequent suction applied pacing following an ablation procedure.

Figure 12A:
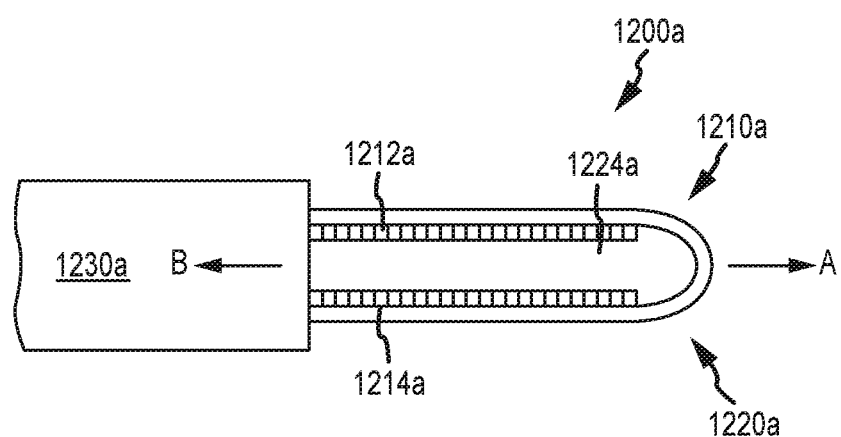

Optionally, systems can be configured to provide a linear array with the same or a different device in various lengths. By withdrawing the probe into a housing so that only the distal portion of the electrode is exposed, the same device may be used to achieve bipolar pacing with a suction applicator to ensure tissue contact. FIG. 12A illustrates a surgical system 1200a that includes an ablation mechanism 1210a having a first electrode assembly 1212a and a second electrode assembly 1214a. In some instances, either or both of the electrode assemblies may include between about 2 and 3 electrodes. System 1200a also includes a suction stabilizer mechanism 1220a coupled with or in operative association with the ablation mechanism. Suction stabilizer mechanism 1220a defines a recess 1224a into which patient tissue can be drawn, for example by creating a vacuum or introducing a relative negative pressure within the recess. Suction stabilizer mechanism 1220a can have a length within a range from about 4 cm to about 8 cm. In use, system 1200a can provide for the formation of transmural lesions, without bending at sharp angles. For example, suction stabilizer mechanism 1220a can maintain suction when bent to a radius of curvature that is less than about 3 cm. As shown here, system 1200a can be at least partially housed within, and configured to translate relative to, a delivery tube 1230a. For example, system 1200a can be extended outward from the tube (e.g. through and/or away from a distal aperture) as indicated by arrow A, or withdrawn toward the inside of the tube as indicated by arrow B. The exposed electrode sections that extend out of the delivery tube can be used to deliver ablation treatment to the patient, whereas the covered electrode sections within the delivery tube are prevented from contacting the patient tissue. Hence, use of the delivery tube facilitates the administration of lesions having a variety of lengths, based on the adjustable length of the exposed electrode sections. Use of distal electrode portions or leads can facilitate the application of bipolar pacing to the patient tissue. The adjustability of the exposed electrode length in surgical system 1200a makes this embodiment well suited for the application of connecting lesions to patient tissue. In some cases, distal spot pacing electrodes or pacing electrodes electrically separated from the ablation electrodes may be used for pacing.

The pacing ability provided by the leads can be used to artificially pace or stimulate the heart as desired, to evaluate the transmurality of a lesion. For example, some techniques involve the application of a circular ablation that surrounds the bases of the patient's pulmonary veins, in an attempt to create a transmural ablation. Pacing electrodes or leads can be placed within the boundaries of this ablation, and a strong pulse can be delivered to a central location via the leads. Resulting cardiac contraction that is confined to tissue located within the circular ablation, and that occurs at the same beat or pulse rate as the delivered pacing stimulus, is indicative of a transmural lesion or conduction block. Alternatively, pacing electrodes can be placed outside the boundary of the circular ablation for delivery of a stimulation pulse. If the resulting cardiac contraction is limited to the exterior of the circular ablation, and does not occur within the inside of the ablation boundary, it is possible to conclude that a complete lesion or conduction block is formed.

Pacemaker devices often do not provide a high current drive capability. For example, typical pacemakers may be configured to drive about 10 milliamperes. According to embodiments of the present invention, tissue treatment systems can be configured to deliver about 10 milliamperes during a tissue pacing or stimulating protocol, and about 1 ampere for a tissue heating or ablation protocol. When a delivery tube or sheath is positioned to a sufficiently distal location along a stabilizer mechanism, the surface area of exposed electrodes can be relatively low. Hence, low voltage can be applied via this low surface area as part of a pacing procedure. In some instances, 10V and 10 milliamperes can be delivered for high intensity pacing. A delivery tube or sheath can also be retracted, thus exposing a greater surface area of electrodes. In such configurations, higher levels of energy can be administered so as to create lesions. For example, about 100 Volt and 1 ampere can be delivered for ablation. By sliding the delivery tube or sheath along the length of a stabilizer mechanism, it is possible to adjust the exposed surface area of electrodes. Similarly, by maneuvering an introducer and/or tubing mechanism as shown in FIG. 11, it is possible to adjust the positioning of electrodes on the patient tissue. The sheath and stabilizer mechanism shown in FIG. 12A can be constructed of or include material such as various elastomeric polymers, such that the sheath and stabilizer mechanism slide easily along one another. For example, the sheath may be constructed of silicone, and the stabilizer pod may be constructed of polyurethane. In some cases, both components are constructed of or include a soft durometer polyurethane. It is also helpful that the materials used ensure that vacuum administered through the suction stabilizer can operate to form and maintain a seal between the sheath and stabilizer pod. Exemplary elastomeric polymers provide electrical and thermal insulative properties which are helpful in carrying out the methods described herein. Suction or vacuum administered through a suction stabilizer can operate to reliably attach the suction stabilizer to both the sheath and the patient tissue. Hence, the sheath can be constructed with the appropriate dimensions and curvature so that it forms a seal with the stabilizer mechanism, and provides an interface that approximates tissue during the ablation. When the sheath is advanced toward the distal end of the stabilizer, the treatment system provides a set of small tip electrodes which pace tissue reliably when energized, because the electrodes are securely engaged with the tissue as a result of the suction. By providing a sheath that can be adjustably positioned relative to the suction stabilizer, the treatment system can be configured to switch between an ablation delivery mode and a pacing delivery mode, during the course of a single treatment.

Because some surgical systems can be configured to present shorter or longer exposed ablation element segments, in addition to providing a pacing function, such systems may also be well suited for creating variable length lesions and connecting lesions, such as those described in U.S. patent application Ser. Nos. 12/124,743 and 12/124,766 filed May 21, 2008, the contents of which are incorporated herein by reference. By covering a large portion of the electrodes, and leaving exposed a set of small tip electrodes, it is possible to adhere these small tip electrode configurations to the heart and perform a pacing procedure with them. The distal sections of electrodes can be placed on the inside of a lesion boundary, or on the outside of a lesion boundary, following formation of the lesion, and can be used to confirm whether a pacing stimulus applied by the electrodes paces cardiac tissue on the other side of the lesion. Whereas relatively large voltages and amperages are applied through the electrodes during an ablation procedure, much lower voltages and amperages are applied through the same electrodes during the pacing procedure. In some instances, the amount of exposed surface area of electrodes can be about 10 mm$^2$ or less.

FIG. 12B shows aspects of a surgical system 1200b according to embodiments of the present invention. Surgical system 1200b includes a probe assembly 1210b having a stabilizer pod mechanism 1220b, a ribcage mechanism 1230b, and an electrode assembly 1240b. Further, surgical system includes a sheath 1250b and a support mechanism or distal probe capture mechanism 1260. As shown here, support mechanism includes two pacing electrodes 1262b and 1264b. Hence, embodiments of the present invention encompass surgical systems having a probe delivery push tube sheath and a probe assembly with an internal suction surface. In some instances, systems may also include a distal probe capture mechanism or support mechanism. In some instances, a probe delivery push tube sheath may include a separate lumen for a retrieval device such as a capture mechanism.

Additional exemplary probe delivery push tube sheath configurations which are well suited for use with the surgical systems disclosed herein are described in US Patent Publication Nos. 2008/0294154 and 2009/0048591, the contents of which are incorporated herein by reference for all purposes. In some cases, a probe delivery push tube sheath may include a soft or hard probe alignment tip.

FIG. 13 depicts aspects of a surgical system 1300 according to embodiments of the present invention. Surgical system 1300 includes a short probe assembly 1370 having a stabilizer pod mechanism 1345, a ribcage mechanism, and an electrode assembly 1325. Further, surgical system includes tubing assembly 1340 coupled with the probe assembly 1370 via a U-joint mechanism 1335. Such surgical systems are well suited for use in creating connecting and right side lesions. Short probe assembly 1370 has an active electrode set that includes two electrodes 1320, 1315 on an active side 1353 of the probe assembly. An indifferent or return electrode is hidden from view on a return side 1355 of the probe assembly 1370. As shown here, probe assembly 1370 includes a distal section 1302 and a proximal section 1304. Each of the distal section 1302 and the proximal section 1304 include tissue transition ingress features (i.e. distal ingress feature 1305 and proximal ingress feature 1306) that allow tissue to move from a relatively flat condition (e.g. outside of the treatment tissue area) to an enfolded condition (e.g. at the treatment tissue area). The distal portion 1302 of probe assembly 1370 includes grab tabs 1360 that can be grasped for maneuvering the probe assembly. The distal portion 1302 of probe assembly 1370 also includes a magnetic housing 1365 having a profile that allows the housing to be indexed rotationally with an introducer. The suction stabilizer pod mechanism 1345 includes rolled over edges 1310 that allow easy tissue ingress and egress into the suction recess and inter-rib webs 1350 that hold the rolled edges down and keep tissue out of spaces between tines of the electrodes 1325. U-joint mechanism 1335, which couples a distal section of tubing assembly 1340 with a proximal section 1304 of probe assembly 1370, can operate to help transmit torque forces, axial forces, suction, and electrical wires between the tubing assembly and probe assembly.

Figure 13A:
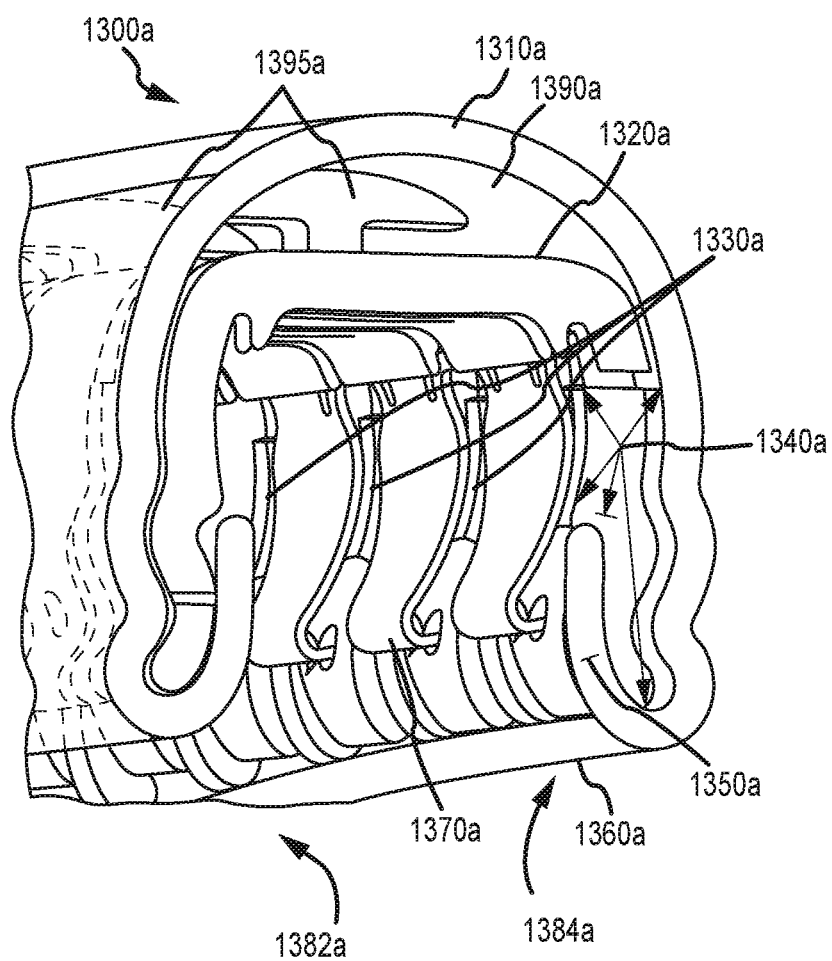

FIG. 13A shows aspects of a probe assembly 1300a according to embodiments of the present invention. As depicted here, probe assembly includes a suction pod mechanism 1310a, a ribcage mechanism 1320a housed by the suction pod mechanism, and an electrode mechanism 1370a. Such components can be made or constructed from a variety of materials. For example, suction pod mechanism 1310a may include or be constructed of an elastic material or composition, such as silicone, polyurethane, polycarbonate, another suitable polymer, or combination of polymers or the like. Ribcage mechanism 1320a may include or be constructed of a flexible or semi-flexible non-conductive material or composition. For example, a ribcage mechanism may include any of a variety of synthetic polymers, thermoplastic polymers such as polycarbonate, or another suitable plastics, either alone or in combination. Electrode mechanism 1370a may include or be constructed of a conductive material or composition, such as platinum, platinum iridium, stainless steel, gold, silver-silver chloride, nickel coated copper, or other non-toxic metals. As shown here, probe assembly 1300a may also include webs 1340a, which may be part of or extensions of suction pod mechanism 1310a, which are positioned between intercostal spaces or gaps of the ribcage mechanism, and also in spaces 1330a between individual tines of the electrode mechanism. For example, webs 1340a may extend from the suction pod mechanism, through gaps in the ribcage mechanism, and protruding out to or flush with the inner surface of the electrodes. Such webs can help to keep tissue out of spaces between the electrode tines, for example when suction is administered to the tissue via the probe assembly. Suction pod assembly 1310 also includes a rolled over edge 1350a that allows easy tissue ingress and egress. For example, when suction is applied, tissue can be drawn into a recess 1360a which is defined by the probe assembly. Conversely, when suction is discontinued, tissue can exit the recess.

Hence, embodiments of the present invention encompass surgical systems that include a stabilizer or guide mechanism defining an inner recess 1360a, and an ablation mechanism disposed within the inner recess 1360a of the stabilizer or guide mechanism. The ablation mechanism having a first electrode side 1382a and a second electrode side 1384a opposing the first electrode side. As shown here, electrode 1370a is disposed along second electrode side 1384a. The ablation mechanism also includes another electrode mechanism (not shown) disposed along first electrode side 1382a. The ablation mechanism is to receive a portion of the tissue between the first electrode side 1382a and the second electrode side 1384a. In some instances, a stabilizer mechanism may include a pod assembly 1310a coupled with a ribcage mechanism 1320a. In some instances, an ablation mechanism may include a ribcage mechanism 1320a coupled with an electrode mechanism (e.g. electrode 1370a). In use, the surgical system or treatment probe assembly can be placed at or near the tissue of a patient. A vacuum can be delivered through the stabilizer mechanism, for example along a dorsally located channel, lumen, or space 1390a. The vacuum or suction can be transmitted through intercostal spacings or gaps of the ribcage mechanism and/or electrode, so as to draw a portion of the patient tissue into the ventrally located inner recess 1360a, and between the first electrode side 1382a and the second electrode side 1384a. A treatment procedure, which may include a pacing protocol and/or an ablation protocol, can be administered to the tissue via the ablation probe assembly 1300a. As depicted here, the probe assembly 1300a may also include a vertebral ridge or protrusions 1395a, which operate to prevent or inhibit dorsal space 1390a from collapsing when suction is transmitted therethrough. As shown here, vertebral elements 1395a may be present as dorsally extending projections of ribcage mechanism 1320a.

FIG. 14 depicts aspects of a surgical system 1400 according to embodiments of the present invention. Surgical system 1400 includes a long probe assembly 1470 having a stabilizer pod mechanism 1435, a ribcage mechanism, and an electrode assembly. Further, surgical system includes tubing assembly 1430 coupled with the probe assembly 1470 via a U-joint mechanism 1425. Such surgical systems are well suited for use in creating full loop lesions. Long probe assembly 1470 has an active electrode set that includes seven electrodes (represented by bars 1415) on an active side 1453 of the probe assembly. Long probe assembly 1470 also includes an indifferent or return electrode (represented by bar 1445) on a return side 1450 of the probe assembly 1470. As shown here, probe assembly 1470 includes a distal section 1402 and a proximal section 1404. Each of the distal section 1402 and the proximal section 1404 include tissue transition ingress features (i.e. distal ingress feature 1405 and proximal ingress feature 1406) that allow tissue to move from a relatively flat condition (e.g. outside of the treatment tissue area) to an enfolded condition (e.g. at the treatment tissue area). The distal portion 1402 of probe assembly 1470 includes grab tabs 1460 that can be grasped for maneuvering the probe assembly. The distal portion 1402 of probe assembly 1470 also includes a magnetic housing 1465 having a profile that allows the housing to be indexed rotationally with an introducer. The suction stabilizer pod mechanism 1435 includes rolled over edges 1410 that allow easy tissue ingress and egress into the suction recess and inter-rib webs 1440 that hold the rolled edges down and keep tissue out of spaces between tines of the electrodes. U-joint mechanism 1425, which couples a distal section of tubing assembly 1430 with a proximal section 1404 of probe assembly 1470, can operate to help transmit torque forces, axial forces, suction, and electrical wires between the tubing assembly and probe assembly. According to some embodiments, a probe assembly may include multiple active electrodes such as electrodes 1415 shown in FIG. 14. In some instances, a probe assembly may include 6 or more active electrodes, for example.

With returning reference FIG. 1D, a serpentine ribcage mechanism 120d can provide spaces 121d (e.g. intercostal spacings or gaps) along the serpentine spine between ribs 122d, and such spaces 121d between ribs 122d allow for flexibility along the length of the ribcage mechanism. Further, such spaces 121d between the ribcage ribs (and electrode tines) allow suction pressure to be maintained outside and along the full length of the inner chamber or recess of the probe assembly, and also allow this suction as provided by a suction source to be transmitted through the ribcage mechanism so as to communicate directly with the inner recess. Screened or perforated ceiling members, which typically include a nonconductive material such as plastic, can prevent or inhibit tissue from going too far into the stabilizer recess, thus inhibiting occlusion of the suction pathway. The maintenance of suction or vacuum along the entire length of the suction pod or ablation device assembly can be ensured using such screening to prevent tissue from occluding the suction channel. The effective depth of the channel within the suction pod can be determined by the depth at which the screening is placed within the suction pod structure. The space between the screen and the central backbone body of the suction stabilizer provides an unencumbered channel for the suction to be transmitted all along the length of the stabilizer or ablation device. Such screen or perforated ceiling members are well suited for use with a variety of surgical treatment systems. In some instances, such suction transmission features can be accomplished with a serpentine or fishbone ribcage mechanism as discussed elsewhere herein.

Treatment devices can be constructed in different lengths and configuration. For example, some systems may include a relatively longer treatment device having a flexible probe assembly or pod type suction stabilizer, and some systems may include a relatively shorter treatment device having a short segment type suction stabilizer. Each of these devices can be applied to patient tissue via suction. In some instances, a surgical system may include an ablation mechanism having a first electrode assembly and a second electrode assembly, and a suction stabilizer mechanism coupled with or in operative association with the ablation mechanism. In some cases, either or both of the electrode assemblies can include about five to ten electrodes (see e.g. FIG. 14). Relatedly, some system embodiments may include a probe assembly having more than one active, temperature controlled electrode, but less than 6 active electrodes (see e.g. FIG. 13).

Individual active electrodes can have a length between about 2 cm and about 4 cm. As described elsewhere herein, embodiments of the present invention encompass systems and methods for administering ablation energy (e.g. radiofrequency energy) in a temperature controlled manner, such that temperature control can be used to maintain tissue at desired temperatures when producing a lesion or lesion set. According to some embodiments, a shorter electrode length may enhance the resolution of power delivered to each electrode of an electrode set, with regard to tissue variations that may be present along the length of a probe assembly. For example, some tissue may have a covering of fat, or may have a variable thickness profile where one section is thicker or thinner than an adjacent section. Similarly, some portions of tissue may be more affected by rapidly moving blood on the other side of the tissue wall which can act as a more effective heat sink. By providing electrodes of a shorter length within an electrode set, it is possible to accurately adjust the power profile or amounts at a locally or finely resolved level, so as to maintain a desired tissue temperature for lesion creation along a length of the probe assembly. Exemplary probe assemblies may include individual electrical connections and monitoring for individual electrodes of an electrode set. In some instances, a single return electrode can be equal or similar in length to a corresponding set of multiple active electrodes. In some instances, a return electrode may be several times longer than a single active electrode from a set of multiple active electrodes. the active electrodes. A suction stabilizer pod or mechanism can define a recess into which patient tissue can be drawn, for example by creating a vacuum or introducing a relative negative pressure within the recess. In some instances, a system can be wrapped or cinched around a patient tissue structure, such as the patient's heart or pulmonary veins. By advancing a trocar or tube along a length of the system, or by maneuvering a tubing assembly and introducer mechanism (see e.g. FIG. 11), it is possible to tighten or snug the ablation mechanism and suction stabilizer mechanism against the patient tissue. Use of a lead line can help to keep a distal portion of the suction stabilizer in close proximity with a more proximal section of the suction stabilizer. The circumference or diameter of the belt loop system configuration can be adjusted as desired to accommodate any of a variety of patient tissue sizes and shapes. As with other embodiments described herein, a surgical system can be used to produce linear lesions or encircling lesions around tissue structures such as one or more pulmonary veins, for example by wrapping or cinching the device about the patient's heart in the appropriate position. Hence, surgical systems may include a cinching mechanism to allow the circumference of the ablation mechanism to be adjustable to the tissue structure being ablated. A cinching mechanism may be facilitated by fixing the distal end of the suction stabilizer or belt and retracting the proximal end or by a separate mechanism that cinches both the distal and proximal sections of the suction stabilizer. Exemplary cinching and loop locking mechanisms and related techniques which are well suited for use with embodiments of the present invention can be found in US Patent Publication Nos. 2008/0294154 and 2009/0048591, the contents of which are incorporated herein by reference for all purposes. In some instances, a suction stabilizer mechanism is sufficiently flexible to achieve a small radius of curvature for wrapping about or interfacing with acute tissue surfaces. For example, the suction stabilizer mechanism can be configured to maintain suction onto the tissue when subjected to a bend having a radius of curvature of 1 cm or larger. In some cases, a suction stabilizer mechanism has a preformed shape or bend. In some cases, a suction stabilizer mechanism has no preformed shape or bend.

With returning reference to FIG. 11A, portions of ablation assembly 1100a having a small radius of curvature and/or which are out of plane with adjacent portions of the ablation assembly can be translated along the length of the probe assembly so that the probe assembly can hug or conform with irregular and out-of-plane curves of a tissue path, even as the probe assembly is advanced along the path as indicated by arrow A. In some instances, the ablation assembly may be advanced along a circular path. In some instances, the ablation assembly may be advanced along a non-circular path. Accordingly, embodiments of the present invention provide probe assemblies that are configured to conform to any of a variety of non-uniform or irregular tissue geometries or surfaces.

With returning reference to FIG. 11, in some instances, a stabilizer mechanism can have a length within a range from about 15 cm to about 30 cm, and can be configured to create a box lesion completely around or nearly completely around all four pulmonary veins (PV) while maintaining contact along that entire length. Hence, a stabilizer mechanism can flex and adhere via suction to a long section of tissue. In some instances, a stabilizer mechanism is configured to bend at a minimum radius of curvature of about 1.5 cm or 0.5 inches as it approaches or approximates the based of the left pulmonary veins during a surgical treatment. The stabilizer mechanism may also rotate at various angles about a longitudinal axis. Optionally, the stabilizer mechanism can be introduced through the right side of a patient, wrapped or guided around the based of the left superior pulmonary veins on the left atrium near the left atrial appendage, and positioned around the left atrium, encircling the inferior pulmonary veins, changing its angulation and rotation in a non-planar path. As described elsewhere herein, a probe assembly can be provided in a non-adjustable length sufficient to create a full box lesion on a patient tissue. Relatedly, a probe assembly can be provided with a cinching mechanism that operates to adjust the length of an exposed portion of an electrode assembly, and such probe assemblies can be used to form a full box lesion on a patient tissue as well.

Suction stabilizer or pod mechanisms having various geometric configurations can be incorporated in certain system and method embodiments of the invention. In some instances, a suction stabilizer mechanism can include a first slot or lumen that houses wiring which connects a first ablation mechanism with an ESU, and a second slot or lumen that houses wiring which connects a second ablation mechanism with the ESU. In some embodiments, such as those which may be exemplified by FIG. 9, some or all of the ablation mechanism wiring (which provides electrical connectivity between an ESU and electrodes 912, 914, is contained in a suction space 950 on both right and left sides, sharing the space with the suction function. In some instances, the wiring slot or lumen can be potted after the wiring is in place. Optionally, steerable cable members can be housed within the slots or lumens.

Exemplary embodiments provide surgical systems having an ablation mechanism with a first electrode assembly and a second electrode assembly, and a suction stabilizer mechanism coupled with or in operative association with the ablation mechanism. In some instances, treatment systems can include or operate in association with a clamping mechanism (see, e.g. FIG. 17), which can be configured to track along a suction stabilizer mechanism and promote tissue compression. For example, a suction stabilizer mechanism may include a first side rail and a second side rail, and a clamping instrument can operate to engage one or both of the side rails. The clamping instrument, in combination with the side rails, can help to maintain contact between the stabilizer mechanism and the patient tissue. In some cases, a roller device can be used to enhance the interface between the stabilizer and patient tissue. A clamping mechanism can operate to urge the first side rail toward a second side rail, or to urge second side rail toward first side rail, or both. In some instances, the side rails and the clamping instrument can be used to clamp a linear section of tissue between the electrodes.

In some instances, a suction stabilizer mechanism may include a first side rail and a second side rail, and the clamping instrument can operate to engage one or both of the side rails. Electrode assemblies of the system can present an angled or wedged configuration, such that opposing faces of the electrodes define an angle or wedge. In some instances, opposing faces of two electrodes can present a parallel or substantially parallel alignment configuration. When a system is in a clamped configuration, tissue can be maintained in place by both vacuum and the clamping force. In this way, the side rails and the clamping instrument can be used to clamp a linear section of tissue between the electrodes.

According to some embodiments, a bipolar epicardial transmural ablation system, can be placed on the patient tissue, and the electrodes may form a seal around the pod. Suction can be applied, thereby attaching or approximating tissue with the ceiling of the pod and raising the endosurface. As control rods are squeezed together, control arms lift the pod and tissue to appose inner tissue surface. The system may provide current flow between electrodes across folded tissue. An exemplary system may include a suction pod, two control arms, two control rods, an electrode pair and associated wiring, a suction pod lift point, suction inlets on the inside of the pod and optionally at the end of the pod, and posts or ribs on the ceiling of the suction pod to help maintain suction on tissue in a manner similar to that described with regard to the screen ceiling. Handles can be used to actuate the control rods and arms, in a parallel-action manner. The lower margins of the suction pod can be squeezed together to fold the tissue while the suction pod lifts and holds the tissue between the sides of the pod. The two rods along the side of the system present a structure similar to that of a bicycle chain with the axis of the links running across, side to side, that allow a curve to be formed while maintaining lateral stability. The system can be configured as a short connecting lesion device or as a long loop device as described elsewhere herein. Further, the system can accommodate differing thicknesses of tissue.

According to some embodiments, a treatment system may include a bipolar ablation suction pod with a flexible spine for curved surfaces. For example, a system can present a concentric tube construction that can be actuated to help approximate the electrodes with patient tissue. The lower margins of the suction pod can be squeezed together to fold the tissue while the suction pod lifts and holds the tissue between the sides of the pod. The system can be configured as a short connecting lesion device or as a long loop device as described elsewhere herein. The system can accommodate differing thicknesses of tissue, and further, can accommodate different thickness of tissue in the same bite or clamping step where tissue thickness changes along the length of the system.

FIG. 15 shows a cross-section view of a probe assembly 1510 of a surgical system 1500 according to embodiments of the present invention. As depicted here, probe assembly 1510 includes a stabilizer mechanism 1520, an ablation mechanism 1530 having a ribcage mechanism 1540 coupled with a first electrode assembly 1550 (e.g. active) and a second electrode assembly 1560 (e.g. return). The stabilizer mechanism 1520 can be constructed of or include a soft elastic material or membrane. The ribcage mechanism 1540 can provide a stiffer structural element for supporting the electrode assemblies 1550, 1560 and for preventing collapse of the stabilizer mechanism 1520 during use, such as when suction is applied so as to draw tissue into or toward a recess 1522 defined by the stabilizer mechanism. In many instances, electrode mechanism 1550, 1560 may also contribute to the structural support provided by the ribcage mechanism, such that the combined presence of the ribcage mechanism and one or more electrode mechanisms inhibit or prevent collapse of the stabilizer mechanism 1520 during use, such as when suction is applied so as to draw tissue into or toward a recess 1522 defined by the stabilizer mechanism. Electrode assemblies 1550, 1560 can be spaced apart from each other by a distance D, which may be within a range from about 4 mm to about 6 mm. In some instances, distance D is within a range from about 2 mm to about 10 mm. In some instances, distance D is about 6 mm. As depicted here, tissue having a first portion thickness T1 and a second portion thickness T1 can be drawn into the recess 1522. In some instances, T1 and T1 may each be about 2 mm. In many cases, T1 and T1 are about the same thickness. In some cases, T1 may have a different thickness than T2. For example, where cardiac tissue presents one or more trabeculae, or where there are other rapid local tissue thickness changes, T1 and T2 may differ up to 50% or more. Atrial tissue thickness can range from about 1 mm to about 12 mm, or more where greater amounts of fat tissue are present. Myocardial tissue thickness can range from about 2 mm to about 5 mm, or more where greater amounts of fat tissue are present. Surgical system and method embodiments of the present invention are well suited for use in treating such tissues. In some embodiments, surgical system 1500 can provide a parallel sided bipolar configuration, for clamping a 2 mm portion or thickness of tissue. In some instances, embodiments encompass probe assemblies having an electrode distance spacing profile that varies along the length of the probe assembly. Hence, the width at a distal portion of the probe assembly internal recess may be greater than or less than an adjacent proximal portion. Probe assemblies that provide a variable distance D along the length of the probe assembly can, for example, accommodate and draw in thicker tissue at the distal end and thinner tissue at the proximal end, or vice versa. Such probe assemblies can be used to treat certain tissue structures such as Waterston's groove area, the left superior pulmonary vein (LSPV) or ligament of Marshall area, or other tissue structures presenting variable thickness profiles, and the like. In some instances, probe assembly 1510 can be configured for delivery though a 12 mm port, for example. Although the electrode assemblies 1550, 1560 shown here are parallel or substantially parallel to one another, embodiments of the present invention encompass configurations where electrode assemblies 1550, 1560 are offset from one another at an angle A1 or A2, such as shown in the cross-section view of FIG. 15A. In some cases, angles A1 and A2 are within a range from about 5 degrees to about 30 degrees. In some instances, each of angles A1 and A2 are about 20 degrees. In some instances, angles A1 and A2 are the same. In some instances, angles A1 and A2 are different. In some instances, electrode mechanisms 1550 and 1560 are angled so as to provide a distance D between the electrodes at a lower ventral portion of about 5 mm and a distance D between the electrodes at an upper dorsal portion of about 4 mm. In some cases, electrodes 1550, 1560 can be offset from one another by an angle of between about 2 degrees and about 30 degrees. In some cases, the offset may be about 12 degrees. Some embodiments provide electrode mechanisms that change the angle or that provide variable angle profiles along a length of the probe assembly. FIGS. 6A, B, and C for example, show other electrode angle embodiments. Electrodes may present flat tissue-contacting surfaces in some cases, or curved or contoured tissue-contacting surfaces in other embodiments. As depicted in FIG. 15, the probe assembly can be configured or employed so that when applied to a patient tissue, a gap or open trough 1570 is formed between the opposing tissue portions 1580, 1590. Hence, the geometry of and/or the positioning of the probe assembly 1510 can be used to create a valley 1570 on the endocardial side of a cardiac tissue so that the blood can flow or circulate through the valley 1570 during a lesion creation procedure, particularly when the tissue is relatively thin. In this way, it is possible to inhibit or prevent clot formation during the surgical procedure. Where the patient tissue has a medium thickness, the endocardial surfaces of tissue portions 1580, 1590 may appose each other, and by virtue of the blood being squeezed out due to the apposition, it is possible to inhibit or prevent clot formation. With thicker tissue, the endocardial surface may only form a shallow groove, as depicted in FIG. 15B, again allowing the blood to wash the area of the lesion, thus inhibiting or preventing clot formation. The cardiac tissue in FIG. 15B may have a thickness of, for example, about 3 mm. As shown here, the endocardial surface may appose itself, for example within the recess of the stabilizer mechanism, and current can flow across the apposed tissue.

Figure 16:
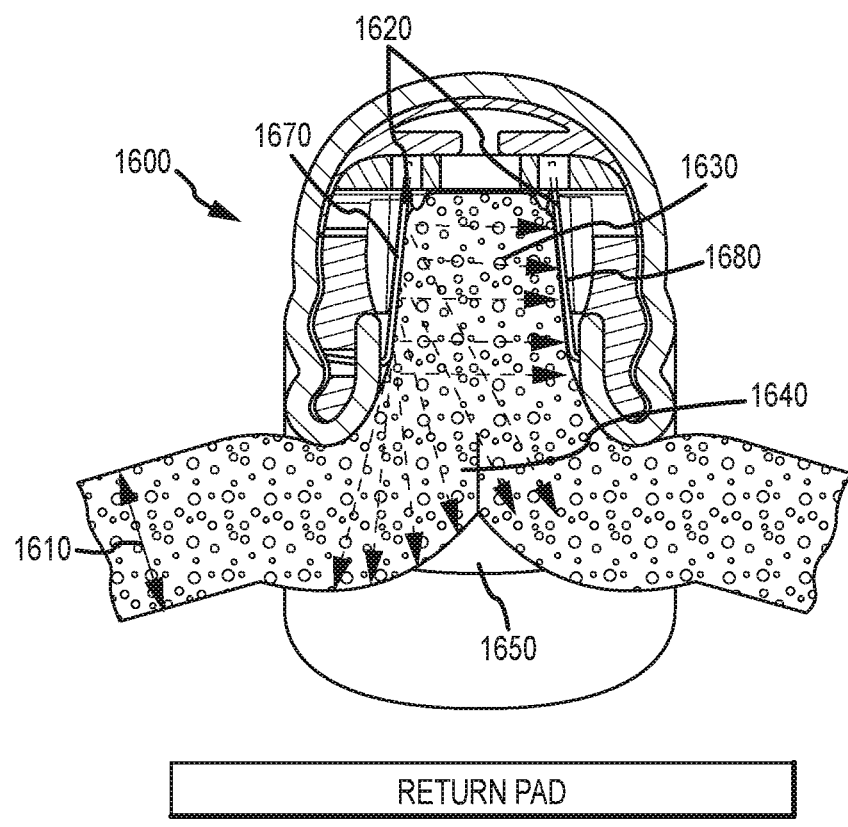
FIG. 16 shows aspects of surgical systems and methods according to embodiments of the present invention.

As seen in the cross-section view of FIG. 16, a probe assembly 1600 can be flexed toward the suction recess side 1630 such that the probe forms a curved shape. A neutral plane is follows the curve of the probe and lies upon the area of the probe which is neither stretching nor shortening in length. During use, it may be desirable that certain components, such as wires which are connected to the electrodes, not be unduly stretched during flexion. Appropriate positioning of the path of these wires along the length of the probe can help to avoid such stretching. As shown here, the path of the wires 1620 may lie very close to the neutral bending plane, and therefore the wires experience little stress or tension during operation. Additionally, from a top view of the probe, the wires may be installed in a serpentine pattern that accommodates the small length change due to the offset from the neutral bending plane. Likewise, the wire path through the U-joints may cross near the pivot points for the same purpose. Typically, a probe assembly includes a vacuum space or lumen which houses wires for delivering electricity to or returning electricity from the electrodes. Typically, the surgical system is configured so that there is sufficient slack in the wires, such that the wires do not become taut or strained during operation of the system, which may include flexing and twisting of the probe assembly or other components.

As further depicted in FIG. 16, current can be dispersed from epicardium to endocardium in a bipolar mode (arrows 1630) as well as in a monopolar mode (arrows 1640). In some cases, for example when treating a tissue of greater thickness, the monopolar mode (arrows 1640) may disperse an amount of current that is greater than an amount of current which is dispersed with the bipolar mode (arrows 1630). As shown here, the apposed tissue forms a valley or shallow trough 1650, which can be washed away by flowing or circulating blood, so as to inhibit or prevent clot formation. During operation in the monopolar mode, a ground pad is typically used. For example, a ground pad may be placed against the patient's back. As shown here, when in the bipolar mode, current is directed from one electrode (e.g. 1670) to an opposing electrode (e.g. 1680). Hence, the current path 1630 locally constrained. In contrast, when in the monopolar mode, current path 1640 is more diffuse or radiating, as the return pad is at a greater distance from the active electrode mechanism and there is less local constraint on the current spread.

Figure 17:
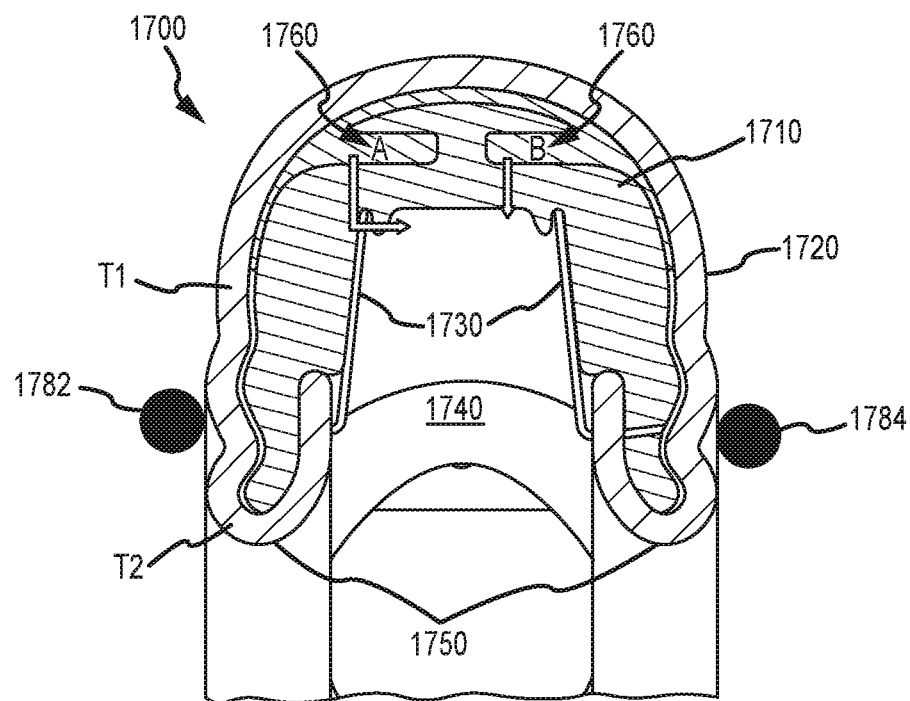
FIG. 17 shows aspects of surgical systems and methods according to embodiments of the present invention.
Figure 19:
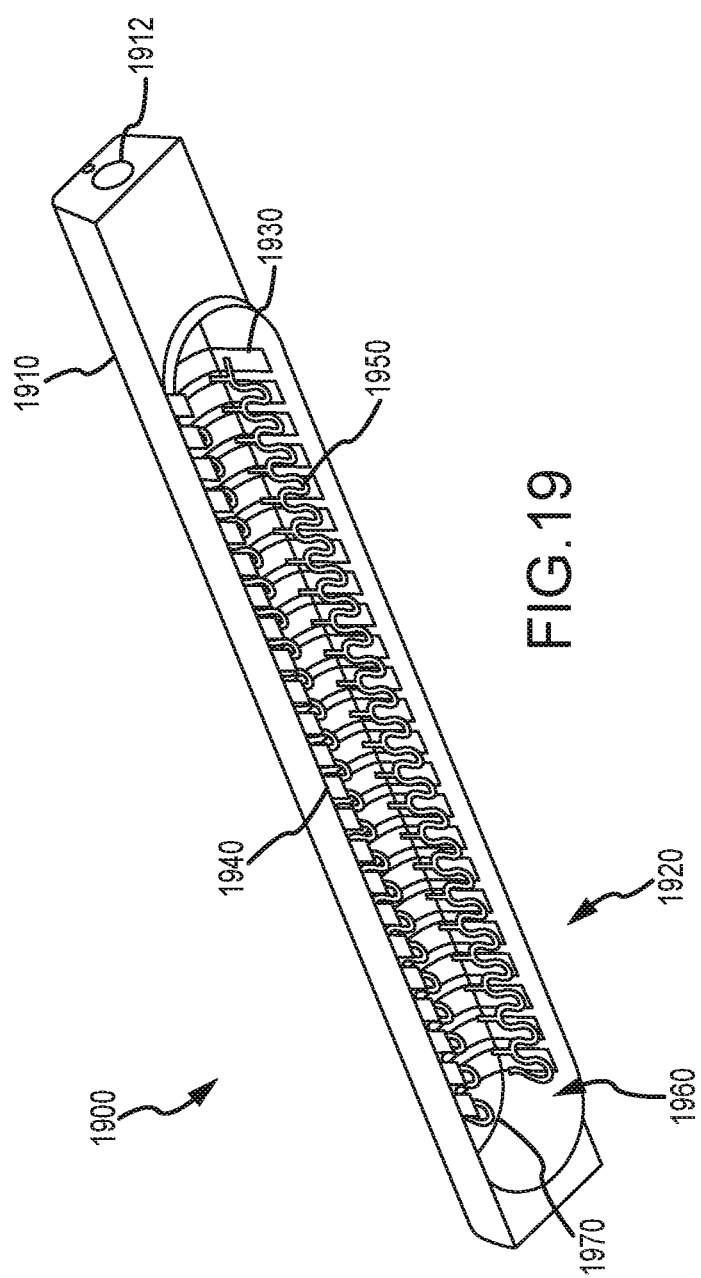
FIG. 19 shows aspects of surgical systems and methods according to embodiments of the present invention.

FIG. 17 shows a cross-section view of a probe assembly 1700 that includes a stabilizer mechanism 1720, and an ablation mechanism having a ribcage mechanism 1710 coupled with a first and second electrode assemblies 1730. As discussed elsewhere herein, and as depicted here, ribcage assembly 1710 can operate to support the suction pod 1720 externally against suction forces, and the electrodes 1730 internally. Hence, ribcage mechanism 1710 can support the suction pod 1720 so as to prevent collapsing from suction forces which are generated within the probe recess 1740. Further, ribcage mechanism 1710 can support electrodes 1730 internally in a desired position to enhance contact between the electrodes 1730 and the patient tissue which is drawn into the recess 1740. In some instances, pod or stabilizer mechanism 1720 is constructed of or includes a thin flexible skin. In this way, the ribcage mechanism 1710 may operate to provide an inner skeleton which gives shape to the stabilizer mechanism 1720 and also absorb and flex in response to external forces which may impinge upon the probe assembly, while also remaining sufficiently flexible to allow the stabilizer mechanism to remain in a sealed vacuum contact (e.g. via flexible skirt sections 1750) with the tissue, and to provide and enhance contact between the electrodes 1740 and patient tissue which is drawn into recess 1740. The ribcage mechanism 1710 can be configured so that the pocket or channel 1740 is maintained during use, and suction can therefore travel the full length of the probe assembly. As shown here, suction or relative negative pressure can be administered through an upper or rear channel or lumen 1760, within the probe assembly, and thereafter pass through ribcage mechanism 1710 and electrode 1730 as indicated by arrow A, or pass through ribcage mechanism 1710 as indicated by arrow B. In some cases, pod mechanism 1720 includes pod walls having a first thickness T1, and a skirt section having a second thickness T2. In some cases, the skirt thickness is less than the wall thickness. The skirt section 1750 at the margins of the pod mechanism 1720 can operate to help form and maintain a seal between the probe assembly and the patient tissue, thus allowing the delivered suction to draw the tissue into the recess 1740. The skirt section 1750 may provide a thin tapering section that is sufficiently flexible to conform to any small irregularities of the tissue surface on a smaller scale. Additional aspects of exemplary skirt features are shown in FIG. 19. In some instances, surgical systems may include means or clamping mechanisms for squeezing and/or expanding the recess provided by the probe assembly. For example, systems may include a set of rails or tongs 1782, 1784 that can be moved toward each other to reduce the recess or to compress tissue within the recess, and/or that can be moved away from each other to expand the recess. Such squeezing means or expanding means may include spring-loaded arms or tongs, clamps, rails, and the like. In some cases, the tongs or clamps can be individually controlled.

Figure 18:
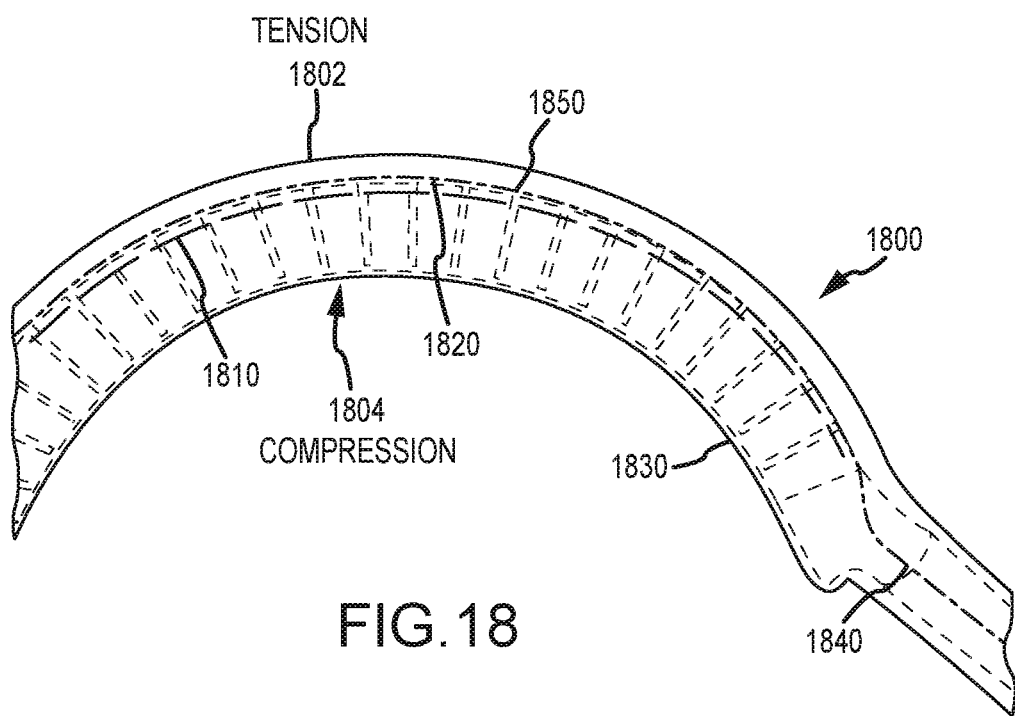
FIGS. 18 and 18A show aspects of surgical systems and methods according to embodiments of the present invention.
Figure 18A:
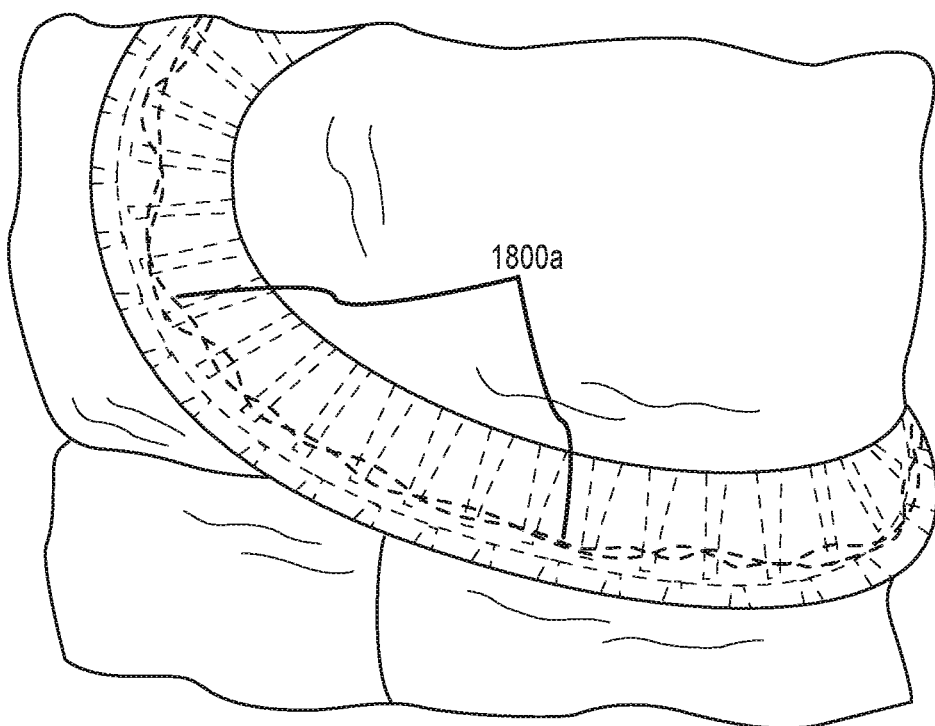

In exemplary embodiments, a probe assembly 1800 can be configured to be flexible in an upward direction, a downward direction (as shown here, flexing toward the suction or ventral side), a sideways left direction, a sideways right direction, and in torsion. For any given deflection in the probe assembly 1800, there can be a related neutral plane 1810, which is bent or curved in correspondence with the deflection. Accordingly, a first portion 1802 of the probe assembly may be in tension and a second opposing portion 1804 of the probe assembly may be in compression. The neutral plane 1810 can also be described as the plane where probe assembly material to the outside of that curved plane is in tension and being stretched, and probe assembly material inside that curved plane is in compression or being shortened in length. The position of this neutral plane is determined by the sum of the forces within the probe assembly during deflection. When subjected to bending forces as depicted here, the compressive and tensile forces develop, with higher compressive stresses forming at the ventral portion 1804 of the probe assembly and higher tensile stresses forming at the dorsal portion 1802 of the probe assembly. At the neutral plane there is no bending stress. In some embodiments it is desirable to prevent or inhibit stretching of certain probe assembly components during flexion of the probe assembly. For example, it may be an objective to not stretch wires with relatively delicate connections to electrodes, and thus such wires can be positioned along a path 1820 that coincides with the neutral plane or axis 1810. As depicted here, the path of the wires 1820 lies very close to the neutral plane 1810 and therefore experiences little stress when the probe assembly flexes. Relatedly, a more proximal section of the path of wires 1840 may pass through the U-joints near their pivot points to minimize electrical wire stretch. Hence, with the wiring path at or near the neutral plane (e.g. slightly dorsal thereto), and at or near pivot points of the U-joint or coupling mechanism, wires may experience little or no tension when the probe assembly bends (e.g. in a downward direction) or is otherwise maneuvered during operation. Additionally, from a top view of the probe (see e.g. FIG. 18A), the wires may be installed in a serpentine pattern that accommodates the small length change due to the offset from the neutral bending plane. As shown in FIG. 18A, wiring 1800a for delivering energy to electrodes of a probe assembly can be positioned in a zigzag or serpentine pattern. The wiring path may be at or near a neutral plane of the probe assembly. Such wiring configurations can allow a certain amount of slack to be present in the wiring, and to remain when the probe assembly is bent (e.g. downward toward the suction side 1830 as shown in FIG. 18). The wires can be for providing electrical connectivity with active and return electrodes, thermocouples, pacing electrodes, and the like. In some instances, a probe assembly may include an internal tension member or wire that it positioned at or near the neutral plane 1810. Such an internal tension member 1850 can be used to transmit pulling forces to the end of the probe assembly without affecting the probe assembly itself. In some cases, a ribcage mechanism may or may not have the ability to resist or transmit tension forces. Such an internal tension member can be used as a means to resist or transmit tension through a ribcage mechanism, or to increase the ability of a ribcage mechanism to resist or transmit tension therethrough. In some instances, an internal tension member may lie along and contribute to the position of the neutral plane.

FIG. 19 shows a perspective view a probe assembly 1900 according to embodiments of the present invention. As depicted here, probe assembly 1900 includes a stabilizer mechanism 1910 having a port 1912 which can receive suction from a vacuum source via a tubing assembly (not shown). Probe assembly 1900 also includes an ablation mechanism 1920 having a ribcage mechanism 1930 coupled with a first electrode assembly 1940 (e.g. active) and a second electrode assembly 1950 (e.g. return). The stabilizer mechanism 1910 can provide an outer stabilizing membrane or mechanism. In some cases, ribcage mechanism 1930 includes a series of ribs which support both the stabilizer mechanism 1910 and the electrodes 1950, 1960. As shown here, electrodes can be provided in a serpentine configuration. The probe assembly 1900 may also include a skirt or continuous raised lip or sealing edge 1960, optionally as part of the stabilizer mechanism 1910, which accommodates irregular surface features of the tissue and helps to ensure sealed contact between the probe assembly 1900 and the tissue. A skirt section 1960 at the margins of the pod mechanism 1910 can operate to help form and maintain a seal between the probe assembly and the patient tissue, thus allowing the delivered suction to draw the tissue into a recess 1970. The skirt section 1960 may provide a thin tapering section that is sufficiently flexible to conform to any small irregularities of the tissue surface on a smaller scale.

Figure 20:
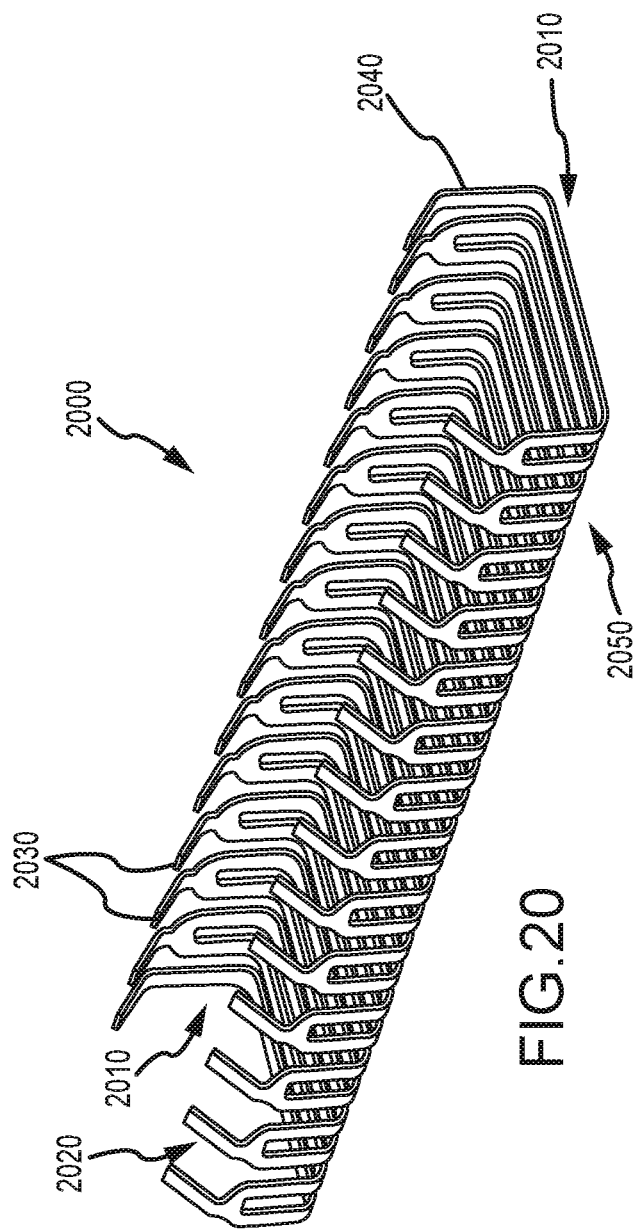
FIG. 20 shows aspects of surgical systems and methods according to embodiments of the present invention.

FIG. 20 depicts an exemplary electrode mechanism 2000 for use in a probe assembly according to embodiments of the present invention. As shown here, this electrode mechanism can be used as a monopolar electrode for delivering a monopolar ablation to a patient tissue. The electrode mechanism can be housed at least partially within a suction pod assembly, and may define a recess 2010 into which tissue may be drawn through the application of suction as described elsewhere herein. Hence, some probe assembly embodiments may include a monopolar probe electrode 2000 that can be used to provide suction, through intercostal spacings or gaps 2020 between individual tines or ribs 2030 of the electrode, to the tissue. In this way, suction can be transmitted through the spaces between the electrode tines or ribs, as the probe assembly draws tissue into contact with the electrode, and/or between a first electrode side 2040 and a second electrode side 2050 of the ablation or electrode mechanism. In some instances, it may be desirable to control the amount of tissue being drawn into an electrode recess, a ribcage recess, and/or a suction pod recess. In some cases, it is possible to control the amount of tissue being drawn into an electrode recess, a ribcage recess, and/or a suction pod recess by providing a spacing of electrode tabs on ribs as well as suction pod webs filling in the gaps between ribs. In some instances, electrode mechanisms can provide intercostal spacing or gaps 2020 having a width within a range from about 0.2 mm to about 0.5 mm. The spacing between electrode tabs or plates can be configured so that excessive tissue does not bulge or extend into the spacings during use, which may act to interfere with suction as it is applied to the tissue. In some cases, such spacing keeps tissue out but allows suction and movement (which changes the spacing dynamically).

Figure 21:
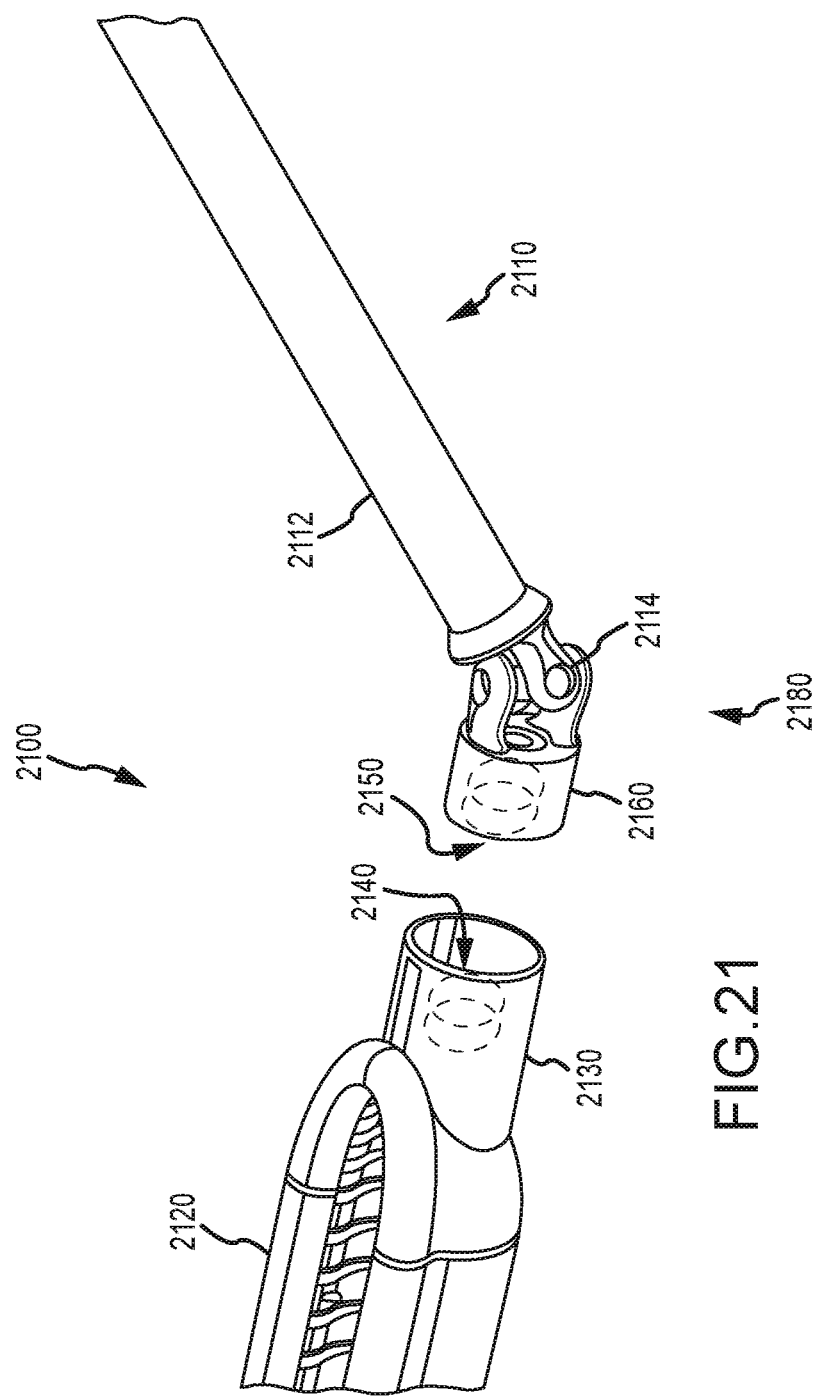
FIG. 21 shows aspects of surgical systems and methods according to embodiments of the present invention.

FIG. 21 illustrates aspects of a treatment system 2100 that includes an introducer assembly 2110 and a probe assembly 2120 according to embodiments of the present invention. As shown here, probe assembly 2120 includes a distal section 2130 which houses a magnet 2140. In a corresponding manner, introducer assembly 2110 includes a distal section 2180 having a magnetic terminal 2160. Distal sections 2130, 2180 may be configured to interface in a male/female connection. For example, as shown here, distal section 2130 provides a female interface that is adapted to receive a male interface provided by distal section 2180. In some instances, introducer assembly 2110 includes an elongate flexible shaft 2112, or is otherwise flexible. Introducer assembly 2110 may also include a rotational or pivoting coupling assembly 2114 that couples distal section 2180 with shaft 2112. As shown here, coupling assembly 2114 may include a U-joint mechanism. In some instances, a coupling assembly 2114 may include a single U-joint mechanism, a double U-joint mechanism, a triple U-joint mechanism, or a multi-U-joint mechanism. Such coupling assemblies can allow a desired amount of angulation of the magnetic terminal 2160. In some instances, magnetic terminal 2160 may include a magnet 2150, for example which may reside within the terminal 2160. In some instances, magnets 2140 and 2150 may have opposing polarities. Magnetic terminal 2160 may be configured to connectively mate with distal terminal 2130 of probe assembly 2120.

FIG. 22 depicts aspects of a treatment system 2200 that includes an introducer assembly 2210 and a probe assembly 2220 according to embodiments of the present invention. As shown here, probe assembly 2220 includes a ribcage mechanism 2224, and a distal section 2230 which houses a magnet 2240. In a corresponding manner, introducer assembly 2210 includes a distal section 2280 having a magnetic terminal 2260. Distal sections 2230, 2280 may be configured to interface in a male/female connection. For example, as shown here, distal section 2230 provides a female interface that is adapted to receive a male interface provided by distal section 2280. In some instances, introducer assembly 2210 includes an elongate flexible shaft, or is otherwise flexible. Introducer assembly 2210 may also include a rotational or pivoting coupling assembly that couples distal section 2280 with a shaft. In some instances, magnetic terminal 2260 may include a magnet 2250, for example which may reside within the terminal 2260. In some instances, magnets 2240 and 2250 may have opposing polarities. Magnetic terminal 2260 may be configured to connectively mate with distal terminal 2230 of probe assembly 2220. As illustrated in the longitudinal cross-section view shown here, probe assembly magnet 2240 may be a solid magnet within a female housing element, and introducer assembly magnet 2250 may be a hollow magnet within a male housing element.

Figure 23:
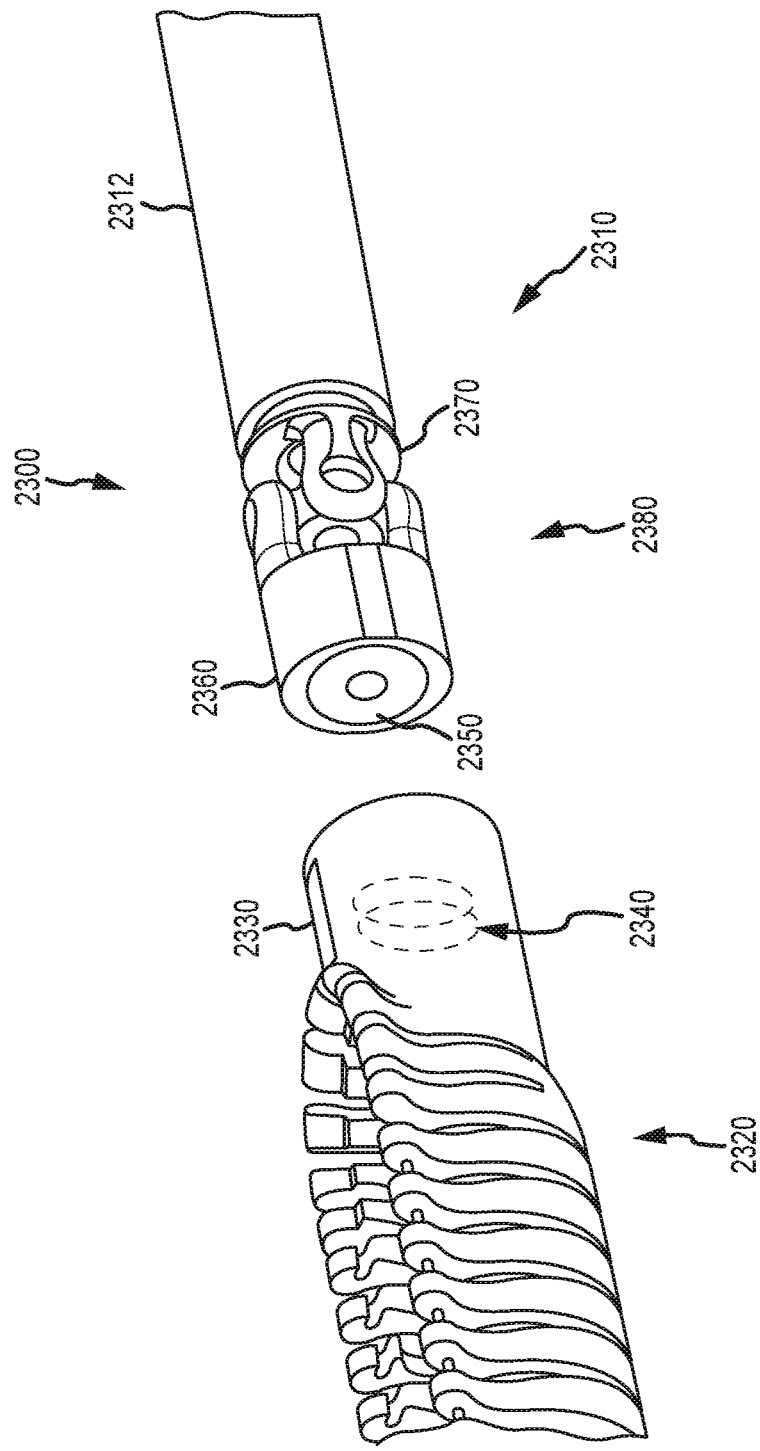
FIG. 23 shows aspects of surgical systems and methods according to embodiments of the present invention.

FIG. 23 depicts a surgical system 2300 according to embodiments of the present invention. As shown here, surgical system 2300 includes an introducer assembly 2310 and a probe assembly 2320. As shown here, probe assembly 2320 includes one or more electrodes (not shown) and a ribcage mechanism that reside within a flexible suction pod mechanism (not shown). Probe assembly 2320 may also include a distal section 2330 which houses a magnet 2340. In a corresponding manner, introducer assembly 2310 includes a distal section 2380 having a magnetic terminal 2360. Distal sections 2330, 2280 may be configured to interface in a male/female connection. For example, as shown here, distal section 2330 provides a female interface that is adapted to receive a male interface provided by distal section 2380. In some instances, introducer assembly 2310 includes an elongate flexible shaft, or is otherwise flexible. Introducer assembly 2310 may also include a rotational or pivoting coupling assembly that couples distal section 2380 with a shaft. In some instances, magnetic terminal 2360 may include a magnet 2350, for example which may reside within the terminal 2360. In some instances, magnets 2340 and 2350 may have opposing polarities. Magnetic terminal 2360 may be configured to connectively mate with distal terminal 2330 of probe assembly 2320. In some instances, distal section 2380 presents a male mating feature having an ovalized or non-circular cross-section, and likewise, distal section 2330 presents a female mating feature having a corresponding ovalized or non-circular cross-section. For example, distal sections 2330, 2380 may present corresponding oval shapes, which allow an indexed coupling of the probe assembly 2320 with the introducer assembly 2310 such that when the probe assembly 2320 and the introducer assembly 2310 are magnetically engaged, the operator is able to apply torque, tension, and/or compression from the introducer assembly 2310 to the probe assembly 2330 (e.g. via a U-joint of the introducer assembly). Hence, for example when a U-joint 2370 is bent off axis, the operator is additionally able to apply a bending force to the probe assembly in order to generate a curve.

Figure 24:
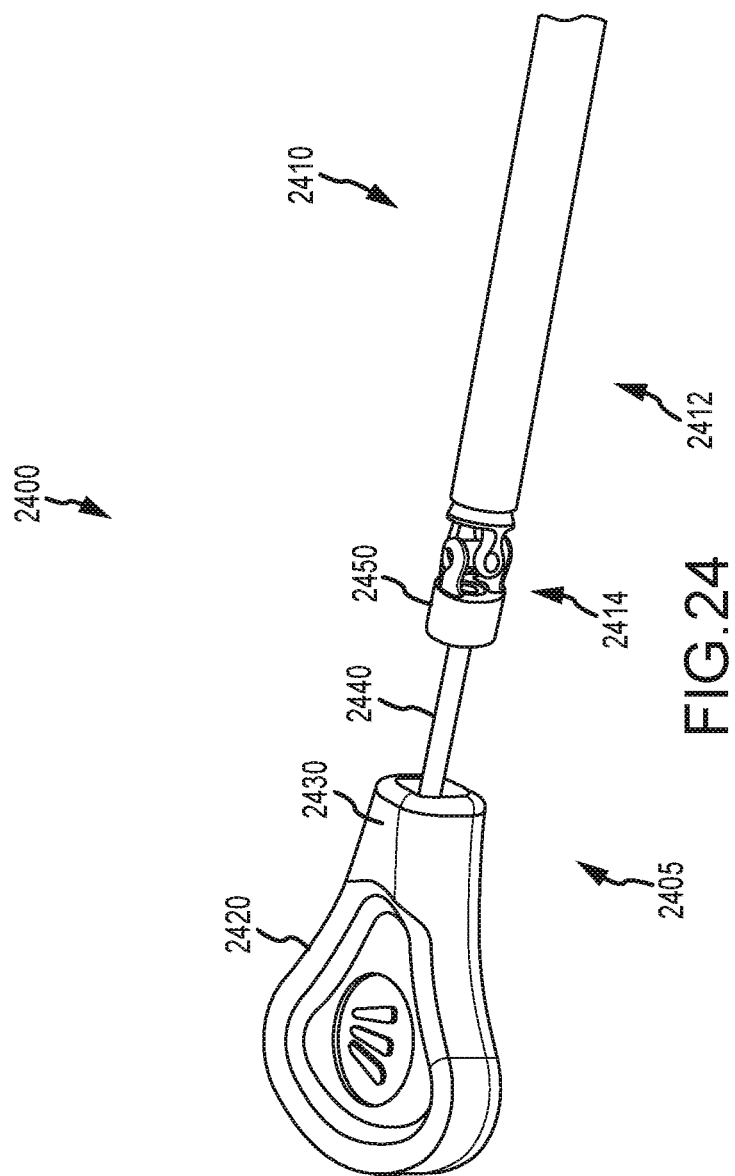
FIG. 24 shows aspects of surgical systems and methods according to embodiments of the present invention.

FIG. 24 depicts aspects of a surgical system 2400 according to embodiments of the present invention. As shown here, system 2400 includes an introducer assembly 2410 having a flexible tubing or shaft mechanism 2412. The flexible tubing or shaft mechanism 2412 may also correspond to the flexible tubing or shaft mechanism 2312 shown in FIG. 23, or the flexible tubing or shaft mechanism 2212 shown in FIG. 22, or the flexible tubing or shaft mechanism 2212 shown in FIG. 21, for example. In FIGS. 12-23, a distal section of the flexible tubing or shaft mechanism is shown, whereas in FIG. 24, a proximal section of the flexible tubing or shaft mechanism is shown. As depicted in FIG. 24, surgical system 2400 may also include a stylet mechanism 2405. As depicted here, stylet mechanism 2405 may include a handle 2420, a magnetic housing portion 2430, and a malleable wire shaft 2440. Introducer assembly 2410 may include a magnetic U-joint mechanism 2414 similar to a U-joint located at a proximal section of the assembly 2410. In some instances, introducer assembly 2410 may include a magnetic terminal 2450 at the proximal section of the assembly 2410. In some instances, the introducer assembly may include a hollow magnet in a soft housing, with or without a U-joint mechanism at the proximal section. In some cases, for example where the introducer does not include a U-joint at the proximal section, a soft housing may have one or more radial holes in the side of the housing behind the magnet that lead into the lumen of the hollow introducer tubing. The stylet mechanism 2405 may be used, for example, when magnetically disconnecting the introducer assembly 2410 from the distal end of a probe assembly, which may be out of easy reach in the anatomy. In some instances, stylet mechanism 2405 can be slidably coupled with introducer assembly 2410. For example, a malleable wire shaft or element 2440 of stylet mechanism 2405 may be introduced into a proximal section of flexible tubing 2412.

Any of the coupling mechanisms or configurations for coupling a probe assembly with an introducer assembly as disclosed herein may also be used for coupling a stylet mechanism with an introducer assembly. In some instances, the stylet shaft 2440 can be inserted either through U-joint mechanism 2414, a hollow magnetic U-joint, a hollow magnet in a soft housing, or into one of the holes in the side of the soft housing, and down the length of the introducer lumen or flexible tubing 2412 to the distal end thereof end. In some instances, the stylet mechanism may pass into a hollow magnet at the distal end of the introducer assembly, and when the stylet handle 2420 is pushed into full engagement with the proximal section of the introducer assembly 2410, a distal section of the elongate shaft 2440 can contact the distal section of the probe assembly (e.g. the probe assembly magnet), and thus operate to separate a probe assembly distal section magnet and an introducer assembly distal section magnet away from each other. In this way, once the introducer assembly has been used to place the probe assembly where desired, it is possible to disengage the probe assembly from the introducer assembly, and hence the introducer assembly can be withdrawn from the treatment site, while allowing the probe assembly to remain at the treatment site.

In some instances, the stylet mechanism 2405 may operate to stiffen the introducer assembly, for example, when the elongate shaft 2440 is placed within the tubing assembly 2412. Such a stiffening technique can be employed when inserting the introducer assembly into the patient anatomic pathway or when maneuvering the introducer assembly within the patient anatomy. In some instances, the introducer assembly can be placed within the patient body, with the distal section of the introducer extending to an easily accessible location (e.g. outside of the body). The distal section of the introducer assembly can then be coupled with a distal section of the probe assembly, and the introducer assembly can then be retracted, thus drawing the probe assembly into the patient anatomy, as the probe assembly follows the path of introducer assembly. In other words, once the introducer assembly is in place, it can be magnetically coupled to the probe assembly outside the body, and the introducer assembly can be used to lead the probe assembly by the magnetic connection into a position in the anatomy, pulling the probe assembly around anatomical curves or structures, as needed through tension applied to the introducer assembly. In some instances, an introducer assembly may not reach completely around the target anatomy at first placement, so a second similar flexible introducer assembly with or without a stylet mechanism inserted therein may be introduced in the opposite direction along the anatomic pathway until the magnetic ends of both introducers meet making a long complete loop in, around and out of the patient to so that tension may be applied to one end and compression applied to the other to advance the probe into position. This second introducer assembly may be removed from its magnetic connection to the first introducer assembly by hand outside the body and the stylet mechanism may be used as elsewhere described herein when desired to remove the introducer assembly from the probe assembly.

Relatedly, a positioner instrument assembly having a magnetically attractive element or ball on a malleable or stiff shaft with a handle may be used to retrieve the end of the probe introducer assembly when the introducer assembly is deep in the anatomy and/or used on the magnetic distal end of the probe assembly itself as a positioner instrument to manipulate the probe assembly at a close distance. Such a positioner instrument may have an axial push button on the handle that translates a long, thin rod that runs the length of the positioner instrument in order to extend the rod out of a hole in the magnetically attractive element or ball end to eject or disconnect the magnet from the attached device. Where such a positioner instrument has a malleable shaft, the rod may also be flexible, for example, made of material such as a plastic. Similarly, a positioner instrument having a handle with push button, a stiff shaft, and a magnetic U-joint with hollow magnet for a flexible rod to pass therethrough may be used for similar purposes.

Hence, embodiments of the present invention encompass a variety of coupling means, such as magnetic coupling mechanisms, which can be used to transmit torque between an introducer assembly and a probe assembly.

Figure 25:
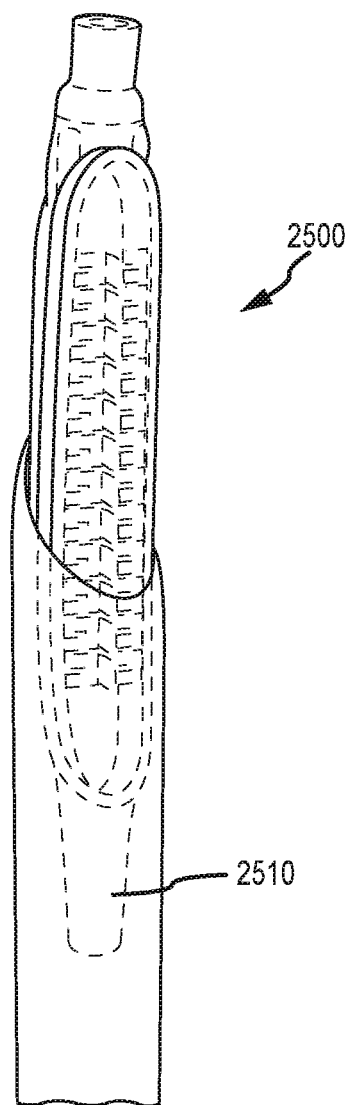
FIG. 25 shows aspects of surgical systems and methods according to embodiments of the present invention.

FIG. 25 depicts an exemplary probe assembly 2500 extending from a port device or sheath 2510. The port device 2510 shown here has a 12 mm diameter, although other size configurations may be used.

In some instances, a suction pod of the probe assembly may include graphics or markings thereon, for example, in the form of single lengthwise stripes along both sides that indicate where active and return electrodes are located. On some embodiments (e.g. long probe assembly), graphics or markings bearing the color green, which shows up well in a surgical environment, may be used indicate the return electrode side. Embodiments also encompass suction mod mechanisms having graphics or markings on the side of the pod assembly which is intended to be placed upward during a typical cardiac surgery. The color black, which also shows well in surgery, may be used for graphics or markings on the opposite side. In some cases, graphics or markings may include stripes that are interrupted by short breaks to indicate the break between electrodes. The stripes themselves can indicate the placement of the electrodes and their start and finish lengthwise. Down the centerline of the probe assembly on the back side there may be numbers indicating the electrode number inside of the probe assembly, which can be used to aid in determining which electrode is over what anatomic structure and therefore which electrode is to be turned on or off. Other numbering, lettering, and marking schemes may be employed for surgeon feedback. Similarly, an introducer assembly may have lengthwise markings that correspond to those on a probe assembly such that moving the introducer assembly one marking segment causes corresponding movement of probe assembly which may be out of sight.

Additional Aspects of Ablation Devices and Methods

In some instances, an end plug or cap is attached with the distal end of the jawbone at the tip of the jaw. Exemplary jawbone mechanisms and related systems are described for example in U.S. Patent Publication No. 2011/0152860, the contents of which are incorporated herein by reference. The end plug can be at least partially placed within the inside of the boot. In operation, the jawbone and end plug rotate together relative to the boot which remains stationary. The end plug may present a hard point or surface where a surgeon or operator can place their finger when rotating the jaw to a new position.

During a surgical procedure, the surgeon may slide the clamp device within the patient and underneath the pulmonary veins or other anatomical feature. In some instances, the surgeon may wish to advance the jaws along a particular path. The surgeon may maneuver the clamp device alone, without assistance from a supplemental device or guide. In some instances, a surgeon may thread a piece of rubber, tubing, surgical tape, or other soft and flexible material along a particular insertion path, for example by using their fingers or another clamp. The threading element can be attached with the ablation clamp device, for example at a distal section of the end plug or boot, and the threading element can be used to help navigate the ablation clamp device throughout the patient anatomy.

In some instances, the threading element is fed along the desired navigation path, and then a proximal section of the threading element is attached with the ablation clamp, for example at a distal section of the lower jaw clamp. For example, a rubber tubing can be slipped over the distal tip of the lower jaw clamp. The operator or physician may then pull on or use a distal section of the threading element to help draw the ablation clamp as desired within the patient anatomy. Such techniques may be useful to avoid having a distal end of the jaw clamp inadvertently punch through or lacerate the patient tissue. Once the clamp jaw is positioned as desired, the threading element can be severed or removed from the jaw clamp.

In some instances, the end plug may have a holes or holes that accept a threading element such as a long suture. The surgeon may place the suture at the end of the jaw tip, and through the hole, so as to attach the long suture with the jaw tip or end plug. The surgeon may also take a piece of rubber tubing which commonly used in operating room, and placed an open end of the tubing next to the suture. The tubing can be elastic, flexible, and soft, and suitable for use within the patient tissue anatomy. In some cases, the tubing has a lubricious quality when wet. The surgeon may then take a wire, which may be folded in half, insert the wire through one end of the tubing and out the other, and use the wire (e.g. a looped end) extending from the other side to snag the suture. The wire can then be withdrawn back into the tubing, thus drawing the suture into the tubing. The tubing can then be snugged against the jaw tip or end plug, for example by pulling on the suture away from the clamp and pushing on the tubing toward the clamp. The snagging wire may be discarded. The tubing can help to insulate the suture from contacting or pressing against patient tissue such as an artery. While holding the distal end of the suture and the distal end of the rubber tubing, the surgeon may couple the suture with the rubber tubing, so that the interior suture provides a tension member within the rubber tubing. For example, the surgeon may apply a hemostat or clamp across the tubing, so as to pinch the tubing against the suture. This clamping can operate to lock the tension member or suture within the compression member or tubing, so that the tension member and the compression member become a unit. The surgeon can then pull on the distal end of the tubing, without having the tubing come off of the distal end of the clamp jaw. In a sense, the tension member and compression member become an extension of the jaw, and can be used as an introducer to pull the jaw into the patient anatomy, or otherwise position the jaw in a desired location within the patient. When the introducing procedure is complete, the surgeon may remove the hemostat clamp, slip the rubber off of the jaw. The tubing slips off easily because the suture tension member is no longer clamped to the rubber tubing. As soon as the clamp is removed, the suture and rubber tubing become separate members. After the ablation procedure is complete, the jaw member can be withdrawn from the patient, pulling along the untensioned suture. In this way, it is possible to attach or detach the red rubber without having to manually grasp the jaw tip and proximal portion of the tubing so as to bring them together. It provides an efficient technique for introducing a clamp, for example when the lower jaw is blind under the pulmonary veins. By providing an apertured end plug at the end of the jaw bone, it is possible to obtain an introducer mechanism that can pull on the jawbone without pulling directly on the boot, which may in some instances lead to undue stress on the boot, or unwanted bending of the ablation electrode, thus causing an electrical problem. In some instances, a surgeon may forego the use of a tensioning suture member, and instead simply place a proximal end of the rubber tubing over a distal end of the lower jaw member, for example, and use the tubing as an introducer. The surgeon may wish to take care that the proximal section of the tubing does not unduly cover the ablation element or electrode, particularly if the tubing is to be left in place during the ablation procedure. The distal section of the tubing can be manually placed under the vessels, and the surgeon can use their fingers to ensure the tubing is being advanced along the appropriate insertion path. During this insertion procedure, the tubing may be pulled at an angle so that it does not come off the jaw tip. Once the ablation clamp is suitably positioned, the rubber tubing may be slipped off the jaw tip, for example by pulling the tubing in a direction coaxial with the distal jaw tip. In some instances, a surgeon may wish to place a proximal section of the tubing over a distal tip of the jaw, and then stitch a suture through the side of the tubing and into the holes of the apertured end plug. In this way, the tubing can be fixedly attached with the end plug or jawbone.

In some instances, there may be no end plug at the distal end of the jaw tip. In some instances, the jawbone provides a rounded distal end without such an end plug. Optionally, a boot may cover the distal end of the jawbone. The boot may present a rounded distal end. Optionally, a boot may present a tapered or bullet shaped distal end. In use, the surgeon may slip a proximal portion of the introducer rubber tubing over a distal section of the boot. In some instances, the surgeon may wish to stitch a suture through the rubber tubing and the boot, or otherwise attach them with each other in another suitable manner. Hence, the tubing can be used to pull the jaw into place.

In some instances, the jaw may or may not include an end plug, and the boot may have a small hole or aperture at its distal end, for example as the default result of a manufacturing procedure. A small soft plug may be placed in the hole, and optionally glued therein, so that there is no surface discontinuity along the boot. The plug and the boot can be constructed of the same or similar materials. In some instances, the plug may include a light mechanism, optionally coupled with wires that run along a hollow core of the jawbone and into an interior of the clamp handle or shaft. When advancing the clamp mechanism within the patient's body, for example beneath the pulmonary veins, the surgeon may use the light to help determine the location of the distal end of the clamp jaw within the patient's anatomy. As an another example, it is known that the pericardium wraps around the heart and reflects or attaches onto the inner surface of the thoracic cavity in various places. When pushing through these reflections with the clamp device, the surgeon can rely on light from the end plug lamp to determine the progress of the clamp as it goes through the tissue. For example, the light becomes brighter as the distal jawtip is closer to breaking through the tissue or reflection. In some instances, the end plug lamp includes a distally located light emitting diode (LED). In some instances, the end plug light mechanism includes a fiber optic member that faces outward from the distal portion of the jaw. Hence, a light source or lamp can be located in the handle or elsewhere on the clamp device, and the fiber optic member can operate to transmit light from the light source to the end of the distal jaw tip and out of the distal boot aperture. In some instances, the ablation assembly may include a separable and reusable flashlight which can clip into or otherwise attach with the handle.

In some instances, the boot or end plug includes an elongate distal flexible member which can operate as an integrated introducer. The surgeon can use this long introducer lead to help position the clamp jaw within the patient's anatomy. Once the ablation clamp is positioned as desired, ablation may commence. The elongate distal section may be left in the surgical field during the ablation. Optionally, the surgeon may wish to cut or sever the elongate distal flexible extension, for example, by cutting the boot with scissors, prior to ablation.

In some instances, the end plug may include a port or aperture for delivering a flush or irrigation fluid to the surgical site or patient tissue. For example, during some procedures blood or fluid may collect in the pericardial basin where the heart sits. The surgeon can use the apertured end plug to flush out this area, for example by using water or other suitable fluids. In some cases, the end plug may include a nozzle tip. In some instances, ablation devices may include irrigation or water ports disposed at the surface of the electrodes. Optionally, exemplary ablation devices may include internal cooling mechanisms. For example, an ablation device may include an internal tube or passage positioned within a jawbone. Fluid may be expelled from a distal section of tube and into the interior core of jawbone. Device includes a boot, an end plug, and electrode. As shown here, the tube floats inside of the jawbone, and terminates just proximal to the end plug. The tube can be used to pump out saline or other fluid, which is then circulated within the jawbone. The jawbone, which may be constructed of metal, can assume or approach the temperature of the fluid. During an ablation, the temperature of the boot may increase and the jawbone may also increase in temperature due to the burning or heating of the tissue. The circulated fluid can operate to carry heat away from the boot.

In some cases, the electrode is attached with the boot via legs located at the apex of each curve along the serpentine member. The legs can penetrate directly into the boot at about a 90 degree angle from the electrode plane. That is, the legs can be bent at a 90 degree angle from the flat surface of the electrode. The tips of each leg may have a swelled diameter. In some instances, the leg tips include an anchor mechanism that helps hold the electrode securely against the boot. For example, the leg tips may include a "T" shape, which effectively prevents the electrode from popping out of or away from the boot, particularly when the boot is twisted or otherwise deformed. This "T" anchor or foot of the leg tip can be embedded within the boot, below the boot surface. Hence, a significant amount of force is required to pull the electrode out of the boot. In some instances, the boot includes an anti-torsional mechanism. For example, the boot may include an internal tubular or coiled structure that can flex from side to side and also provide torsional rigidity. In some devices, a polymer sleeve may be placed over the jawbone, between the jawbone and the boot, providing a lubricious intermediary between the jawbone and boot.

Individual system elements or aspects of a tissue treatment computer system may be implemented in a separated or more integrated manner. In some embodiments treatment systems, which may include computer systems, also include software elements, for example located within a working memory of a memory, including an operating system and other code, such as a program designed to implement method embodiments of the present invention. In some cases, software modules implementing the functionality of the methods as described herein, may be stored in a storage subsystem. It is appreciated that systems can be configured to carry out various method aspects described herein. Each of the devices or modules of the present invention can include software modules on a computer readable medium that is processed by a processor, hardware modules, or any combination thereof. Any of a variety of commonly used platforms, such as Windows, MacIntosh, and UNIX, along with any of a variety of commonly used programming languages, such as C or C++, may be used to implement embodiments of the present invention. In some cases, tissue treatment systems include FDA validated operating systems or software/hardware modules suitable for use in medical devices. Tissue treatment systems can also include multiple operating systems. For example, a tissue treatment system can include a FDA validated operating system for safety critical operations performed by the treatment system, such as data input, power control, diagnostic procedures, recording, decision making, and the like. A tissue treatment system can also include a non-validated operating system for less critical operations. In some embodiments, a computer system can be in integrated into a tissue treatment system, and in some embodiments, a computer system can be separate from, but in connectivity with, a tissue treatment system. It will be apparent to those skilled in the art that substantial variations may be used in accordance with any specific requirements. For example, customized hardware might also be used and/or particular elements might be implemented in hardware, software (including portable software, such as applets), or both. Further, connection to other computing devices such as network input/output devices may be employed. Relatedly, any of the hardware and software components discussed herein can be integrated with or configured to interface with other medical treatment or information systems used at other locations.

According to some embodiments, the treatment systems and methods described herein may be used in conjunction or combined with aspects of introducer systems and methods such as those described in U.S. Patent Application No. 60/337,070 filed Dec. 4, 2001; Ser. No. 10/272,446 filed Oct. 15, 2002; Ser. No. 10/310,675 filed Dec. 4, 2002; Ser. No. 10/410,618 filed Apr. 8, 2003; Ser. No. 11/148,611 filed Jun. 8, 2005; 60/939,201 filed May 21, 2007; 61/015,472 filed Dec. 20, 2007; 61/051,975, filed May 9, 2008; Ser. No. 12/124,743 filed May 21, 2008; Ser. No. 12/124,766 filed May 21, 2008; Ser. No. 12/255,076 filed Oct. 21, 2008; Ser. No. 12/273,938 filed Nov. 19, 2008; Ser. No. 12/339,331 filed Dec. 19, 2008; Ser. No. 12/463,760 filed May 11, 2009; 61/179,564 filed May 19, 2009; 61/231,613 filed Aug. 5, 2009; and 61/241,297 filed Sep. 10, 2009. The entire content of each of these filings is incorporated herein by reference for all purposes.

Relatedly, in some instances, the treatment systems and methods described herein may include elements or aspects of the medical systems and methods discussed in U.S. Patent Application No. 60/337,070 filed Dec. 4, 2001; Ser. No. 10/080,374 filed Feb. 19, 2002; Ser. No. 10/255,025 filed Sep. 24, 2002; Ser. No. 10/272,446 filed Oct. 15, 2002; Ser. No. 10/310,675 filed Dec. 4, 2002; Ser. No. 10/410,618 filed Apr. 8, 2003; Ser. No. 11/067,535 filed Feb. 25, 2005; Ser. No. 11/148,611 filed Jun. 8, 2005; 60/939,201 filed May 21, 2007; 61/015,472 filed Dec. 20, 2007; 61/051,975, filed May 9, 2008; Ser. No. 12/124,743 filed May 21, 2008; Ser. No. 12/124,766 filed May 21, 2008; Ser. No. 12/255,076 filed Oct. 21, 2008; Ser. No. 12/273,938 filed Nov. 19, 2008; Ser. No. 12/339,331 filed Dec. 19, 2008; Ser. No. 12/463,760 filed May 11, 2009; 61/179,564 filed May 19, 2009; 61/231,613 filed Aug. 5, 2009; and 61/241,297 filed Sep. 10, 2009. The entire content of each of these filings is incorporated herein by reference for all purposes.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

While exemplary embodiments have been described in some detail, by way of example and for clarity of understanding, those of skill in the art will recognize that a variety of modification, adaptations, and changes may be employed. Hence, the scope of the present invention should be limited solely by the claims.

The invention claimed is:

1. A surgical system for administering a lesion forming treatment to a patient tissue, comprising:
   a housing having an outer membrane, an inner ribcage, one or more ablation elements, and an inner recess, wherein the outer membrane encases the inner ribcage, wherein the one or more ablation elements are disposed on the inner ribcage, wherein the inner ribcage comprises a first wall and a second wall extending parallel to the first wall;
   a vacuum supply configured to deliver suction through the inner recess to draw a portion of the patient tissue into the inner recess, wherein inner ribcage permits movement of the first wall and the second wall upon application of a vacuum from the vacuum supply; and
   wherein the one or more ablation elements are adjustable in response to movement of the first wall and the second wall to accommodate a variety of tissue thicknesses.

2. The surgical system according to claim 1, wherein the inner ribcage comprises a hinge and a plurality of individual ribs, wherein the plurality of individual ribs bend in response to the variety of tissue thicknesses.

3. The surgical system according to claim 1, further comprising a temperature sensor disposed along the inner recess.

4. The surgical system according to claim 1, wherein the housing comprises a cooling lumen.

5. The surgical system according to claim 1, wherein the housing comprises an irrigation lumen.

6. The surgical system according to claim 1, wherein the housing comprises a web assembly, wherein when tissue is drawn into the inner recess, the web assembly is drawn into the inner recess to flex the housing.

7. The surgical system according to claim 1, further comprising a power source assembly configured to deliver energy to the ablation element.

8. A surgical system for administering a lesion forming treatment to a patient tissue, comprising:
   a housing having an outer membrane, an inner ribcage, one or more ablation elements, an inner recess, and a web assembly, wherein the outer membrane encases the inner ribcage, wherein the one or more ablation elements are disposed on the inner ribcage, wherein the inner ribcage comprises a first wall and a second wall extending parallel to the first wall;
   a vacuum supply configured to deliver suction through the inner recess to draw a portion of the patient tissue into the inner recess, wherein inner ribcage permits movement of the first wall and the second wall upon application of a vacuum from the vacuum supply; and
   wherein when tissue is drawn into the inner recess upon application of a vacuum from the vacuum supply, the web assembly is drawn into the inner recess, wherein the vacuum supply is configured to deliver suction through the inner recess to draw a portion of the patient tissue into the inner recess and into proximity with the one or more ablation elements.

9. The surgical system according to claim 8, wherein the one or more ablation elements are adjustable in response to movement of the first wall and the second wall to accommodate a variety of tissue thicknesses.

10. The surgical system according to claim 8, wherein the one or more ablation elements are adjustable in response to movement of the web assembly.

11. The surgical system according to claim 8, wherein the inner ribcage comprises a plurality of individual ribs, wherein the plurality of individual ribs bend in response to the thickness of the tissue.

12. The surgical system according to claim 8, further comprising a temperature sensor disposed along the inner recess.

13. The surgical system according to claim 8, wherein the housing comprises a cooling lumen.

14. The surgical system according to claim 8, wherein the housing comprises an irrigation lumen.

15. The surgical system according to claim 8, further comprising a power source assembly configured to deliver energy to the ablation element.

\* \* \* \* \*